(12) United States Patent
Gaines et al.

(10) Patent No.: US 6,576,750 B1
(45) Date of Patent: Jun. 10, 2003

(54) FLEA PERITROPHIN NUCLEIC ACID MOLECULES, PROTEINS AND USES THEREOF

(75) Inventors: Patrick J. Gaines, Fort Collins, CO (US); Nancy Wisnewski, Fort Collins, CO (US)

(73) Assignee: Heska Corporation, Fort Collins, CO (US)

( * ) Notice: Subject to any disclaimer, the term of this patent is extended or adjusted under 35 U.S.C. 154(b) by 237 days.

(21) Appl. No.: 09/686,583

(22) Filed: Oct. 11, 2000

Related U.S. Application Data

(63) Continuation-in-part of application No. 09/543,668, filed on Apr. 7, 2000.
(60) Provisional application No. 60/128,704, filed on Apr. 9, 1999.

(51) Int. Cl.$^7$ .......................... C07H 21/04; C12Q 1/68; C12P 21/06; A01N 43/04
(52) U.S. Cl. ................. 536/23.1; 536/23.51; 435/6; 435/69.1; 435/69.4; 514/55
(58) Field of Search .................. 435/6, 69.1, 69.2, 435/69.3, 69.7, 348; 536/23.51; 514/55

(56) References Cited

PUBLICATIONS

Attwood (Science, 290:471–473, 2000).*
Gerhold et al. (BioEssays, 18(12):973–981, 1996).*
Wells et al. (Journal of Leukocyte Biology, 61(5):545–550, 1997).*
Russell et al. (Journal of Molecular Biology, 244:332–350, 1994).*
Genbank Accession No. AA713920, Feb. 18, 1998.*
Barry et al., 1999, *Insect Biochemistry and Molecular Biology*, 29, pp. 319–327.
Casu et al., 1997, *Proc. Natl. Acad. Sci. USA*, vol. 94, pp. 8939–8944.
East et al., 1993, *International Journal for Parasitology*, vol. 23, No. 2, pp. 221–229.
East et al., 1993, *Immunology and Cell Biology*, 71, pp. 453–462.
Eisemann et al., 1994, *International Journal for Parasitology*, vol. 24, No. 1, pp. 15–26.
Elvin et al., 1996, *The Journal of Biological Chemistry*, vol. 271, No. 15, pp. 8925–8935.
Ramasamy et al., 1996, *J. Med. Entomol.*, vol. 33, No. 1, pp. 162–164.
Ramasamy et al., 1997, *Biochimica et Biophysica Acta*, 1361, pp. 114–122.
Schorderet et al., 1998, *Insect Biochem. Molec. Biol.*, vol. 28, No. 2, pp. 99–111.
Shen et al., 1998, *The Journal of Biological Chemistry*, vol. 273, No. 28, pp. 17665–17670.
Srikrishnaraj et al., 1995, *Medical and Veterinary Entomology*, 9, pp. 353–357.
Tellam et al., 1999, *Insect Biochemistry and Molecular Biology*, 29, pp. 87–101.
Wijffels et al., 1989, *International Journal for Parasitology*, 29, pp. 1363–1377.

* cited by examiner

*Primary Examiner*—Mary K. Zeman
*Assistant Examiner*—Lori A Clow
(74) *Attorney, Agent, or Firm*—Heska Corporation

(57) ABSTRACT

The present invention relates to flea peritrophin proteins; to flea peritrophin nucleic acid molecules, including those that encode such flea peritrophin proteins; to antibodies raised against such proteins; and to compounds that inhibit the activity of such proteins. The present invention also includes methods to obtain and use such proteins, nucleic acid molecules, antibodies, and inhibitory compounds. The present invention also includes therapeutic compositions comprising such inhibitory compounds, particularly those that specifically inhibit flea peritrophin activity, as well as the use of such therapeutic compositions to treat animals.

11 Claims, No Drawings

SEQUENCE LISTING

<160> NUMBER OF SEQ ID NOS: 68

<210> SEQ ID NO 1
<211> LENGTH: 1096
<212> TYPE: DNA

<213> ORGANISM: Ctenocephalides felis
<220> FEATURE:
<221> NAME/KEY: CDS
<222> LOCATION: (6)..(821)
<223> OTHER INFORMATION:

<400> SEQUENCE: 1

| | | | | | | | | | | | | | | | | |
|---|---|---|---|---|---|---|---|---|---|---|---|---|---|---|---|---|
| tcaca | atg | aag | ttc | tta | gga | gct | tta | ttg | gtt | gca | gtg | ttt | gcc | ttg | ggt | 50 |
| | Met | Lys | Phe | Leu | Gly | Ala | Leu | Leu | Val | Ala | Val | Phe | Ala | Leu | Gly | |
| | 1 | | | 5 | | | | | 10 | | | | | 15 | | |

| gct | gtg | gct | gct | gac | agg | aat | tcg | ccc | aca | tat | gtc | cgc | ggt | ttc | cca | 98 |
|---|---|---|---|---|---|---|---|---|---|---|---|---|---|---|---|---|
| Ala | Val | Ala | Ala | Asp | Arg | Asn | Ser | Pro | Thr | Tyr | Val | Arg | Gly | Phe | Pro | |
| | | | 20 | | | | | 25 | | | | | 30 | | | |

| gtg | gga | aga | tcc | aga | gca | cga | aca | aca | ttt | ggc | aat | gaa | gaa | ata | aag | 146 |
|---|---|---|---|---|---|---|---|---|---|---|---|---|---|---|---|---|
| Val | Gly | Arg | Ser | Arg | Ala | Arg | Thr | Thr | Phe | Gly | Asn | Glu | Glu | Ile | Lys | |
| | | 35 | | | | | 40 | | | | | 45 | | | | |

| tgt | act | aat | aag | cag | ttg | gga | aca | ttt | tgt | cac | gat | tgt | tct | act | ttg | 194 |
|---|---|---|---|---|---|---|---|---|---|---|---|---|---|---|---|---|
| Cys | Thr | Asn | Lys | Gln | Leu | Gly | Thr | Phe | Cys | His | Asp | Cys | Ser | Thr | Leu | |
| | 50 | | | | | 55 | | | | | 60 | | | | | |

| aag | ttg | tgc | gct | gga | caa | gaa | acc | cca | att | aca | aca | atc | aat | tgc | aga | 242 |
|---|---|---|---|---|---|---|---|---|---|---|---|---|---|---|---|---|
| Lys | Leu | Cys | Ala | Gly | Gln | Glu | Thr | Pro | Ile | Thr | Thr | Ile | Asn | Cys | Arg | |
| 65 | | | | | 70 | | | | | 75 | | | | | | |

| gac | tca | aat | tcc | gat | gct | cca | ttt | tgt | gta | gat | gat | atg | tgc | tca | tca | 290 |
|---|---|---|---|---|---|---|---|---|---|---|---|---|---|---|---|---|
| Asp | Ser | Asn | Ser | Asp | Ala | Pro | Phe | Cys | Val | Asp | Asp | Met | Cys | Ser | Ser | |
| 80 | | | | 85 | | | | | 90 | | | | | 95 | | |

| aaa | cct | ggg | gaa | aac | tgt | aag | acg | gca | gaa | act | aca | tgc | gcc | gtt | gta | 338 |
|---|---|---|---|---|---|---|---|---|---|---|---|---|---|---|---|---|
| Lys | Pro | Gly | Glu | Asn | Cys | Lys | Thr | Ala | Glu | Thr | Thr | Cys | Ala | Val | Val | |
| | | | 100 | | | | | 105 | | | | | 110 | | | |

| gga | tat | cag | cca | gat | ccg | aaa | gac | tgc | aca | aga | tac | tta | ttc | tgc | aaa | 386 |
|---|---|---|---|---|---|---|---|---|---|---|---|---|---|---|---|---|
| Gly | Tyr | Gln | Pro | Asp | Pro | Lys | Asp | Cys | Thr | Arg | Tyr | Leu | Phe | Cys | Lys | |
| | | 115 | | | | | 120 | | | | | 125 | | | | |

| gat | ggt | aaa | ggt | cag | gtt | ttc | gaa | tgc | cca | cct | aac | tat | gta | tat | gat | 434 |
|---|---|---|---|---|---|---|---|---|---|---|---|---|---|---|---|---|
| Asp | Gly | Lys | Gly | Gln | Val | Phe | Glu | Cys | Pro | Pro | Asn | Tyr | Val | Tyr | Asp | |
| | 130 | | | | | 135 | | | | | 140 | | | | | |

| cat | tct | aaa | aat | atg | tgt | aaa | aag | aaa | tcg | tca | gaa | gct | gat | tgc | acc | 482 |
|---|---|---|---|---|---|---|---|---|---|---|---|---|---|---|---|---|
| His | Ser | Lys | Asn | Met | Cys | Lys | Lys | Lys | Ser | Ser | Glu | Ala | Asp | Cys | Thr | |
| 145 | | | | | 150 | | | | | 155 | | | | | | |

| gtc | atg | aaa | tgc | aca | aat | ccc | aat | tct | ttt | ata | acc | tat | gca | ccg | gac | 530 |
|---|---|---|---|---|---|---|---|---|---|---|---|---|---|---|---|---|
| Val | Met | Lys | Cys | Thr | Asn | Pro | Asn | Ser | Phe | Ile | Thr | Tyr | Ala | Pro | Asp | |
| 160 | | | | 165 | | | | | 170 | | | | | 175 | | |

| cca | tca | att | tat | gct | tgg | tgc | aat | gac | aaa | ttg | caa | ccg | atc | gta | ctg | 578 |
|---|---|---|---|---|---|---|---|---|---|---|---|---|---|---|---|---|
| Pro | Ser | Ile | Tyr | Ala | Trp | Cys | Asn | Asp | Lys | Leu | Gln | Pro | Ile | Val | Leu | |
| | | | 180 | | | | | 185 | | | | | 190 | | | |

| aaa | tgt | gaa | gac | gac | gtc | aac | gaa | tgg | ttt | gac | cca | aaa | tct | ttc | tcg | 626 |
|---|---|---|---|---|---|---|---|---|---|---|---|---|---|---|---|---|
| Lys | Cys | Glu | Asp | Asp | Val | Asn | Glu | Trp | Phe | Asp | Pro | Lys | Ser | Phe | Ser | |
| | | | 195 | | | | | 200 | | | | | 205 | | | |

| tgc | aga | act | gca | tgc | aaa | agt | gaa | aac | gtt | ttt | tcc | gat | cga | aga | gat | 674 |
|---|---|---|---|---|---|---|---|---|---|---|---|---|---|---|---|---|
| Cys | Arg | Thr | Ala | Cys | Lys | Ser | Glu | Asn | Val | Phe | Ser | Asp | Arg | Arg | Asp | |
| | | 210 | | | | | 215 | | | | | 220 | | | | |

| tgt | aaa | aaa | tat | tat | caa | tgt | ttc | ttg | gtt | aac | aac | aaa | tgg | caa | ata | 722 |
|---|---|---|---|---|---|---|---|---|---|---|---|---|---|---|---|---|
| Cys | Lys | Lys | Tyr | Tyr | Gln | Cys | Phe | Leu | Val | Asn | Asn | Lys | Trp | Gln | Ile | |
| | 225 | | | | | 230 | | | | | 235 | | | | | |

| aaa | cat | tat | gat | tgt | cca | aat | ggc | ttg | cac | ttt | gat | aaa | acg | gag | ttg | 770 |
|---|---|---|---|---|---|---|---|---|---|---|---|---|---|---|---|---|
| Lys | His | Tyr | Asp | Cys | Pro | Asn | Gly | Leu | His | Phe | Asp | Lys | Thr | Glu | Leu | |
| 240 | | | | 245 | | | | | 250 | | | | | 255 | | |

| cga | tgc | ata | ccc | acg | cca | ccc | ggc | gaa | gaa | tgc | aaa | agt | gag | att | gct | 818 |
|---|---|---|---|---|---|---|---|---|---|---|---|---|---|---|---|---|
| Arg | Cys | Ile | Pro | Thr | Pro | Pro | Gly | Glu | Glu | Cys | Lys | Ser | Glu | Ile | Ala | |
| | | | 260 | | | | | 265 | | | | | 270 | | | |

| aag | taaggcttaa | accaggaaaa | caatcttgaa | tagactaatt | aggattcaaa | | 871 |
|---|---|---|---|---|---|---|---|
| Lys | | | | | | | |

-continued ttatcataaa gtagtcaatt aatataataa atacacaaat gatctgtgca attaaatata      931
aaaaatatgt ttaaaaatta aaatgtataa aattgtattt tatgtaagga gcacaaacaa      991
aatgtcctta actatagtaa tttctgatta tttaaaaat ataaatatag aagctttatg      1051
aaattacatg tatcttttta ataaaaataa atcgtttggg ccgtt                    1096

<210> SEQ ID NO 2
<211> LENGTH: 272
<212> TYPE: PRT
<213> ORGANISM: Ctenocephalides felis

<400> SEQUENCE: 2

```
Met Lys Phe Leu Gly Ala Leu Leu Val Ala Val Phe Ala Leu Gly Ala
1               5                   10                  15

Val Ala Ala Asp Arg Asn Ser Pro Thr Tyr Val Arg Gly Phe Pro Val
                20                  25                  30

Gly Arg Ser Arg Ala Arg Thr Thr Phe Gly Asn Glu Glu Ile Lys Cys
            35                  40                  45

Thr Asn Lys Gln Leu Gly Thr Phe Cys His Asp Cys Ser Thr Leu Lys
        50                  55                  60

Leu Cys Ala Gly Gln Glu Thr Pro Ile Thr Thr Ile Asn Cys Arg Asp
65                  70                  75                  80

Ser Asn Ser Asp Ala Pro Phe Cys Val Asp Asp Met Cys Ser Ser Lys
                85                  90                  95

Pro Gly Glu Asn Cys Lys Thr Ala Glu Thr Thr Cys Ala Val Val Gly
            100                 105                 110

Tyr Gln Pro Asp Pro Lys Asp Cys Thr Arg Tyr Leu Phe Cys Lys Asp
        115                 120                 125

Gly Lys Gly Gln Val Phe Glu Cys Pro Pro Asn Tyr Val Tyr Asp His
    130                 135                 140

Ser Lys Asn Met Cys Lys Lys Ser Ser Glu Ala Asp Cys Thr Val
145                 150                 155                 160

Met Lys Cys Thr Asn Pro Asn Ser Phe Ile Thr Tyr Ala Pro Asp Pro
                165                 170                 175

Ser Ile Tyr Ala Trp Cys Asn Asp Lys Leu Gln Pro Ile Val Leu Lys
            180                 185                 190

Cys Glu Asp Asp Val Asn Glu Trp Phe Asp Pro Lys Ser Phe Ser Cys
        195                 200                 205

Arg Thr Ala Cys Lys Ser Glu Asn Val Phe Ser Asp Arg Arg Asp Cys
    210                 215                 220

Lys Lys Tyr Tyr Gln Cys Phe Leu Val Asn Asn Lys Trp Gln Ile Lys
225                 230                 235                 240

His Tyr Asp Cys Pro Asn Gly Leu His Phe Asp Lys Thr Glu Leu Arg
                245                 250                 255

Cys Ile Pro Thr Pro Pro Gly Glu Glu Cys Lys Ser Glu Ile Ala Lys
            260                 265                 270
```

<210> SEQ ID NO 3
<211> LENGTH: 1096
<212> TYPE: DNA
<213> ORGANISM: Ctenocephalides felis

<400> SEQUENCE: 3
aacggcccaa acgatttatt tttattaaaa agatacatgt aatttcataa agcttctata      60
tttatatatt ttaaataatc agaaattact atagttaagg acattttgtt tgtgctcctt     120

-continued

| | |
|---|---|
| acataaaata caatttata cattttaatt tttaaacata tttttatat ttaattgcac | 180 |
| agatcatttg tgtatttatt atattaattg actactttat gataatttga atcctaatta | 240 |
| gtctattcaa gattgttttc ctggtttaag ccttacttag caatctcact tttgcattct | 300 |
| tcgccgggtg gcgtgggtat gcatcgcaac tccgttttat caaagtgcaa gccatttgga | 360 |
| caatcataat gttttatttg ccatttgttg ttaaccaaga aacattgata atatttttta | 420 |
| caatctcttc gatcggaaaa aacgttttca cttttgcatg cagttctgca cgagaaagat | 480 |
| tttgggtcaa accattcgtt gacgtcgtct tcacatttca gtacgatcgg ttgcaatttg | 540 |
| tcattgcacc aagcataaat tgatgggtcc ggtgcatagg ttataaaaga attgggattt | 600 |
| gtgcatttca tgacggtgca atcagcttct gacgatttct ttttacacat attttagaa | 660 |
| tgatcatata catagttagg tgggcattcg aaaacctgac ctttaccatc tttgcagaat | 720 |
| aagtatcttg tgcagtcttt cggatctggc tgatatccta caacggcgca tgtagtttct | 780 |
| gccgtcttac agttttcccc aggttttgat gagcacatat catctacaca aaatggagca | 840 |
| tcggaatttg agtctctgca attgattgtt gtaattgggg tttcttgtcc agcgcacaac | 900 |
| ttcaaagtag aacaatcgtg acaaaatgtt cccaactgct tattagtaca ctttattct | 960 |
| tcattgccaa atgttgttcg tgctctggat cttcccactg ggaaaccgcg gacatatgtg | 1020 |
| ggcgaattcc tgtcagcagc cacagcaccc aaggcaaaca ctgcaaccaa taaagctcct | 1080 |
| aagaacttca ttgtga | 1096 |

<210> SEQ ID NO 4
<211> LENGTH: 816
<212> TYPE: DNA
<213> ORGANISM: Ctenocephalides felis

<400> SEQUENCE: 4

| | |
|---|---|
| atgaagttct taggagcttt attggttgca gtgtttgcct tgggtgctgt ggctgctgac | 60 |
| aggaattcgc ccacatatgt ccgcggtttc ccagtgggaa gatccagagc acgaacaaca | 120 |
| tttggcaatg aagaaataaa gtgtactaat aagcagttgg gaacattttg tcacgattgt | 180 |
| tctactttga gttgtgcgc tggacaagaa accccaatta caacaatcaa ttgcagagac | 240 |
| tcaaattccg atgctccatt ttgtgtagat gatatgtgct catcaaaacc tggggaaaac | 300 |
| tgtaagacgg cagaaactac atgcgccgtt gtaggatatc agccagatcc gaaagactgc | 360 |
| acaagatact tattctgcaa agatggtaaa ggtcaggttt tcgaatgccc acctaactat | 420 |
| gtatatgatc attctaaaaa tatgtgtaaa aagaaatcgt cagaagctga ttgcaccgtc | 480 |
| atgaaatgca caaatcccaa ttcttttata acctatgcac cggacccatc aatttatgct | 540 |
| tggtgcaatg acaaattgca accgatcgta ctgaaatgtg aagacgacgt caacgaatgg | 600 |
| tttgacccaa atctttctc gtgcagaact gcatgcaaaa gtgaaaacgt tttttccgat | 660 |
| cgaagagatt gtaaaaaata ttatcaatgt ttcttggtta acaacaaatg gcaaataaaa | 720 |
| cattatgatt gtccaaatgg cttgcacttt gataaaacgg agttgcgatg catacccacg | 780 |
| ccacccggcg aagaatgcaa aagtgagatt gctaag | 816 |

<210> SEQ ID NO 5
<211> LENGTH: 816
<212> TYPE: DNA
<213> ORGANISM: Ctenocephalides felis

<400> SEQUENCE: 5

| | |
|---|---|
| cttagcaatc tcacttttgc attcttcgcc gggtggcgtg gtatgcatc gcaactccgt | 60 |

-continued

| | |
|---|---|
| tttatcaaag tgcaagccat ttggacaatc ataatgtttt atttgccatt tgttgttaac | 120 |
| caagaaacat tgataatatt ttttacaatc tcttcgatcg gaaaaaacgt tttcactttt | 180 |
| gcatgcagtt ctgcacgaga aagattttgg gtcaaaccat tcgttgacgt cgtcttcaca | 240 |
| tttcagtacg atcggttgca atttgtcatt gcaccaagca taaattgatg ggtccggtgc | 300 |
| ataggttata aaagaattgg gatttgtgca tttcatgacg gtgcaatcag cttctgacga | 360 |
| tttctttttta cacatatttt tagaatgatc atatacatag ttaggtgggc attcgaaaac | 420 |
| ctgacccttta ccatctttgc agaataagta tcttgtgcag tctttcggat ctggctgata | 480 |
| tcctacaacg gcgcatgtag tttctgccgt cttacagttt tccccaggtt ttgatgagca | 540 |
| catatcatct acacaaaatg gagcatcgga atttgagtct ctgcaattga ttgttgtaat | 600 |
| tggggtttct tgtccagcgc acaacttcaa agtagaacaa tcgtgacaaa atgttcccaa | 660 |
| ctgcttatta gtacacttta tttcttcatt gccaaatgtt gttcgtgctc tggatcttcc | 720 |
| cactgggaaa ccgcggacat atgtgggcga attcctgtca gcagccacag cacccaaggc | 780 |
| aaacactgca accaataaag ctcctaagaa cttcat | 816 |

<210> SEQ ID NO 6
<211> LENGTH: 445
<212> TYPE: DNA
<213> ORGANISM: Ctenocephalides felis

<400> SEQUENCE: 6

| | |
|---|---|
| gcaaacaaca aggtccgctg atgcaagatc cacacgattg tcacgcatat tacacatgtc | 60 |
| tagaaattgg atcattaccg aaacatttta attgtaataa aggtgcttat ttcaatacag | 120 |
| tcaaattaaa atgcgtgaaa ggaaattgcg aaaatagcac agaaattcct cttcctgagc | 180 |
| ttccagacat ttgcgatgaa gtaggacctt tggtgcaaga tccaaacgat tgccgcaagt | 240 |
| attattcatg cgtcacgatt ggaaagaaac ctgaacattt tacgtgcaat aaaggggcgt | 300 |
| attttgatcg agaaagatta cggtgtgtca gaggatcttg ttaacaaata ttgttatata | 360 |
| acaaagttca atctttaatt attatttaga agaatttgaa aatgtatatt taatgttttt | 420 |
| taataaaata gtttattggc aattt | 445 |

<210> SEQ ID NO 7
<211> LENGTH: 1279
<212> TYPE: DNA
<213> ORGANISM: Ctenocephalides felis

<400> SEQUENCE: 7

| | |
|---|---|
| gattagctgc ccactatagg gctaaagcgg ccgccgggtg tgttctgca gatccaagcc | 60 |
| catgtttctc ggaaggttct ataacttgca ccggtccagg agttttttcct gatccgtatg | 120 |
| attgtcagcg ttatcatgaa tgtaaaactg caaatgaatc atctaagcct gtcgagtgtg | 180 |
| ggggttacaa ggcttataat gttatagaaa ataattgtag cctgaacatg aatcatcaat | 240 |
| cgtgtaaacg cttacaattt cattgtgata ctataggaga tgaaaatgct tggccgagca | 300 |
| atagaaatat atattatagg tgcaccgaaa aaaccttgtg gttcaatagc aacaaaatat | 360 |
| tatatccttt attatatcgg tgtgatgaga gtgagatata tgatgcagtg cagagagttt | 420 |
| gcgtaagaga tgaaaccacc acgacgcctg ccacaacgcc aaccgaatct tccacgtcta | 480 |
| gtgaaacaac cacgacgtct gccacaacat caaccgaatc ttccacgtct agtgaaacaa | 540 |
| ccacgacgtc tgccacaaca ccaaccgaat cttccacgtc tagtgaaaca accacgacgt | 600 |
| ctgccacaac accaaccgaa tcttccacgt ctagtgaaac aaccacgacg tctgccacaa | 660 |

-continued

```
caccaaccga atcttccacg tctagtgaaa caaccacgac gtctgccaca acaccaaccg    720
aatcttccac gtctggtgaa acaaccacga cgtctgccac aacaccaacc gaaccttcca    780
caaagcctac ttctacggaa actcccgcaa caaaaccacc gcaagaaata ccatgcaaac    840
aacaaggtcc gctgatgcaa gatccacacg attgtcacgc atattacaca tgtctagaaa    900
ttggatcatt accgaaacat tttaattgta ataaaggtgc ttatttcaat acagtcaaat    960
taaaatgcgt gaaggaaat tgcgaaaata gcacagaaat tcctcttcct gagcttccag    1020
acatttgcga tgaagtagga cctttggtgc aagatccaaa cgattgccgc aagtattatt    1080
catgcgtcac gattggaaaa gaacctgaac attttacgtg caataaaggg gcgtattttg    1140
atcgagaaag attacggtgt gtcagaggat cttgttaaca atattgtta tataacaaag    1200 ttcaatcttt aattattatt tagaagaatt tgaaaatgta tatttaatgt tttttaataa    1260
aatagtttat tggcaattt                                                 1279
```

<210> SEQ ID NO 8
<211> LENGTH: 1279
<212> TYPE: DNA
<213> ORGANISM: Ctenocephalides felis

<400> SEQUENCE: 8

```
aaattgccaa taaactattt tattaaaaaa cattaaatat acattttcaa attcttctaa     60
ataataatta aagattgaac tttgttatat aacaatattt gttaacaaga tcctctgaca    120
caccgtaatc tttctcgatc aaaatacgcc cctttattgc acgtaaaatg ttcaggttct    180
tttccaatcg tgacgcatga ataatacttg cggcaatcgt ttggatcttg caccaaaggt    240
cctacttcat cgcaaatgtc tggaagctca ggaagaggaa tttctgtgct attttcgcaa    300
tttcctttca cgcattttaa tttgactgta ttgaaataag cacctttatt acaattaaaa    360
tgtttcggta atgatccaat ttctagacat gtgtaatatg cgtgacaatc gtgtggatct    420
tgcatcagcg gaccttgttg tttgcatggt atttcttgcg gtggttttgt tgcgggagtt    480
tccgtagaag taggctttgt ggaaggttcg gttggtgttg tggcagacgt cgtggttgtt    540
tcaccagacg tggaagattc ggttggtgtt gtggcagacg tcgtggttgt ttcactagac    600
gtggaagatt cggttggtgt tgtggcagac gtcgtggttt tttcactaga cgtggaagat    660
tcggttggtg ttgtggcaga cgtcgtggtt gtttcactag acgtggaaga ttcggttggt    720
gttgtggcag acgtcgtggt tgtttcacta gacgtggaag attcggttga tgttgtggca    780
gacgtcgtgg ttgtttcact agacgtggaa gattcggttg gcgttgtggc aggcgtcgtg    840
gtggtttcat ctcttacgca aactctctgc actgcatcat atatctcact ctcatcacac    900
cgatataata aaggatataa tattttgttg ctattgaacc acaaggtttt ttcggtgcac    960
ctataatata tatttctatt gctcggccaa gcattttcat ctcctatagt atcacaatga    1020
aattgtaagc gtttacacga ttgatgattc atgttcaggc tacaattatt ttctataaca    1080
ttataagcct tgtaaccccc acactcgaca ggcttagatg attcatttgc agttttacat    1140
tcatgataac gctgacaatc atacggatca ggaaaaactc ctggaccggt gcaagttata    1200
gaaccttccg agaaacatgg gcttggatct gcagaacacc acccggcggc cgctttagcc    1260
ctatagtggg cagctaatc                                                  1279
```

<210> SEQ ID NO 9
<211> LENGTH: 279
<212> TYPE: DNA
<213> ORGANISM: Ctenocephalides felis -continued

```
<400> SEQUENCE: 9
caatgatcaa gtcagttata attgtggcca acttttggct attcgtagcc ttgcaatcga      60
ttgataatcg gcagactaac aactgctctg agattggtgt tgatggtttt ttttgtctca     120
actgcagcgt cacagctttt gtggtagag gacctacggg tgaattcaac accgtgtcta     180
caagtccatg tagttctggt gaagtttgca gtacctgggc gggtagatgt tctgcagatc     240
caagcccatg tttctcggaa ggttctataa cttgcaccg                            279

<210> SEQ ID NO 10
<211> LENGTH: 279
<212> TYPE: DNA
<213> ORGANISM: Ctenocephalides felis

<400> SEQUENCE: 10
cggtgcaagt tatagaacct tccgagaaac atgggcttgg atctgcagaa catctacccg      60
cccaggtact gcaaacttca ccagaactac atggacttgt agacacggtg ttgaattcac     120
ccgtaggtcc tctaccacaa aaagctgtga cgctgcagtt gagacaaaaa aaaccatcaa     180
caccaatctc agagcagttg ttagtctgcc gattatcaat cgattgcaag gctacgaata     240
gccaaaagtt ggccacaatt ataactgact tgatcattg                            279

<210> SEQ ID NO 11
<211> LENGTH: 1465
<212> TYPE: DNA
<213> ORGANISM: Ctenocephalides felis
<220> FEATURE:
<221> NAME/KEY: CDS
<222> LOCATION: (3)..(1361)
<223> OTHER INFORMATION:

<400> SEQUENCE: 11 ca atg atc aag tca gtt ata att gtg gcc aac ttt tgg cta ttc gta         47
   Met Ile Lys Ser Val Ile Ile Val Ala Asn Phe Trp Leu Phe Val
   1               5                  10                  15 gcc ttg caa tcg att gat aat cgg cag act aac aac tgc tct gag att        95
Ala Leu Gln Ser Ile Asp Asn Arg Gln Thr Asn Asn Cys Ser Glu Ile
            20                  25                  30 ggt gtt gat ggt ttt ttt tgt ctc aac tgc agc gtc aca gct ttt tgt       143
Gly Val Asp Gly Phe Phe Cys Leu Asn Cys Ser Val Thr Ala Phe Cys
        35                  40                  45 ggt aga gga cct acg ggt gaa ttc aac acc gtg tct aca agt cca tgt       191
Gly Arg Gly Pro Thr Gly Glu Phe Asn Thr Val Ser Thr Ser Pro Cys
    50                  55                  60 agt tct ggt gaa gtt tgc agt acc tgg gcg ggt aga tgt tct gca gat       239
Ser Ser Gly Glu Val Cys Ser Thr Trp Ala Gly Arg Cys Ser Ala Asp
65                  70                  75 cca agc cca tgt ttc tcg gaa ggt tct ata act tgc acc ggt cca gga       287
Pro Ser Pro Cys Phe Ser Glu Gly Ser Ile Thr Cys Thr Gly Pro Gly
            80                  85                  90                  95 gtt ttt cct gat ccg tat gat tgt cag cgt tat cat gaa tgt aaa act       335
Val Phe Pro Asp Pro Tyr Asp Cys Gln Arg Tyr His Glu Cys Lys Thr
                100                 105                 110 gca aat gaa tca tct aag cct gtc gag tgt ggg ggt tac aag gct tat       383
Ala Asn Glu Ser Ser Lys Pro Val Glu Cys Gly Gly Tyr Lys Ala Tyr
            115                 120                 125 aat gtt ata gaa aat aat tgt agc ctg aac atg aat cat caa tcg tgt       431
Asn Val Ile Glu Asn Asn Cys Ser Leu Asn Met Asn His Gln Ser Cys
        130                 135                 140
```

```
aaa cgc tta caa ttt cat tgt gat act ata gga gat gaa aat gct tgg        479
Lys Arg Leu Gln Phe His Cys Asp Thr Ile Gly Asp Glu Asn Ala Trp
    145                 150                 155 ccg agc aat aga aat ata tat tat agg tgc acc gaa aaa acc ttg tgg        527
Pro Ser Asn Arg Asn Ile Tyr Tyr Arg Cys Thr Glu Lys Thr Leu Trp
160                 165                 170                 175 ttc aat agc aac aaa ata tta tat cct tta tta tat cgg tgt gat gag        575
Phe Asn Ser Asn Lys Ile Leu Tyr Pro Leu Leu Tyr Arg Cys Asp Glu
                180                 185                 190 agt gag ata tat gat gca gtg cag aga gtt tgc gta aga gat gaa acc        623
Ser Glu Ile Tyr Asp Ala Val Gln Arg Val Cys Val Arg Asp Glu Thr
            195                 200                 205 acc acg acg cct gcc aca acg cca acc gaa tct tcc acg tct agt gaa        671
Thr Thr Thr Pro Ala Thr Thr Pro Thr Glu Ser Ser Thr Ser Ser Glu
        210                 215                 220 aca acc acg acg tct gcc aca aca tca acc gaa tct tcc acg tct agt        719
Thr Thr Thr Thr Ser Ala Thr Thr Ser Thr Glu Ser Ser Thr Ser Ser
    225                 230                 235 gaa aca acc acg acg tct gcc aca aca cca acc gaa tct tcc acg tct        767
Glu Thr Thr Thr Thr Ser Ala Thr Thr Pro Thr Glu Ser Ser Thr Ser
240                 245                 250                 255 agt gaa aca acc acg acg tct gcc aca aca cca acc gaa tct tcc acg        815
Ser Glu Thr Thr Thr Thr Ser Ala Thr Thr Pro Thr Glu Ser Ser Thr
                260                 265                 270 tct agt gaa aca acc acg acg tct gcc aca aca cca acc gaa tct tcc        863
Ser Ser Glu Thr Thr Thr Thr Ser Ala Thr Thr Pro Thr Glu Ser Ser
            275                 280                 285 acg tct agt gaa aca acc acg acg tct gcc aca aca cca acc gaa tct        911
Thr Ser Ser Glu Thr Thr Thr Thr Ser Ala Thr Thr Pro Thr Glu Ser
        290                 295                 300 tcc acg tct ggt gaa aca acc acg acg tct gcc aca aca cca acc gaa        959
Ser Thr Ser Gly Glu Thr Thr Thr Thr Ser Ala Thr Thr Pro Thr Glu
    305                 310                 315 cct tcc aca aag cct act tct acg gaa act ccc gca aca aaa cca ccg       1007
Pro Ser Thr Lys Pro Thr Ser Thr Glu Thr Pro Ala Thr Lys Pro Pro
320                 325                 330                 335 caa gaa ata cca tgc aaa caa caa ggt ccg ctg atg caa gat cca cac       1055
Gln Glu Ile Pro Cys Lys Gln Gln Gly Pro Leu Met Gln Asp Pro His
                340                 345                 350 gat tgt cac gca tat tac aca tgt cta gaa att gga tca tta ccg aaa       1103
Asp Cys His Ala Tyr Tyr Thr Cys Leu Glu Ile Gly Ser Leu Pro Lys
            355                 360                 365 cat ttt aat tgt aat aaa ggt gct tat ttc aat aca gtc aaa tta aaa       1151
His Phe Asn Cys Asn Lys Gly Ala Tyr Phe Asn Thr Val Lys Leu Lys
        370                 375                 380 tgc gtg aaa gga aat tgc gaa aat agc aca gaa att cct ctt cct gag       1199
Cys Val Lys Gly Asn Cys Glu Asn Ser Thr Glu Ile Pro Leu Pro Glu
    385                 390                 395 ctt cca gac att tgc gat gaa gta gga cct ttg gtg caa gat cca aac       1247
Leu Pro Asp Ile Cys Asp Glu Val Gly Pro Leu Val Gln Asp Pro Asn
400                 405                 410                 415 gat tgc cgc aag tat tat tca tgc gtc acg att gga aaa gaa cct gaa       1295
Asp Cys Arg Lys Tyr Tyr Ser Cys Val Thr Ile Gly Lys Glu Pro Glu
                420                 425                 430 cat ttt acg tgc aat aaa ggg gcg tat ttt gat cga gaa aga tta cgg       1343
His Phe Thr Cys Asn Lys Gly Ala Tyr Phe Asp Arg Glu Arg Leu Arg
            435                 440                 445 tgt gtc aga gga tct tgt taacaaatat tgttatataa caaagttcaa             1391
Cys Val Arg Gly Ser Cys
        450
```

-continued

```
tctttaatta ttatttagaa gaatttgaaa atgtatattt aatgtttttt aataaaatag     1451
tttattggca attt                                                      1465
```

<210> SEQ ID NO 12
<211> LENGTH: 453
<212> TYPE: PRT
<213> ORGANISM: Ctenocephalides felis

<400> SEQUENCE: 12

```
Met Ile Lys Ser Val Ile Ile Val Ala Asn Phe Trp Leu Phe Val Ala
1               5                   10                  15

Leu Gln Ser Ile Asp Asn Arg Gln Thr Asn Cys Ser Glu Ile Gly
            20                  25                  30

Val Asp Gly Phe Phe Cys Leu Asn Cys Ser Val Thr Ala Phe Cys Gly
        35                  40                  45

Arg Gly Pro Thr Gly Glu Phe Asn Thr Val Ser Thr Pro Cys Ser
    50                  55                  60

Ser Gly Glu Val Cys Ser Thr Trp Ala Gly Arg Cys Ser Ala Asp Pro
65                  70                  75                  80

Ser Pro Cys Phe Ser Glu Gly Ser Ile Thr Cys Thr Gly Pro Gly Val
                85                  90                  95

Phe Pro Asp Pro Tyr Asp Cys Gln Arg Tyr His Glu Cys Lys Thr Ala
            100                 105                 110

Asn Glu Ser Ser Lys Pro Val Glu Cys Gly Gly Tyr Lys Ala Tyr Asn
        115                 120                 125

Val Ile Glu Asn Asn Cys Ser Leu Asn Met Asn His Gln Ser Cys Lys
130                 135                 140

Arg Leu Gln Phe His Cys Asp Thr Ile Gly Asp Glu Asn Ala Trp Pro
145                 150                 155                 160

Ser Asn Arg Asn Ile Tyr Tyr Arg Cys Thr Glu Lys Thr Leu Trp Phe
                165                 170                 175

Asn Ser Asn Lys Ile Leu Tyr Pro Leu Leu Tyr Arg Cys Asp Glu Ser
            180                 185                 190

Glu Ile Tyr Asp Ala Val Gln Arg Val Cys Val Arg Asp Glu Thr Thr
        195                 200                 205

Thr Thr Pro Ala Thr Thr Pro Thr Glu Ser Ser Thr Ser Ser Glu Thr
    210                 215                 220

Thr Thr Thr Ser Ala Thr Thr Ser Thr Glu Ser Ser Thr Ser Ser Glu
225                 230                 235                 240

Thr Thr Thr Thr Ser Ala Thr Thr Pro Thr Glu Ser Ser Thr Ser Ser
                245                 250                 255

Glu Thr Thr Thr Thr Ser Ala Thr Thr Pro Thr Glu Ser Ser Thr Ser
            260                 265                 270

Ser Glu Thr Thr Thr Ser Ala Thr Thr Pro Thr Glu Ser Ser Thr
        275                 280                 285

Ser Ser Glu Thr Thr Thr Thr Ser Ala Thr Thr Pro Thr Glu Ser Ser
    290                 295                 300

Thr Ser Gly Glu Thr Thr Thr Ser Ala Thr Thr Pro Thr Glu Pro
305                 310                 315                 320

Ser Thr Lys Pro Thr Ser Thr Glu Thr Pro Ala Thr Lys Pro Pro Gln
                325                 330                 335

Glu Ile Pro Cys Lys Gln Gln Gly Pro Leu Met Gln Asp Pro His Asp
            340                 345                 350
```

```
Cys His Ala Tyr Tyr Thr Cys Leu Glu Ile Gly Ser Leu Pro Lys His
            355                 360                 365

Phe Asn Cys Asn Lys Gly Ala Tyr Phe Asn Thr Val Lys Leu Lys Cys
        370                 375                 380

Val Lys Gly Asn Cys Glu Asn Ser Thr Glu Ile Pro Leu Pro Glu Leu
385                 390                 395                 400

Pro Asp Ile Cys Asp Glu Val Gly Pro Leu Val Gln Asp Pro Asn Asp
                405                 410                 415

Cys Arg Lys Tyr Tyr Ser Cys Val Thr Ile Gly Lys Glu Pro Glu His
                420                 425                 430

Phe Thr Cys Asn Lys Gly Ala Tyr Phe Asp Arg Glu Arg Leu Arg Cys
        435                 440                 445

Val Arg Gly Ser Cys
    450

<210> SEQ ID NO 13
<211> LENGTH: 1465
<212> TYPE: DNA
<213> ORGANISM: Ctenocephalides felis

<400> SEQUENCE: 13
aaattgccaa taaactattt tattaaaaaa cattaaatat acattttcaa attcttctaa      60
ataataatta aagattgaac tttgttatat aacaatattt gttaacaaga tcctctgaca    120
caccgtaatc tttctcgatc aaaatacgcc cctttattgc acgtaaaatg ttcaggttct    180
tttccaatcg tgacgcatga ataatacttg cggcaatcgt ttggatcttg caccaaaggt    240
cctacttcat cgcaaatgtc tggaagctca ggaagaggaa tttctgtgct attttcgcaa    300
tttcctttca cgcatttttaa tttgactgta ttgaaataag cacctttatt acaattaaaa    360
tgtttcggta atgatccaat ttctagacat gtgtaatatg cgtgacaatc gtgtggatct    420
tgcatcagcg gaccttgttg tttgcatggt atttcttgcg gtggttttgt tgcgggagtt    480
tccgtagaag taggctttgt ggaaggttcg gttggtgttg tggcagacgt cgtggttgtt    540
tcaccagacg tggaagattc ggttggtgtt gtggcagacg tcgtggttgt ttcactagac    600
gtggaagatt cggttggtgt tgtggcagac gtcgtggttg tttcactaga cgtggaagat    660
tcggttggtg ttgtggcaga cgtcgtggtt gttttcactag acgtggaaga ttcggttggt    720
gttgtggcag acgtcgtggt tgtttcacta gacgtggaag attcggttga tgttgtggca    780
gacgtcgtgg ttgtttcact agacgtggaa gattcggttg cgttgtggc aggcgtcgtg    840
gtggtttcat ctcttacgca aactctctgc actgcatcat atatctcact ctcatcacac    900
cgatataata aaggatataa tattttgttg ctattgaacc acaaggtttt ttcggtgcac    960
ctataatata tatttctatt gctcggccaa gcattttcat ctcctatagt atcacaatga   1020
aattgtaagc gtttacacga ttgatgattc atgttcaggc tacaattatt ttctataaca   1080
ttataagcct tgtaaccccc acactcgaca ggcttagatg attcatttgc agttttacat   1140
tcatgataac gctgacaatc atacggatca ggaaaaactc ctggaccggt gcaagttata   1200
gaaccttccg agaaacatgg gcttggatct gcagaacatc tacccgccca ggtactgcaa   1260
acttcaccag aactacatgg acttgtagac acggtgttga attcacccgt aggtcctcta   1320
ccacaaaaag ctgtgacgct gcagttgaga caaaaaaaac catcaacacc aatctcagag   1380
cagttgttag tctgccgatt atcaatcgat tgcaaggcta cgaatagcca aaagttggcc   1440
acaattataa ctgacttgat cattg                                         1465
```

<210> SEQ ID NO 14
<211> LENGTH: 1359
<212> TYPE: DNA
<213> ORGANISM: Ctenocephalides felis

<400> SEQUENCE: 14

```
atgatcaagt cagttataat tgtggccaac ttttggctat tcgtagcctt gcaatcgatt      60
gataatcggc agactaacaa ctgctctgag attggtgttg atggtttttt ttgtctcaac     120
tgcagcgtca cagcttttg tggtagagga cctacgggtg aattcaacac cgtgtctaca     180
agtccatgta gttctggtga agtttgcagt acctgggcgg gtagatgttc tgcagatcca     240
agcccatgtt tctcggaagg ttctataact tgcaccggtc caggagtttt tcctgatccg     300
tatgattgtc agcgttatca tgaatgtaaa actgcaaatg aatcatctaa gcctgtcgag     360
tgtgggggtt acaaggctta taatgttata gaaataatt gtagcctgaa catgaatcat     420
caatcgtgta aacgcttaca atttcattgt gatactatag gagatgaaaa tgcttggccg     480
agcaatagaa atatatatta taggtgcacc gaaaaaacct tgtggttcaa tagcaacaaa     540
atattatatc ctttattata tcggtgtgat gagagtgaga tatatgatgc agtgcagaga     600
gtttgcgtaa gagatgaaac caccacgacg cctgccacaa cgccaaccga atcttccacg     660
tctagtgaaa caaccacgac gtctgccaca acatcaaccg aatcttccac gtctagtgaa     720
acaaccacga cgtctgccac aacaccaacc gaatcttcca cgtctagtga acaaccacg     780
acgtctgcca acaccaaac cgaatcttcc acgtctagtg aaacaaccac gacgtctgcc     840
acaacaccaa ccgaatcttc cacgtctagt gaaacaacca cgacgtctgc cacaacacca     900
accgaatctt ccacgtctgg tgaaacaacc acgacgtctg ccacaacacc aaccgaacct     960
tccacaaagc ctacttctac ggaaactccc gcaacaaaac caccgcaaga ataccatgc    1020
aaacaacaag gtccgctgat gcaagatcca cacgattgtc acgcatatta cacatgtcta    1080
gaaattggat cattaccgaa acattttaat tgtaataaag gtgcttattt caatacagtc    1140
aaattaaaat gcgtgaaagg aaattgcgaa aatagcacag aaattcctct tcctgagctt    1200
ccagacattt gcgatgaagt aggacctttg gtgcaagatc caaacgattg ccgcaagtat    1260
tattcatgcg tcacgattgg aaaagaacct gaacatttta cgtgcaataa aggggcgtat    1320
tttgatcgag aaagattacg gtgtgtcaga ggatcttgt                            1359
```

<210> SEQ ID NO 15
<211> LENGTH: 1359
<212> TYPE: DNA
<213> ORGANISM: Ctenocephalides felis

<400> SEQUENCE: 15

```
acaagatcct ctgacacacc gtaatctttc tcgatcaaaa tacgcccctt tattgcacgt      60
aaaatgttca ggttcttttc caatcgtgac gcatgaataa tacttgcggc aatcgtttgg     120
atcttgcacc aaaggtccta cttcatcgca aatgtctgga agctcaggaa gaggaatttc     180
tgtgctattt tcgcaatttc ctttcacgca ttttaatttg actgtattga ataagcacc     240
tttattacaa ttaaaatgtt tcggtaatga tccatttct agacatgtgt aatatgcgtg     300
acaatcgtgt ggatcttgca tcagcggacc ttgttgtttg catggtattt cttgcggtgg     360
ttttgttgcg ggagtttccg tagaagtagg ctttgtggaa ggttcggttg gtgttgtggc     420
agacgtcgtg gttgtttcac cagacgtgga agattcggtt ggtgttgtgg cagacgtcgt     480
ggttgtttca ctagacgtgg aagattcggt tggtgttgtg gcagacgtcg tggttgtttc     540
```

```
actagacgtg aagattcgg ttggtgttgt ggcagacgtc gtggttgttt cactagacgt    600
ggaagattcg gttggtgttg tggcagacgt cgtggttgtt tcactagacg tggaagattc    660
ggttgatgtt gtggcagacg tcgtggttgt ttcactagac gtggaagatt cggttggcgt    720
tgtggcaggc gtcgtggtgg tttcatctct tacgcaaact ctctgcactg catcatatat    780
ctcactctca tcacaccgat ataataaagg atataatatt tgttgctat tgaaccacaa     840 ggttttttcg gtgcacctat aatatatatt tctattgctc ggccaagcat tttcatctcc    900
tatagtatca caatgaaatt gtaagcgttt acacgattga tgattcatgt tcaggctaca    960
attattttct ataacattat aagccttgta accccccacac tcgacaggct tagatgattc   1020
atttgcagtt ttacattcat gataacgctg acaatcatac ggatcaggaa aaactcctgg   1080
accggtgcaa gttatagaac cttccgagaa acatgggctt ggatctgcag aacatctacc   1140
cgcccaggta ctgcaaactt caccagaact acatggactt gtagacacgg tgttgaattc   1200
acccgtaggt cctctaccac aaaaagctgt gacgctgcag ttgagacaaa aaaaccatc    1260 aacaccaatc tcagagcagt tgttagtctg ccgattatca atcgattgca aggctacgaa   1320
tagccaaaag ttggccacaa ttataactga cttgatcat                          1359
```

<210> SEQ ID NO 16
<211> LENGTH: 387
<212> TYPE: DNA
<213> ORGANISM: Ctenocephalides felis
<220> FEATURE:
<221> NAME/KEY: CDS
<222> LOCATION: (20)..(262)
<223> OTHER INFORMATION:

<400> SEQUENCE: 16

```
gttaatttaa aataacaaa atg aaa gga aca tta tta ata tta tca tgt ctt    52
                     Met Lys Gly Thr Leu Leu Ile Leu Ser Cys Leu
                      1               5                      10 gtg atc atg ata agt gcc gaa tat gct gac gta gat gtg tgc caa gat   100
Val Ile Met Ile Ser Ala Glu Tyr Ala Asp Val Asp Val Cys Gln Asp
         15                  20                  25 ttg gac gat gga act ttt ctt gct gat tca aac aat tgc caa aat ttc   148
Leu Asp Asp Gly Thr Phe Leu Ala Asp Ser Asn Asn Cys Gln Asn Phe
     30                  35                  40 ttc att tgt gat gga ggc cga gct tgg aaa atg tat tgt cca gga tca   196
Phe Ile Cys Asp Gly Gly Arg Ala Trp Lys Met Tyr Cys Pro Gly Ser
 45                  50                  55 ctt tta tgg aat gat cac gaa gga aca tgt gat tac gca caa aat gta   244
Leu Leu Trp Asn Asp His Glu Gly Thr Cys Asp Tyr Ala Gln Asn Val
 60                  65                  70                  75 gaa tgt tac caa cca gaa taaaacattt taatatctga cagcgatttt            292
Glu Cys Tyr Gln Pro Glu
                 80 ctgaaactat atttcatact actgttataa taaatttatc ttcattgctc tcctcctata   352 aatttattcc gttttaataa aatcaatata aagac                               387
```

<210> SEQ ID NO 17
<211> LENGTH: 81
<212> TYPE: PRT
<213> ORGANISM: Ctenocephalides felis

<400> SEQUENCE: 17

```
Met Lys Gly Thr Leu Leu Ile Leu Ser Cys Leu Val Ile Met Ile Ser
 1               5                  10                  15
```

```
Ala Glu Tyr Ala Asp Val Asp Val Cys Gln Asp Leu Asp Asp Gly Thr
            20                  25                  30

Phe Leu Ala Asp Ser Asn Asn Cys Gln Asn Phe Phe Ile Cys Asp Gly
        35                  40                  45

Gly Arg Ala Trp Lys Met Tyr Cys Pro Gly Ser Leu Leu Trp Asn Asp
    50                  55                  60

His Glu Gly Thr Cys Asp Tyr Ala Gln Asn Val Glu Cys Tyr Gln Pro
65                  70                  75                  80

Glu
```

<210> SEQ ID NO 18
<211> LENGTH: 387
<212> TYPE: DNA
<213> ORGANISM: Ctenocephalides felis

<400> SEQUENCE: 18

```
gtctttatat tgattttatt aaaacggaat aaatttatag gaggagagca atgaagataa      60
atttattata acagtagtat gaaatatagt ttcagaaaat cgctgtcaga tattaaaatg     120
ttttattctg gttggtaaca ttctacattt tgtgcgtaat cacatgttcc ttcgtgatca     180
ttccataaaa gtgatcctgg acaatacatt ttccaagctc ggcctccatc acaaatgaag     240
aaattttggc aattgtttga atcagcaaga aaagttccat cgtccaaatc ttggcacaca     300
tctacgtcag catattcggc acttatcatg atcacaagac atgataatat taataatgtt     360
cctttcattt tgttattta aattaac                                          387
```

<210> SEQ ID NO 19
<211> LENGTH: 243
<212> TYPE: DNA
<213> ORGANISM: Ctenocephalides felis

<400> SEQUENCE: 19

```
atgaaggaa cattattaat attatcatgt cttgtgatca tgataagtgc cgaatatgct       60
gacgtagatg tgtgccaaga tttggacgat ggaactttc ttgctgattc aaacaattgc      120
caaaatttct tcatttgtga tggaggccga gcttggaaaa tgtattgtcc aggatcactt     180
ttatggaatg atcacgaagg aacatgtgat tacgcacaaa atgtagaatg ttaccaacca     240
gaa                                                                   243
```

<210> SEQ ID NO 20
<211> LENGTH: 243
<212> TYPE: DNA
<213> ORGANISM: Ctenocephalides felis

<400> SEQUENCE: 20

```
ttctggttgg taacattcta cattttgtgc gtaatcacat gttccttcgt gatcattcca      60
taaaagtgat cctggacaat acattttcca agctcggcct ccatcacaaa tgaagaaatt     120
ttggcaattg tttgaatcag caagaaaagt tccatcgtcc aaatcttggc acacatctac     180
gtcagcatat tcggcactta tcatgatcac aagacatgat aatattaata atgttccttt     240
cat                                                                   243
```

<210> SEQ ID NO 21
<211> LENGTH: 960
<212> TYPE: DNA
<213> ORGANISM: Ctenocephalides felis

<400> SEQUENCE: 21

```
ttaatgtcga cggaacgcct ttaacagtaa ataaagaagt atttgcatca ttggatgagc      60
ccgcaccagg agtagtacct actcctgaac ctacacctgt accgaaaccc gagcaaaaat     120
gtaaaaaagt aaaatttagt tgcgtgaatt cgtgcagttc acccgaaatg cagtattgtc     180
cggaaatagg agcagatccg gttaaggaat cctgtagccc agatcaagtg tgcgctgatc     240
aaagtggata tctacagtgc accactaaag aaagtacagt ctgcaaagta caaggtttca     300
aatgtccgtc accatcgaga ttttatccaa atataaatga ttgtcaaagc tattattatt     360
gtgacgaaaa tagtatagga acccaatatt attgccccgc aaattttgca tatgatccgt     420
tacgtcataa ttgcggacct atggctctgg gcacaaaatg ctatacagtt acatgtcctg     480
cacagcctaa ggtgcttccg tacattggtg ataaatcatt gtacgtcgta tgtatggccg     540
gaagaggaac cgtattgcaa tgcgaagaac ccgccgagtt ttccccaagg agcgaaacct     600
gtgtcgggca atgccgagca cgtggaaaat ttgctttcaa gaacgacgca acatgccgga     660
agttcttcac cgtgtttacgt cctaaaggag agccagttcc tgatcaatgt ccgattggaa    720
cagtatttaa ccaagctact caaagctgca acacaggaac ttgcgagagg aaacctaaat    780
tatattaata tattgatgaa gtattcaaca aaagaaacta tacaaaatat gtactttgtt    840
ttactttatg tgttatataa aaaaatatta tggttgaaca caggctcgca aatatgataa   900
ggcatttaag aattttacaa tttagatttt tttaaatcca tgaatatatt tgttctaatc    960
```

<210> SEQ ID NO 22
<211> LENGTH: 960
<212> TYPE: DNA
<213> ORGANISM: Ctenocephalides felis

<400> SEQUENCE: 22

```
gattagaaca aatatattca tggatttaaa aaaatctaaa ttgtaaaatt cttaaatgcc      60
ttatcatatt tgcgagcctg tgttcaacca taatatttt ttatataaca cataaagtaa     120
aacaaagtac atattttgta tagtttcttt tgttgaatac ttcatcaata tattaatata    180
atttaggttt cctctcgcaa gttcctgtgt tgcagctttg agtagcttgg ttaaatactg     240
ttccaatcgg acattgatca ggaactggct ctccttttagg acgtaaacac gtgaagaact    300
tccggcatgt tgcgtcgttc ttgaaagcaa attttccacg tgctcggcat tgcccgacac    360
aggtttcgct ccttggggaa aactcggcgg gttcttcgca ttgcaatacg gttcctcttc   420
cggccataca tacgacgtac aatgatttat caccaatgta cggaagcacc ttaggctgtg    480
caggacatgt aactgtatag cattttgtgc ccagagccat aggtccgcaa ttatgacgta    540
acggatcata tgcaaaattt gcgggcaat aatattgggt tcctatacta ttttcgtcac     600
aataataata gctttgacaa tcatttatat ttggataaaa tctcgatggt gacggacatt    660
tgaaaccttg tactttgcag actgtacttt ctttagtggt gcactgtaga tatccacttt    720
gatcagcgca cacttgatct gggctacagg attccttaac cggatctgct cctatttccg    780
gacaatactg catttcgggt gaactgcacg aattcacgca actaaatttt actttttac     840
attttgctc gggtttcggt acaggtgtag gttcaggagt aggtactact cctggtgcgg     900
gctcatccaa tgatgcaaat acttcttat ttactgttaa aggcgttccg tcgacattaa      960
```

<210> SEQ ID NO 23
<211> LENGTH: 1029
<212> TYPE: DNA
<213> ORGANISM: Ctenocephalides felis

<400> SEQUENCE: 23

```
tgttttatat cacattggtt tttattagtt ttgtggcgtt atctgtcgtt accgcttatg      60
atggtgagtt taatgtcgac ggaacgcctt aacagtaaa taaagaagta tttgcatcat     120
tggatgagcc cgcaccagga gtagtaccta ctcctgaacc tacacctgta ccgaaacccg     180
agcaaaaatg taaaaagta aaatttagtt gcgtgaattc gtgcagttca cccgaaatgc     240
agtattgtcc ggaaatagga gcagatccgg ttaaggaatc ctgtagccca gatcaagtgt     300
gcgctgatca aagtggatat ctacagtgca ccactaaaga agtacagtc tgcaaagtac     360
aaggtttcaa atgtccgtca ccatcgagat tttatccaaa tataaatgat tgtcaaagct     420
attattattg tgacgaaaat agtataggaa cccaatatta ttgccccgca aattttgcat     480
atgatccgtt acgtcataat tgcggaccta tggctctggg cacaaaatgc tatacagtta     540
catgtcctgc acagcctaag gtgcttccgt acattggtga taaatcattg tacgtcgtat     600
gtatggccgg aagaggaacc gtattgcaat gcgaagaacc cgccgagttt tccccaagga     660
gcgaaacctg tgtcgggcaa tgccgagcac gtggaaaatt tgctttcaag aacgacgcaa     720
catgccggaa gttcttcacg tgtttacgtc ctaaaggaga gccagttcct gatcaatgtc     780
cgattggaac agtatttaac caagctactc aaagctgcaa cacaggaact tgcgagagga     840
aacctaaatt atattaatat attgatgaag tattcaacaa aagaaactat acaaaatatg     900
tactttgttt tacttatgt gttatataaa aaatattat ggttgaacac aggctcgcaa     960
atatgataag gcatttaaga attttacaat ttagatttt taaatccat gaatatattt    1020
gttctaatc                                                           1029
```

<210> SEQ ID NO 24
<211> LENGTH: 1029
<212> TYPE: DNA
<213> ORGANISM: Ctenocephalides felis

<400> SEQUENCE: 24

```
gattagaaca atatattca tggatttaaa aaaatctaaa ttgtaaaatt cttaaatgcc      60
ttatcatatt tgcgagcctg tgttcaacca taatattttt ttatataaca cataaagtaa     120
aacaaagtac atattttgta tagtttcttt tgttgaatac ttcatcaata tattaatata     180
atttaggttt cctctcgcaa gttcctgtgt tgcagctttg agtagcttgg ttaaatactg     240
ttccaatcgg acattgatca ggaactggct ctcctttagg acgtaaacac gtgaagaact     300
tccggcatgt tgcgtcgttc ttgaaagcaa attttccacg tgctcggcat tgcccgacac     360
aggtttcgct ccttggggaa aactcggcgg gttcttcgca ttgcaatacg gttcctcttc     420
cggccataca tacgacgtac aatgatttat caccaatgta cggaagcacc ttaggctgtg     480
caggacatgt aactgtatag cattttgtgc ccagagccat aggtccgcaa ttatgacgta     540
acggatcata tgcaaaattt gcggggcaat aatattgggt tcctatacta ttttcgtcac     600
aataataata gctttgacaa tcatttatat ttggataaaa tctcgatggt gacggacatt     660
tgaaaccttg tactttgcag actgtacttt ctttagtggt gcactgtaga tatccacttt     720
gatcagcgca cacttgatct gggctacagg attccttaac cggatctgct cctatttccg     780
gacaatactg catttcgggt gaactgcacg aattcacgca actaaatttt acttttttac     840
atttttgctc gggtttcggt acaggtgtag gttcaggagt aggtactact cctggtgcgg     900
gctcatccaa tgatgcaaat acttctttat ttactgttaa aggcgttccg tcgacattaa     960
```

-continued

```
actcaccatc ataagcggta acgacagata acgccacaaa actaataaaa accaatgtga    1020
tataaaaca                                                            1029

<210> SEQ ID NO 25
<211> LENGTH: 1048
<212> TYPE: DNA
<213> ORGANISM: Ctenocephalides felis
<220> FEATURE:
<221> NAME/KEY: CDS
<222> LOCATION: (19)..(873)
<223> OTHER INFORMATION:

<400> SEQUENCE: 25
gtaacatatt tattaaga atg ttt tat atc aca ttg gtt ttt att agt ttt        51
                    Met Phe Tyr Ile Thr Leu Val Phe Ile Ser Phe
                     1               5                  10 gtg gcg tta tct gtc gtt acc gct tat gat ggt gag ttt aat gtc gac       99
Val Ala Leu Ser Val Val Thr Ala Tyr Asp Gly Glu Phe Asn Val Asp
             15                  20                  25 gga acg cct tta aca gta aat aaa gaa gta ttt gca tca ttg gat gag      147
Gly Thr Pro Leu Thr Val Asn Lys Glu Val Phe Ala Ser Leu Asp Glu
         30                  35                  40 ccc gca cca gga gta gta cct act cct gaa cct aca cct gta ccg aaa      195
Pro Ala Pro Gly Val Val Pro Thr Pro Glu Pro Thr Pro Val Pro Lys
     45                  50                  55 ccc gag caa aaa tgt aaa aaa gta aaa ttt agt tgc gtg aat tcg tgc      243
Pro Glu Gln Lys Cys Lys Lys Val Lys Phe Ser Cys Val Asn Ser Cys
 60                  65                  70                  75 agt tca ccc gaa atg cag tat tgt ccg gaa ata gga gca gat ccg gtt      291
Ser Ser Pro Glu Met Gln Tyr Cys Pro Glu Ile Gly Ala Asp Pro Val
                 80                  85                  90 aag gaa tcc tgt agc cca gat caa gtg tgc gct gat caa agt gga tat      339
Lys Glu Ser Cys Ser Pro Asp Gln Val Cys Ala Asp Gln Ser Gly Tyr
             95                 100                 105 cta cag tgc acc act aaa gaa agt aca gtc tgc aaa gta caa ggt ttc      387
Leu Gln Cys Thr Thr Lys Glu Ser Thr Val Cys Lys Val Gln Gly Phe
        110                 115                 120 aaa tgt ccg tca cca tcg aga ttt tat cca aat ata aat gat tgt caa      435
Lys Cys Pro Ser Pro Ser Arg Phe Tyr Pro Asn Ile Asn Asp Cys Gln
    125                 130                 135 agc tat tat tat tgt gac gaa aat agt ata gga acc caa tat tat tgc      483
Ser Tyr Tyr Tyr Cys Asp Glu Asn Ser Ile Gly Thr Gln Tyr Tyr Cys
140                 145                 150                 155 ccc gca aat ttt gca tat gat ccg tta cgt cat aat tgc gga cct atg      531
Pro Ala Asn Phe Ala Tyr Asp Pro Leu Arg His Asn Cys Gly Pro Met
                160                 165                 170 gct ctg ggc aca aaa tgc tat aca gtt aca tgt cct gca cag cct aag      579
Ala Leu Gly Thr Lys Cys Tyr Thr Val Thr Cys Pro Ala Gln Pro Lys
            175                 180                 185 gtg ctt ccg tac att ggt gat aaa tca ttg tac gtc gta tgt atg gcc      627
Val Leu Pro Tyr Ile Gly Asp Lys Ser Leu Tyr Val Val Cys Met Ala
        190                 195                 200 gga aga gga acc gta ttg caa tgc gaa gaa ccc gcc gag ttt tcc cca      675
Gly Arg Gly Thr Val Leu Gln Cys Glu Glu Pro Ala Glu Phe Ser Pro
    205                 210                 215 agg agc gaa acc tgt gtc ggg caa tgc cga gca cgt gga aaa ttt gct      723
Arg Ser Glu Thr Cys Val Gly Gln Cys Arg Ala Arg Gly Lys Phe Ala
220                 225                 230                 235 ttc aag aac gac gca aca tgc cgg aag ttc ttc acg tgt tta cgt cct      771
Phe Lys Asn Asp Ala Thr Cys Arg Lys Phe Phe Thr Cys Leu Arg Pro
                240                 245                 250
```

-continued

```
aaa gga gag cca gtt cct gat caa tgt ccg att gga aca gta ttt aac    819
Lys Gly Glu Pro Val Pro Asp Gln Cys Pro Ile Gly Thr Val Phe Asn
        255                 260                 265 caa gct act caa agc tgc aac aca gga act tgc gag agg aaa cct aaa    867
Gln Ala Thr Gln Ser Cys Asn Thr Gly Thr Cys Glu Arg Lys Pro Lys
            270                 275                 280 tta tat taatatattg atgaagtatt caacaaaaga aactatacaa aatatgtact     923
Leu Tyr
    285 ttgttttact ttatgtgtta tataaaaaaa tattatggtt gaacacaggc tcgcaaatat  983 gataaggcat ttaagaattt tacaatttag attttttaa atccatgaat atatttgttc   1043 taatc                                                              1048

<210> SEQ ID NO 26
<211> LENGTH: 285
<212> TYPE: PRT
<213> ORGANISM: Ctenocephalides felis

<400> SEQUENCE: 26

Met Phe Tyr Ile Thr Leu Val Phe Ile Ser Phe Val Ala Leu Ser Val
1               5                   10                  15

Val Thr Ala Tyr Asp Gly Glu Phe Asn Val Asp Gly Thr Pro Leu Thr
            20                  25                  30

Val Asn Lys Glu Val Phe Ala Ser Leu Asp Glu Pro Ala Pro Gly Val
        35                  40                  45

Val Pro Thr Pro Glu Pro Thr Pro Val Pro Lys Pro Glu Gln Lys Cys
    50                  55                  60

Lys Lys Val Lys Phe Ser Cys Val Asn Ser Cys Ser Ser Pro Glu Met
65                  70                  75                  80

Gln Tyr Cys Pro Glu Ile Gly Ala Asp Pro Val Lys Glu Ser Cys Ser
                85                  90                  95

Pro Asp Gln Val Cys Ala Asp Gln Ser Gly Tyr Leu Gln Cys Thr Thr
            100                 105                 110

Lys Glu Ser Thr Val Cys Lys Val Gln Gly Phe Lys Cys Pro Ser Pro
        115                 120                 125

Ser Arg Phe Tyr Pro Asn Ile Asn Asp Cys Gln Ser Tyr Tyr Tyr Cys
    130                 135                 140

Asp Glu Asn Ser Ile Gly Thr Gln Tyr Tyr Cys Pro Ala Asn Phe Ala
145                 150                 155                 160

Tyr Asp Pro Leu Arg His Asn Cys Gly Pro Met Ala Leu Gly Thr Lys
                165                 170                 175

Cys Tyr Thr Val Thr Cys Pro Ala Gln Pro Lys Val Leu Pro Tyr Ile
            180                 185                 190

Gly Asp Lys Ser Leu Tyr Val Val Cys Met Ala Gly Arg Gly Thr Val
        195                 200                 205

Leu Gln Cys Glu Glu Pro Ala Glu Phe Ser Pro Arg Ser Glu Thr Cys
    210                 215                 220

Val Gly Gln Cys Arg Ala Arg Gly Lys Phe Ala Phe Lys Asn Asp Ala
225                 230                 235                 240

Thr Cys Arg Lys Phe Phe Thr Cys Leu Arg Pro Lys Gly Glu Pro Val
                245                 250                 255

Pro Asp Gln Cys Pro Ile Gly Thr Val Phe Asn Gln Ala Thr Gln Ser
            260                 265                 270

Cys Asn Thr Gly Thr Cys Glu Arg Lys Pro Lys Leu Tyr
        275                 280                 285
```

<210> SEQ ID NO 27
<211> LENGTH: 1048
<212> TYPE: DNA
<213> ORGANISM: Ctenocephalides felis

<400> SEQUENCE: 27

| | | | | | |
|---|---|---|---|---|---|
| gattagaaca | aatatattca | tggatttaaa | aaaatctaaa | ttgtaaaatt | cttaaatgcc | 60 |
| ttatcatatt | tgcgagcctg | tgttcaacca | taatatttt | ttatataaca | cataaagtaa | 120 |
| aacaaagtac | atattttgta | tagtttcttt | tgttgaatac | ttcatcaata | tattaatata | 180 |
| atttaggttt | cctctcgcaa | gttcctgtgt | tgcagctttg | agtagcttgg | ttaaatactg | 240 |
| ttccaatcgg | acattgatca | ggaactggct | ctcctttagg | acgtaaacac | gtgaagaact | 300 |
| tccggcatgt | tgcgtcgttc | ttgaaagcaa | attttccacg | tgctcggcat | tgcccgacac | 360 |
| aggtttcgct | ccttggggaa | aactcggcgg | gttcttcgca | ttgcaatacg | gttcctcttc | 420 |
| cggccataca | tacgacgtac | aatgatttat | caccaatgta | cggaagcacc | ttaggctgtg | 480 |
| caggacatgt | aactgtatag | cattttgtgc | ccagagccat | aggtccgcaa | ttatgacgta | 540 |
| acggatcata | tgcaaaattt | gcggggcaat | aatattgggt | tcctatacta | ttttcgtcac | 600 |
| aataataata | gctttgacaa | tcatttatat | ttggataaaa | tctcgatggt | gacggacatt | 660 |
| tgaaaccttg | tactttgcag | actgtacttt | ctttagtggt | gcactgtaga | tatccacttt | 720 |
| gatcagcgca | cacttgatct | gggctacagg | attccttaac | cggatctgct | cctatttccg | 780 |
| gacaatactg | catttcgggt | gaactgcacg | aattcacgca | actaaatttt | acttttttac | 840 |
| atttttgctc | gggtttcggt | acaggtgtag | gttcaggagt | aggtactact | cctggtgcgg | 900 |
| gctcatccaa | tgatgcaaat | acttctttat | ttactgttaa | aggcgttccg | tcgacattaa | 960 |
| actcaccatc | ataagcggta | acgacagata | acgccacaaa | actaataaaa | accaatgtga | 1020 |
| tataaaacat | tcttaataaa | tatgttac | | | | 1048 |

<210> SEQ ID NO 28
<211> LENGTH: 855
<212> TYPE: DNA
<213> ORGANISM: Ctenocephalides felis

<400> SEQUENCE: 28

| | | | | | |
|---|---|---|---|---|---|
| atgttttata | tcacattggt | ttttattagt | tttgtggcgt | tatctgtcgt | taccgcttat | 60 |
| gatggtgagt | ttaatgtcga | cggaacgcct | ttaacagtaa | ataaagaagt | atttgcatca | 120 |
| ttggatgagc | ccgcaccagg | agtagtacct | actcctgaac | ctacacctgt | accgaaaccc | 180 |
| gagcaaaaat | gtaaaaaagt | aaaatttagt | tgcgtgaatt | cgtgcagttc | acccgaaatg | 240 |
| cagtattgtc | cggaaatagg | agcagatccg | gttaaggaat | cctgtagccc | agatcaagtg | 300 |
| tgcgctgatc | aaagtggata | tctacagtgc | accactaaag | aaagtacagt | ctgcaaagta | 360 |
| caaggtttca | aatgtccgtc | accatcgaga | ttttatccaa | atataaatga | ttgtcaaagc | 420 |
| tattattatt | gtgacgaaaa | tagtatagga | acccaatatt | attgccccgc | aaattttgca | 480 |
| tatgatccgt | tacgtcataa | ttgcggacct | atggctctgg | gcacaaaatg | ctatacagtt | 540 |
| acatgtcctg | cacagcctaa | ggtgcttccg | tacattggtg | ataaatcatt | gtacgtcgta | 600 |
| tgtatggccg | gaagaggaac | cgtattgcaa | tgcgaagaac | ccgccgagtt | tccccaaggg | 660 |
| agcgaaacct | gtgtcgggca | atgccgagca | cgtggaaaat | ttgctttcaa | gaacgacgca | 720 |
| acatgccgga | agttcttcac | gtgtttacgt | cctaaaggag | agccagttcc | tgatcaatgt | 780 |

-continued

```
ccgattggaa cagtatttaa ccaagctact caaagctgca acacaggaac ttgcgagagg    840
aaacctaaat tatat                                                    855

<210> SEQ ID NO 29
<211> LENGTH: 855
<212> TYPE: DNA
<213> ORGANISM: Ctenocephalides felis

<400> SEQUENCE: 29
atataattta ggtttcctct cgcaagttcc tgtgttgcag ctttgagtag cttggttaaa     60
tactgttcca atcggacatt gatcaggaac tggctctcct ttaggacgta aacacgtgaa    120
gaacttccgg catgttgcgt cgttcttgaa agcaaatttt ccacgtgctc ggcattgccc    180
gacacaggtt tcgctccttg gggaaaactc ggcgggttct tcgcattgca atacggttcc    240
tcttccggcc atacatacga cgtacaatga tttatcacca atgtacggaa gcaccttagg    300
ctgtgcagga catgtaactg tatagcattt tgtgcccaga gccataggtc cgcaattatg    360
acgtaacgga tcatatgcaa aatttgcggg gcaataatat tgggttccta tactattttc    420
gtcacaataa taatagcttt gacaatcatt tatatttgga taaaatctcg atggtgacgg    480
acatttgaaa ccttgtactt tgcagactgt actttcttta gtggtgcact gtagatatcc    540
actttgatca gcgcacactt gatctgggct acaggattcc ttaaccggat ctgctcctat    600
ttccggacaa tactgcattt cgggtgaact gcacgaattc acgcaactaa attttacttt    660
tttacatttt tgctcgggtt tcggtacagg tgtaggttca ggagtaggta ctactcctgg    720
tgcgggctca tccaatgatg caaatacttc tttatttact gttaaaggcg ttccgtcgac    780
attaaactca ccatcataag cggtaacgac agataacgcc acaaaactaa taaaaaccaa    840
tgtgatataa aacat                                                    855

<210> SEQ ID NO 30
<211> LENGTH: 802
<212> TYPE: DNA
<213> ORGANISM: Ctenocephalides felis
<220> FEATURE:
<221> NAME/KEY: CDS
<222> LOCATION: (2)..(799)
<223> OTHER INFORMATION:

<400> SEQUENCE: 30 t tat gat ggt gag ttt aat gtc gac gga acg cct tta aca gta aat aaa     49
  Tyr Asp Gly Glu Phe Asn Val Asp Gly Thr Pro Leu Thr Val Asn Lys
  1               5                  10                  15 gaa gta ttt gca tca ttg gat gag ccc gca cca gga gta gta cct act       97
Glu Val Phe Ala Ser Leu Asp Glu Pro Ala Pro Gly Val Val Pro Thr
             20                  25                  30 cct gaa cct aca cct gta ccg aaa ccc gag caa aaa tgt aaa aaa gta      145
Pro Glu Pro Thr Pro Val Pro Lys Pro Glu Gln Lys Cys Lys Lys Val
         35                  40                  45 aaa ttt agt tgc gtg aat tcg tgc agt tca ccc gaa atg cag tat tgt      193
Lys Phe Ser Cys Val Asn Ser Cys Ser Ser Pro Glu Met Gln Tyr Cys
 50                  55                  60 ccg gaa ata gga gca gat ccg gtt aag gaa tcc tgt agc cca gat caa      241
Pro Glu Ile Gly Ala Asp Pro Val Lys Glu Ser Cys Ser Pro Asp Gln
 65                  70                  75                  80 gtg tgc gct gat caa agt gga tat cta cag tgc acc act aaa gaa agt      289
Val Cys Ala Asp Gln Ser Gly Tyr Leu Gln Cys Thr Thr Lys Glu Ser
             85                  90                  95
```

| | | |
|---|---|---|
| aca gtc tgc aaa gta caa ggt ttc aaa tgt ccg tca cca tcg aga ttt<br>Thr Val Cys Lys Val Gln Gly Phe Lys Cys Pro Ser Pro Ser Arg Phe<br>100                        105                      110 | | 337 |
| tat cca aat ata aat gat tgt caa agc tat tat tat tgt gac gaa aat<br>Tyr Pro Asn Ile Asn Asp Cys Gln Ser Tyr Tyr Tyr Cys Asp Glu Asn<br>            115                      120                      125 | | 385 |
| agt ata gga acc caa tat tat tgc ccc gca aat ttt gca tat gat ccg<br>Ser Ile Gly Thr Gln Tyr Tyr Cys Pro Ala Asn Phe Ala Tyr Asp Pro<br>130                        135                      140 | | 433 |
| tta cgt cat aat tgc gga cct atg gct ctg ggc aca aaa tgc tat aca<br>Leu Arg His Asn Cys Gly Pro Met Ala Leu Gly Thr Lys Cys Tyr Thr<br>145                        150                      155                      160 | | 481 |
| gtt aca tgt cct gca cag cct aag gtg ctt ccg tac att ggt gat aaa<br>Val Thr Cys Pro Ala Gln Pro Lys Val Leu Pro Tyr Ile Gly Asp Lys<br>            165                      170                      175 | | 529 |
| tca ttg tac gtc gta tgt atg gcc gga aga gga acc gta ttg caa tgc<br>Ser Leu Tyr Val Val Cys Met Ala Gly Arg Gly Thr Val Leu Gln Cys<br>            180                      185                      190 | | 577 |
| gaa gaa ccc gcc gag ttt tcc cca agg agc gaa acc tgt gtc ggg caa<br>Glu Glu Pro Ala Glu Phe Ser Pro Arg Ser Glu Thr Cys Val Gly Gln<br>            195                      200                      205 | | 625 |
| tgc cga gca cgt gga aaa ttt gct ttc aag aac gac gca aca tgc cgg<br>Cys Arg Ala Arg Gly Lys Phe Ala Phe Lys Asn Asp Ala Thr Cys Arg<br>210                        215                      220 | | 673 |
| aag ttc ttc acg tgt tta cgt cct aaa gga gag cca gtt cct gat caa<br>Lys Phe Phe Thr Cys Leu Arg Pro Lys Gly Glu Pro Val Pro Asp Gln<br>225                        230                      235                      240 | | 721 |
| tgt ccg att gga aca gta ttt aac caa gct act caa agc tgc aac aca<br>Cys Pro Ile Gly Thr Val Phe Asn Gln Ala Thr Gln Ser Cys Asn Thr<br>            245                      250                      255 | | 769 |
| gga act tgc gag agg aaa cct aaa tta tat taa<br>Gly Thr Cys Glu Arg Lys Pro Lys Leu Tyr<br>260                        265 | | 802 |

<210> SEQ ID NO 31
<211> LENGTH: 266
<212> TYPE: PRT
<213> ORGANISM: Ctenocephalides felis

<400> SEQUENCE: 31

Tyr Asp Gly Glu Phe Asn Val Asp Gly Thr Pro Leu Thr Val Asn Lys
1               5                   10                  15

Glu Val Phe Ala Ser Leu Asp Glu Pro Ala Pro Gly Val Val Pro Thr
            20                  25                  30

Pro Glu Pro Thr Pro Val Pro Lys Pro Glu Gln Lys Cys Lys Lys Val
        35                  40                  45

Lys Phe Ser Cys Val Asn Ser Cys Ser Ser Pro Glu Met Gln Tyr Cys
    50                  55                  60

Pro Glu Ile Gly Ala Asp Pro Val Lys Glu Ser Cys Ser Pro Asp Gln
65                  70                  75                  80

Val Cys Ala Asp Gln Ser Gly Tyr Leu Gln Cys Thr Thr Lys Glu Ser
                85                  90                  95

Thr Val Cys Lys Val Gln Gly Phe Lys Cys Pro Ser Pro Ser Arg Phe
            100                 105                 110

Tyr Pro Asn Ile Asn Asp Cys Gln Ser Tyr Tyr Tyr Cys Asp Glu Asn
        115                 120                 125

Ser Ile Gly Thr Gln Tyr Tyr Cys Pro Ala Asn Phe Ala Tyr Asp Pro
    130                 135                 140

```
Leu Arg His Asn Cys Gly Pro Met Ala Leu Gly Thr Lys Cys Tyr Thr
145                 150                 155                 160

Val Thr Cys Pro Ala Gln Pro Lys Val Leu Pro Tyr Ile Gly Asp Lys
                165                 170                 175

Ser Leu Tyr Val Val Cys Met Ala Gly Arg Gly Thr Val Leu Gln Cys
            180                 185                 190

Glu Glu Pro Ala Glu Phe Ser Pro Arg Ser Glu Thr Cys Val Gly Gln
        195                 200                 205

Cys Arg Ala Arg Gly Lys Phe Ala Phe Lys Asn Asp Ala Thr Cys Arg
    210                 215                 220

Lys Phe Phe Thr Cys Leu Arg Pro Lys Gly Glu Pro Val Pro Asp Gln
225                 230                 235                 240

Cys Pro Ile Gly Thr Val Phe Asn Gln Ala Thr Gln Ser Cys Asn Thr
                245                 250                 255

Gly Thr Cys Glu Arg Lys Pro Lys Leu Tyr
            260                 265
```

<210> SEQ ID NO 32
<211> LENGTH: 802
<212> TYPE: DNA
<213> ORGANISM: Ctenocephalides felis

<400> SEQUENCE: 32

```
ttaatataat ttaggtttcc tctcgcaagt tcctgtgttg cagcttttgag tagcttggtt      60
aaatactgtt ccaatcggac attgatcagg aactggctct cctttaggac gtaaacacgt     120
gaagaacttc cggcatgttg cgtcgttctt gaaagcaaat tttccacgtg ctcggcattg     180
cccgacacag gtttcgctcc ttggggaaaa ctcggcgggt tcttcgcatt gcaatacggt     240
tcctcttccg gccatacata cgacgtacaa tgatttatca ccaatgtacg gaagcacctt     300
aggctgtgca ggacatgtaa ctgtatagca ttttgtgccc agagccatag gtccgcaatt     360
atgacgtaac ggatcatatg caaaatttgc ggggcaataa tattgggttc ctatactatt     420
ttcgtcacaa taataatagc tttgacaatc atttatattt ggataaaatc tcgatggtga     480
cggacatttg aaaccttgta ctttgcagac tgtactttct ttagtggtgc actgtagata     540
tccactttga tcagcgcaca cttgatctgg gctacaggat tccttaaccg gatctgctcc     600
tatttccgga caatactgca tttcgggtga actgcacgaa ttcacgcaac taaattttac     660
ttttttacat ttttgctcgg gtttcggtac aggtgtaggt tcaggagtag gtactactcc     720
tggtgcgggc tcatccaatg atgcaaatac ttctttattt actgttaaag gcgttccgtc     780
gacattaaac tcaccatcat aa                                              802
```

<210> SEQ ID NO 33
<211> LENGTH: 436
<212> TYPE: DNA
<213> ORGANISM: Ctenocephalides felis
<220> FEATURE:
<221> NAME/KEY: misc_feature
<222> LOCATION: (347)..(347)
<223> OTHER INFORMATION: n = unknown

<400> SEQUENCE: 33

```
cttgtatata agtgagtttt accaaagatg tgtgggccct acatattcgg aatgtttaat      60
tacacctctg cctcctccaa ttgttccgac tactacgact acgacaacta caccagcacc     120
gccgcctctt ttttcatgcg tgcaggaagg gatgtttata gatccctatg acagcacttg     180
caaaggatac tacaaatgtg ctttgaaagc aggcggagga ttcagtgtag cgcgttacaa     240
```

-continued

| | |
|---|---|
| ttgtcctggt tctacttact tcagcagcac gtatcagcaa tgtgtggtcg cttcccttc | 300 |
| ggagtgccta agaaatcctc cagcgccttg gcaaccacct acgccgncgc catatacaac | 360 |
| tgcgtgcaga gcggtcattt gcagatccag cagacaaaac atgcaaagta tattttgaat | 420 |
| gtgtgagact ctctgg | 436 |

<210> SEQ ID NO 34
<211> LENGTH: 485
<212> TYPE: DNA
<213> ORGANISM: Ctenocephalides felis

<400> SEQUENCE: 34

| | |
|---|---|
| ctcatttgca gatccagcag acaaaacatg caaagtatat tttgaatgtg tgagactctc | 60 |
| tggaggaaat ttcaacgtgg gtcgttttac atgcgccgga cagacatact tcagcgcgct | 120 |
| ttaccaacaa tgcgtgcaag cgcctttatc cgagtgcttg gcgacagctg cacctccacc | 180 |
| accgccacca ggaccaggac catcgcaacc ctttgcttgc gtgcggacag gattgttttt | 240 |
| ggattacact gataattctt gcaaatggta ctacgagtgc acattaaacg ctcaaggtgt | 300 |
| attcgacgtg gcccgatatg cttgtgcagc tgagttatat ttcaacagcg ttctgcagca | 360 |
| gtgcgtacct gcataccagt cagactgttt aggtgcaagt gtcacttctt cccatcatac | 420 |
| catccttacc atcttaccat ctttccaacc ttgcaacatc ttcccaacag caggattctt | 480 |
| ttggc | 485 |

<210> SEQ ID NO 35
<211> LENGTH: 550
<212> TYPE: DNA
<213> ORGANISM: Ctenocephalides felis

<400> SEQUENCE: 35

| | |
|---|---|
| gtcgttttac atgcgccgga cagacatact tcagcgcgct ttaccaacaa tgcgtgcaag | 60 |
| cgcctttatc cgagtgcttg gcgacagctg cacctccacc accgccacca ggaccaggac | 120 |
| catcgcaacc ctttgcttgc gtgcggacag gattgttttt ggattacact gataattctt | 180 |
| gcaaatggta ctacgagtgc acattaaacg ctcaaggtgt attcgacgtg gcccgatatg | 240 |
| cttgtgcagc tgagttatat ttcaacagcg ttctgcagca gtgcgtacct gcataccagt | 300 |
| cagactgttt aggtgcaagt gtcacttctt ccccatccat accatcctta ccatccttac | 360 |
| catctttccc aaccttgcca acatcttccc aacagcagg atttccttt ggccgaaaat | 420 |
| ctcttgatat gcaaacaaaa actggaacta atgtacaaa aggagaagtt tctaaagacg | 480 |
| attaaattct acatgtccta gtgagtgtgt atatgaaatg ctattgatat acatcaagct | 540 |
| tataaggtat | 550 |

<210> SEQ ID NO 36
<211> LENGTH: 436
<212> TYPE: DNA
<213> ORGANISM: Ctenocephalides felis

<400> SEQUENCE: 36

| | |
|---|---|
| taccatcttt cccaaccttg ccaacatctt ccccaacagc aggattcct tttgaccgaa | 60 |
| aatctcttga tatgcaaaca aaaactggaa ctaaatgtac aaaaggagaa gtttctaaag | 120 |
| acgatttaaa ttctacatgt acctagtgag tgtgttatat gaaattgcta ttgcatatta | 180 |
| catacaagct taataaaggt tatggtgatt tatttcattt aaaggcaatg tatcggttta | 240 |
| atggttttaa atttatttt tatttaatat taaatagatt aattaaaaat ctataaagtg | 300 |

-continued

```
ataagaggcc tgatatccat aatattattg aatattaaga agtgacggat agatctgata      360
atgtagtagt tggtatagac aatttactta ataattatga gtggcatcat tatgcaatga      420
tttatcacta ttattt                                                     436
```

```
<210> SEQ ID NO 37
<211> LENGTH: 498
<212> TYPE: DNA
<213> ORGANISM: Ctenocephalides felis
<220> FEATURE:
<221> NAME/KEY: misc_feature
<222> LOCATION: (23)..(23)
<223> OTHER INFORMATION: n = unknown
<220> FEATURE:
<221> NAME/KEY: misc_feature
<222> LOCATION: (30)..(30)
<223> OTHER INFORMATION: n = unknown
<220> FEATURE:
<221> NAME/KEY: misc_feature
<222> LOCATION: (33)..(33)
<223> OTHER INFORMATION: n = unknown
<220> FEATURE:
<221> NAME/KEY: misc_feature
<222> LOCATION: (55)..(55)
<223> OTHER INFORMATION: n = unknown
<220> FEATURE:
<221> NAME/KEY: misc_feature
<222> LOCATION: (130)..(130)
<223> OTHER INFORMATION: n = unknown
<220> FEATURE:
<221> NAME/KEY: misc_feature
<222> LOCATION: (138)..(138)
<223> OTHER INFORMATION: n = unknown
<220> FEATURE:
<221> NAME/KEY: misc_feature
<222> LOCATION: (147)..(148)
<223> OTHER INFORMATION: n = unknown
<220> FEATURE:
<221> NAME/KEY: misc_feature
<222> LOCATION: (154)..(154)
<223> OTHER INFORMATION: n = unknown
<220> FEATURE:
<221> NAME/KEY: misc_feature
<222> LOCATION: (158)..(158)
<223> OTHER INFORMATION: n = unknown
<220> FEATURE:
<221> NAME/KEY: misc_feature
<222> LOCATION: (383)..(383)
<223> OTHER INFORMATION: n = unknown
<220> FEATURE:
<221> NAME/KEY: misc_feature
<222> LOCATION: (457)..(457)
<223> OTHER INFORMATION: n = unknown

<400> SEQUENCE: 37
aaaaggagaa gtttctaaag acnattttn ttntacatgt acctagtgag tgtgnggggg       60
ggaaattgct attgcatatt acatacaagc ttaataaagg ttatggtgat ttatttcatt    120
taaaggcaan gtatcggntt aatggcnnta aatntatntt ttatttaata ttaaatagat    180
taattaaaaa tctataaagt gataagaggc ctgatatcca taatattatt gaatattaag    240
aagtgacgga tagatctgat aatgtagtag ttgttataga caatttactt aataattatg    300
agttgcatca ttatgcaatg atttatcact attatttatt caacatttta tttaactgct    360
tgcaactttt aataaaacgc atnttttatt gttttaagta taaatcttat tagggcacaa    420
tatgaaaata aaaataaaga actttataca aaagctnttt tatcaatatg cttcttgcgc    480
tattaagtta agaaattt                                                    498
```

```
<210> SEQ ID NO 38
<211> LENGTH: 436
<212> TYPE: DNA
<213> ORGANISM: Ctenocephalides felis
<220> FEATURE:
<221> NAME/KEY: misc_feature
<222> LOCATION: (64)..(64)
<223> OTHER INFORMATION: n = unknown
<220> FEATURE:
<221> NAME/KEY: misc_feature
<222> LOCATION: (86)..(86)
<223> OTHER INFORMATION: n = unknown
<220> FEATURE:
<221> NAME/KEY: misc_feature
<222> LOCATION: (175)..(175)
<223> OTHER INFORMATION: n = unknown
<220> FEATURE:
<221> NAME/KEY: misc_feature
<222> LOCATION: (360)..(360)
<223> OTHER INFORMATION: n = unknown
<220> FEATURE:
<221> NAME/KEY: misc_feature
<222> LOCATION: (385)..(385)
<223> OTHER INFORMATION: n = unknown
<220> FEATURE:
<221> NAME/KEY: misc_feature
<222> LOCATION: (390)..(390)
<223> OTHER INFORMATION: n = unknown
<220> FEATURE:
<221> NAME/KEY: misc_feature
<222> LOCATION: (429)..(429)
<223> OTHER INFORMATION: n = unknown

<400> SEQUENCE: 38
aataaaattt cttaacttaa tagcgcaaga agcatattgt ataaaaaaag cttttgttaa      60
aggncttatt tttattttca tattgngccc taataagatt tatacttaaa acaataaaaa     120
atgcgtttta ttaaaagttg caagcagtta aataaaatgt tgaataaaata atagngataa    180 atcattgcat aatgatgcaa ctcataatta ttaagtaaat tggctataac aactactaca    240
ttatcagatc tatccgtcac ttcttaatat tcaataatat tatggatatc aggcctctta   300
tcactttata gatttttaat taatctattt aatattaaat aaaaaataaa ttttaaaccn   360
tttaaccgat ccattgcctt taaangaaan aaataccata acctttatta agcttgttgt   420
aatatgcant agcaat                                                   436

<210> SEQ ID NO 39
<211> LENGTH: 1513
<212> TYPE: DNA
<213> ORGANISM: Ctenocephalides felis
<220> FEATURE:
<221> NAME/KEY: CDS
<222> LOCATION: (1)..(1017)
<223> OTHER INFORMATION:
<220> FEATURE:
<221> NAME/KEY: misc_feature
<222> LOCATION: (1356)..(1356)
<223> OTHER INFORMATION: n = unknown
<220> FEATURE:
<221> NAME/KEY: misc_feature
<222> LOCATION: (1430)..(1430)
<223> OTHER INFORMATION: n = unknown
<220> FEATURE:
<221> NAME/KEY: misc_feature
<222> LOCATION: (1491)..(1491)
<223> OTHER INFORMATION: n = unknown
<220> FEATURE:
<221> NAME/KEY: misc_feature
<222> LOCATION: (1495)..(1495)
<223> OTHER INFORMATION: n = unknown
```

<400> SEQUENCE: 39

```
tac aag tgc aaa ctt ggt cta aat ggt gct ctg caa agc ggt cat ttt      48
Tyr Lys Cys Lys Leu Gly Leu Asn Gly Ala Leu Gln Ser Gly His Phe
1               5                   10                  15 tta tgc cca tgg aac ttg tat ata agt gag ttt tac caa aga tgt gtg      96
Leu Cys Pro Trp Asn Leu Tyr Ile Ser Glu Phe Tyr Gln Arg Cys Val
            20                  25                  30 ggc cct aca tat tcg gaa tgt tta att aca cct ctg cct cct cca att     144
Gly Pro Thr Tyr Ser Glu Cys Leu Ile Thr Pro Leu Pro Pro Pro Ile
        35                  40                  45 gtt ccg act act acg act acg aca act aca cca gca ccg ccg cct ctt     192
Val Pro Thr Thr Thr Thr Thr Thr Thr Thr Pro Ala Pro Pro Pro Leu
    50                  55                  60 ttt tca tgc gtg cag gaa ggg atg ttt ata gat ccc tat gac agc act     240
Phe Ser Cys Val Gln Glu Gly Met Phe Ile Asp Pro Tyr Asp Ser Thr
65                  70                  75                  80 tgc aaa gga tac tac aaa tgt gct ttg aaa gca ggc gga gga ttc agt     288
Cys Lys Gly Tyr Tyr Lys Cys Ala Leu Lys Ala Gly Gly Gly Phe Ser
                85                  90                  95 gta gcg cgt tac aat tgt cct ggt tct act tac ttc agc agc acg tat     336
Val Ala Arg Tyr Asn Cys Pro Gly Ser Thr Tyr Phe Ser Ser Thr Tyr
            100                 105                 110 cag caa tgt gtg gtc gct tcc ctt tcg gag tgc cta aga aat cct cca     384
Gln Gln Cys Val Val Ala Ser Leu Ser Glu Cys Leu Arg Asn Pro Pro
        115                 120                 125 gcg cct tgg caa cca cct acg ccg ccg ccc ata tac aac tgc gtg cag     432
Ala Pro Trp Gln Pro Pro Thr Pro Pro Pro Ile Tyr Asn Cys Val Gln
    130                 135                 140 agc ggc tca ttt gca gat cca gca gac aaa aca tgc aaa gta tat ttt     480
Ser Gly Ser Phe Ala Asp Pro Ala Asp Lys Thr Cys Lys Val Tyr Phe
145                 150                 155                 160 gaa tgt gtg aga ctc tct gga gga aat ttc aac gtg ggt cgt ttt aca     528
Glu Cys Val Arg Leu Ser Gly Gly Asn Phe Asn Val Gly Arg Phe Thr
                165                 170                 175 tgc gcc gga cag aca tac ttc agc gcg ctt tac caa caa tgc gtg caa     576
Cys Ala Gly Gln Thr Tyr Phe Ser Ala Leu Tyr Gln Gln Cys Val Gln
            180                 185                 190 gcg cct tta tcc gag tgc ttg gcg aca gct gca cct cca cca ccg cca     624
Ala Pro Leu Ser Glu Cys Leu Ala Thr Ala Ala Pro Pro Pro Pro Pro
        195                 200                 205 cca gga cca gga cca tcg caa ccc ttt gct tgc gtg cgg aca gga ttg     672
Pro Gly Pro Gly Pro Ser Gln Pro Phe Ala Cys Val Arg Thr Gly Leu
    210                 215                 220 ttt ttg gat tac act gat aat tct tgc aaa tgg tac tac gag tgc aca     720
Phe Leu Asp Tyr Thr Asp Asn Ser Cys Lys Trp Tyr Tyr Glu Cys Thr
225                 230                 235                 240 tta aac gct caa ggt gta ttc gac gtg gcc cga tat gct tgt gca gct     768
Leu Asn Ala Gln Gly Val Phe Asp Val Ala Arg Tyr Ala Cys Ala Ala
                245                 250                 255 gag tta tat ttc aac agc gtt ctg cag cag tgc gta cct gca tac cag     816
Glu Leu Tyr Phe Asn Ser Val Leu Gln Gln Cys Val Pro Ala Tyr Gln
            260                 265                 270 tca gac tgt tta ggt gca agt gtc act tct tcc cca tcc ata cca tcc     864
Ser Asp Cys Leu Gly Ala Ser Val Thr Ser Ser Pro Ser Ile Pro Ser
        275                 280                 285 tta cca tcc tta cca tct ttc cca acc ttg cca aca tct tcc cca aca     912
Leu Pro Ser Leu Pro Ser Phe Pro Thr Leu Pro Thr Ser Ser Pro Thr
    290                 295                 300
```

```
gca gga ttt cct ttt ggc cga aaa tct ctt gat atg caa aca aaa act    960
Ala Gly Phe Pro Phe Gly Arg Lys Ser Leu Asp Met Gln Thr Lys Thr
305                 310                 315                 320 gga act aaa tgt aca aaa gga gaa gtt tct aaa gac gat tta aat tct   1008
Gly Thr Lys Cys Thr Lys Gly Glu Val Ser Lys Asp Asp Leu Asn Ser
                325                 330                 335 aca tgt acc tagtgagtgt gttatatgaa attgctattg catattcat            1057
Thr Cys Thr acaagcttaa taaaggttat ggtgatttat ttcatttaaa ggcaatgtat cggtttaatg  1117
gttttaaatt tatttttat ttaatattaa atagattaat taaaaatcta taagtgata   1177 agaggcctga tatccataat attattgaat attaagaagt gacggataga tctgataatg  1237
tagtagttgg tatagacaat ttacttaata attatgagtg gcatcattat gcaatgattt  1297
atcactatta tttattcaac attttattta actgcttgca acttttaata aaacgcatnt  1357
tttattgttt taagtataaa tcttattagg gcacaatatg aaaataaaaa taagaacttt  1417
tatacaaaag ctnttttatc aatatgcttc ttgcgctatt aagttaagaa attttattta  1477
tgctgggaaa aaancaanaa atgctttatt tattct                           1513
```

<210> SEQ ID NO 40
<211> LENGTH: 339
<212> TYPE: PRT
<213> ORGANISM: Ctenocephalides felis

<400> SEQUENCE: 40

```
Tyr Lys Cys Lys Leu Gly Leu Asn Gly Ala Leu Gln Ser Gly His Phe
1               5                   10                  15

Leu Cys Pro Trp Asn Leu Tyr Ile Ser Glu Phe Tyr Gln Arg Cys Val
            20                  25                  30

Gly Pro Thr Tyr Ser Glu Cys Leu Ile Thr Pro Leu Pro Pro Pro Ile
        35                  40                  45

Val Pro Thr Thr Thr Thr Thr Thr Thr Pro Ala Pro Pro Pro Leu
    50                  55                  60

Phe Ser Cys Val Gln Glu Gly Met Phe Ile Asp Pro Tyr Asp Ser Thr
65                  70                  75                  80

Cys Lys Gly Tyr Tyr Lys Cys Ala Leu Lys Ala Gly Gly Phe Ser
                85                  90                  95

Val Ala Arg Tyr Asn Cys Pro Gly Ser Thr Tyr Phe Ser Ser Thr Tyr
            100                 105                 110

Gln Gln Cys Val Val Ala Ser Leu Ser Glu Cys Leu Arg Asn Pro Pro
        115                 120                 125

Ala Pro Trp Gln Pro Pro Thr Pro Pro Ile Tyr Asn Cys Val Gln
    130                 135                 140

Ser Gly Ser Phe Ala Asp Pro Ala Asp Lys Thr Cys Lys Val Tyr Phe
145                 150                 155                 160

Glu Cys Val Arg Leu Ser Gly Gly Asn Phe Asn Val Gly Arg Phe Thr
                165                 170                 175

Cys Ala Gly Gln Thr Tyr Phe Ser Ala Leu Tyr Gln Gln Cys Val Gln
            180                 185                 190

Ala Pro Leu Ser Glu Cys Leu Thr Ala Ala Pro Pro Pro Pro
        195                 200                 205

Pro Gly Pro Gly Pro Ser Gln Pro Phe Ala Cys Val Arg Thr Gly Leu
    210                 215                 220

Phe Leu Asp Tyr Thr Asp Asn Ser Cys Lys Trp Tyr Tyr Glu Cys Thr
225                 230                 235                 240
```

```
Leu Asn Ala Gln Gly Val Phe Asp Val Ala Arg Tyr Ala Cys Ala Ala
                245                 250                 255

Glu Leu Tyr Phe Asn Ser Val Leu Gln Gln Cys Val Pro Ala Tyr Gln
            260                 265                 270

Ser Asp Cys Leu Gly Ala Ser Val Thr Ser Ser Pro Ser Ile Pro Ser
        275                 280                 285

Leu Pro Ser Leu Pro Ser Phe Pro Thr Leu Pro Thr Ser Ser Pro Thr
    290                 295                 300

Ala Gly Phe Pro Phe Gly Arg Lys Ser Leu Asp Met Gln Thr Lys Thr
305                 310                 315                 320

Gly Thr Lys Cys Thr Lys Gly Glu Val Ser Lys Asp Asp Leu Asn Ser
                325                 330                 335

Thr Cys Thr

<210> SEQ ID NO 41
<211> LENGTH: 1513
<212> TYPE: DNA
<213> ORGANISM: Ctenocephalides felis
<220> FEATURE:
<221> NAME/KEY: misc_feature
<222> LOCATION: (19)..(19)
<223> OTHER INFORMATION: n = unknown
<220> FEATURE:
<221> NAME/KEY: misc_feature
<222> LOCATION: (23)..(23)
<223> OTHER INFORMATION: n = unknown
<220> FEATURE:
<221> NAME/KEY: misc_feature
<222> LOCATION: (84)..(84)
<223> OTHER INFORMATION: n = unknown
<220> FEATURE:
<221> NAME/KEY: misc_feature
<222> LOCATION: (158)..(158)
<223> OTHER INFORMATION: n = unknown

<400> SEQUENCE: 41
agaataaata aagcattttnt tgnttttttc ccagcataaa taaaatttct taacttaata     60
gcgcaagaag catattgata aaanagcttt tgtataaagt tctttatttt tattttcata    120
ttgtgcccta ataagattta tacttaaaac aataaaanat gcgttttatt aaaagttgca    180
agcagttaaa taaatgttg aataaataat agtgataaat cattgcataa tgatgccact     240
cataattatt aagtaaattg tctataccaa ctactacatt atcagatcta tccgtcactt    300
cttaatattc aataatatta tggatatcag gcctcttatc actttataga ttttttaatta   360
atctatttaa tattaaataa aaaataaatt taaaaccatt aaaccgatac attgccttta    420
aatgaaataa atcaccataa cctttattaa gcttgtatgt aatatgcaat agcaatttca    480
tataacacac tcactaggta catgtagaat ttaaatcgtc tttagaaact tctccttttg    540
tacatttagt tccagttttt gtttgcatat caagagattt tcggccaaaa ggaaatcctg    600
ctgttgggga agatgttggc aaggttggga aagatggtaa ggatggtaag gatggtatgg    660
atggggaaga agtgacactt gcacctaaac agtctgactg gtatgcaggt acgcactgct    720
gcagaacgct gttgaaatat aactcagctg cacaagcata tcgggccacg tcgaatacac    780
cttgagcgtt taatgtgcac tcgtagtacc atttgcaaga attatcagtg taatccaaaa    840
acaatcctgt ccgcacgcaa gcaaagggtt gcgatggtcc tggtcctggt ggcggtggtg    900
gaggtgcagc tgtcgccaag cactcggata aggcgcttg cacgcattgt tggtaaagcg     960
cgctgaagta tgtctgtccg gcgcatgtaa aacgaccccac gttgaaattt cctccagaga   1020
gtctcacaca ttcaaaatat actttgcatg ttttgtctgc tggatctgca aatgagccgc    1080
```

-continued

```
tctgcacgca gttgtatatg ggcggcggcg taggtggttg ccaaggcgct ggaggatttc    1140
ttaggcactc cgaaagggaa gcgaccacac attgctgata cgtgctgctg aagtaagtag    1200
aaccaggaca attgtaacgc gctacactga atcctccgcc tgctttcaaa gcacatttgt    1260
agtatccttt gcaagtgctg tcatagggat ctataaacat cccttcctgc acgcatgaaa    1320
aaagaggcgg cggtgctggt gtagttgtcg tagtcgtagt agtcggaaca attggaggag    1380
gcagaggtgt aattaaacat tccgaatatg tagggcccac acatctttgg taaaactcac    1440
ttatatacaa gttccatggg cataaaaaat gaccgctttg cagagcacca tttagaccaa    1500
gtttgcactt gta                                                       1513
```

<210> SEQ ID NO 42
<211> LENGTH: 1832
<212> TYPE: DNA
<213> ORGANISM: Ctenocephalides felis
<220> FEATURE:
<221> NAME/KEY: CDS
<222> LOCATION: (146)..(1336)
<223> OTHER INFORMATION:
<220> FEATURE:
<221> NAME/KEY: misc_feature
<222> LOCATION: (3)..(3)
<223> OTHER INFORMATION: n = unknown
<220> FEATURE:
<221> NAME/KEY: misc_feature
<222> LOCATION: (1675)..(1675)
<223> OTHER INFORMATION: n = unknown
<220> FEATURE:
<221> NAME/KEY: misc_feature
<222> LOCATION: (1749)..(1749)
<223> OTHER INFORMATION: n = unknown
<220> FEATURE:
<221> NAME/KEY: misc_feature
<222> LOCATION: (1810)..(1810)
<223> OTHER INFORMATION: n = unknown
<220> FEATURE:
<221> NAME/KEY: misc_feature
<222> LOCATION: (1814)..(1814)
<223> OTHER INFORMATION: n = unknown

<400> SEQUENCE: 42

```
tcnaatacga ctcactatag ggcaagcagt gggtaacaac gcagagtacg cggggggattt    60 agtaacttca aattttggt acaatatcat tatcaaaaaa attgtttatt ttaaagtgga    120
atctgttaaa tcgcgtttca ttacg atg aaa ctg ctt tta gtg ctc ttg gct    172
                             Met Lys Leu Leu Leu Val Leu Leu Ala
                             1               5 acc ttc tcg tgt aca ttg tct ttg gag tct caa gaa cta att cca gtt    220
Thr Phe Ser Cys Thr Leu Ser Leu Glu Ser Gln Glu Leu Ile Pro Val
10                  15                  20                  25 gaa aca aat tcc agc agc gtt cgt att tgg cag caa cca ttc att tgt    268
Glu Thr Asn Ser Ser Ser Val Arg Ile Trp Gln Gln Pro Phe Ile Cys
                30                  35                  40 cca aga gtt gga cta ttt cgc gat cca ttg gat cct aca tgc aaa agg    316
Pro Arg Val Gly Leu Phe Arg Asp Pro Leu Asp Pro Thr Cys Lys Arg
            45                  50                  55 tac tac aag tgc aaa ctt ggt cta aat ggt gct ctg caa agc ggt cat    364
Tyr Tyr Lys Cys Lys Leu Gly Leu Asn Gly Ala Leu Gln Ser Gly His
        60                  65                  70 ttt tta tgc cca tgg aac ttg tat ata agt gag ttt tac caa aga tgt    412
Phe Leu Cys Pro Trp Asn Leu Tyr Ile Ser Glu Phe Tyr Gln Arg Cys
    75                  80                  85 gtg ggc cct aca tat tcg gaa tgt tta att aca cct ctg cct cct cca    460
Val Gly Pro Thr Tyr Ser Glu Cys Leu Ile Thr Pro Leu Pro Pro Pro
90                  95                  100                 105
```

-continued

| | | |
|---|---|---|
| att gtt ccg act act acg act acg aca act aca cca gca ccg cct<br>Ile Val Pro Thr Thr Thr Thr Thr Thr Thr Pro Ala Pro Pro Pro<br>                       110                     115                 120 | 508 |
| ctt ttt tca tgc gtg cag gaa ggg atg ttt ata gat ccc tat gac agc<br>Leu Phe Ser Cys Val Gln Glu Gly Met Phe Ile Asp Pro Tyr Asp Ser<br>             125                     130                     135 | 556 |
| act tgc aaa gga tac tac aaa tgt gct ttg aaa gca ggc gga gga ttc<br>Thr Cys Lys Gly Tyr Tyr Lys Cys Ala Leu Lys Ala Gly Gly Gly Phe<br>             140                     145                     150 | 604 |
| agt gta gcg cgt tac aat tgt cct ggt tct act tac ttc agc agc acg<br>Ser Val Ala Arg Tyr Asn Cys Pro Gly Ser Thr Tyr Phe Ser Ser Thr<br>       155                     160                     165 | 652 |
| tat cag caa tgt gtg gtc gct tcc ctt tcg gag tgc cta aga aat cct<br>Tyr Gln Gln Cys Val Val Ala Ser Leu Ser Glu Cys Leu Arg Asn Pro<br>170                     175                     180                 185 | 700 |
| cca gcg cct tgg caa cca cct acg ccg ccg ccc ata tac aac tgc gtg<br>Pro Ala Pro Trp Gln Pro Pro Thr Pro Pro Pro Ile Tyr Asn Cys Val<br>                     190                     195                 200 | 748 |
| cag agc ggc tca ttt gca gat cca gca gac aaa aca tgc aaa gta tat<br>Gln Ser Gly Ser Phe Ala Asp Pro Ala Asp Lys Thr Cys Lys Val Tyr<br>             205                     210                     215 | 796 |
| ttt gaa tgt gtg aga ctc tct gga gga aat ttc aac gtg ggt cgt ttt<br>Phe Glu Cys Val Arg Leu Ser Gly Gly Asn Phe Asn Val Gly Arg Phe<br>       220                     225                     230 | 844 |
| aca tgc gcc gga cag aca tac ttc agc gcg ctt tac caa caa tgc gtg<br>Thr Cys Ala Gly Gln Thr Tyr Phe Ser Ala Leu Tyr Gln Gln Cys Val<br>       235                     240                     245 | 892 |
| caa gcg cct tta tcc gag tgc ttg gcg aca gct gca cct cca cca ccg<br>Gln Ala Pro Leu Ser Glu Cys Leu Ala Thr Ala Ala Pro Pro Pro Pro<br>250                     255                     260                 265 | 940 |
| cca cca gga cca gga cca tcg caa ccc ttt gct tgc gtg cgg aca gga<br>Pro Pro Gly Pro Gly Pro Ser Gln Pro Phe Ala Cys Val Arg Thr Gly<br>             270                     275                     280 | 988 |
| ttg ttt ttg gat tac act gat aat tct tgc aaa tgg tac tac gag tgc<br>Leu Phe Leu Asp Tyr Thr Asp Asn Ser Cys Lys Trp Tyr Tyr Glu Cys<br>             285                     290                     295 | 1036 |
| aca tta aac gct caa ggt gta ttc gac gtg gcc cga tat gct tgt gca<br>Thr Leu Asn Ala Gln Gly Val Phe Asp Val Ala Arg Tyr Ala Cys Ala<br>             300                     305                     310 | 1084 |
| gct gag tta tat ttc aac agc gtt ctg cag cag tgc gta cct gca tac<br>Ala Glu Leu Tyr Phe Asn Ser Val Leu Gln Gln Cys Val Pro Ala Tyr<br>       315                     320                     325 | 1132 |
| cag tca gac tgt tta ggt gca agt gtc act tct tcc cca tcc ata cca<br>Gln Ser Asp Cys Leu Gly Ala Ser Val Thr Ser Ser Pro Ser Ile Pro<br>330                     335                     340                 345 | 1180 |
| tcc tta cca tcc tta cca tct ttc cca acc ttg cca aca tct tcc cca<br>Ser Leu Pro Ser Leu Pro Ser Phe Pro Thr Leu Pro Thr Ser Ser Pro<br>             350                     355                     360 | 1228 |
| aca gca gga ttt cct ttt ggc cga aaa tct ctt gat atg caa aca aaa<br>Thr Ala Gly Phe Pro Phe Gly Arg Lys Ser Leu Asp Met Gln Thr Lys<br>             365                     370                     375 | 1276 |
| act gga act aaa tgt aca aaa gga gaa gtt tct aaa gac gat tta aat<br>Thr Gly Thr Lys Cys Thr Lys Gly Glu Val Ser Lys Asp Asp Leu Asn<br>       380                     385                     390 | 1324 |
| tct aca tgt acc tagtgagtgt gttatatgaa attgctattg catattacat<br>Ser Thr Cys Thr<br>       395 | 1376 |
| acaagcttaa taaaggttat ggtgatttat ttcatttaaa ggcaatgtat cggtttaatg | 1436 |
| gttttaaatt tatttttat ttaatattaa atagattaat taaaaatcta taaagtgata | 1496 |

```
agaggcctga tatccataat attattgaat attaagaagt gacggataga tctgataatg   1556
tagtagttgg tatagacaat ttacttaata attatgagtg gcatcattat gcaatgattt   1616
atcactatta tttattcaac attttattta actgcttgca acttttaata aaacgcatnt   1676
tttattgttt taagtataaa tcttattagg gcacaatatg aaaataaaaa taagaacttt   1736
tatacaaaag ctnttttatc aatatgcttc ttgcgctatt aagttaagaa attttattta   1796
tgctgggaaa aaancaanaa atgctttatt tattct                              1832
```

<210> SEQ ID NO 43
<211> LENGTH: 397
<212> TYPE: PRT
<213> ORGANISM: Ctenocephalides felis

<400> SEQUENCE: 43

```
Met Lys Leu Leu Leu Val Leu Leu Ala Thr Phe Ser Cys Thr Leu Ser
1               5                   10                  15

Leu Glu Ser Gln Glu Leu Ile Pro Val Glu Thr Asn Ser Ser Ser Val
            20                  25                  30

Arg Ile Trp Gln Gln Pro Phe Ile Cys Pro Arg Val Gly Leu Phe Arg
        35                  40                  45

Asp Pro Leu Asp Pro Thr Cys Lys Arg Tyr Tyr Lys Cys Lys Leu Gly
    50                  55                  60

Leu Asn Gly Ala Leu Gln Ser Gly His Phe Leu Cys Pro Trp Asn Leu
65                  70                  75                  80

Tyr Ile Ser Glu Phe Tyr Gln Arg Cys Val Gly Pro Thr Tyr Ser Glu
                85                  90                  95

Cys Leu Ile Thr Pro Leu Pro Pro Ile Val Pro Thr Thr Thr Thr
            100                 105                 110

Thr Thr Thr Thr Pro Ala Pro Pro Leu Phe Ser Cys Val Gln Glu
        115                 120                 125

Gly Met Phe Ile Asp Pro Tyr Asp Ser Thr Cys Lys Gly Tyr Tyr Lys
    130                 135                 140

Cys Ala Leu Lys Ala Gly Gly Gly Phe Ser Val Ala Arg Tyr Asn Cys
145                 150                 155                 160

Pro Gly Ser Thr Tyr Phe Ser Ser Thr Tyr Gln Gln Cys Val Val Ala
                165                 170                 175

Ser Leu Ser Glu Cys Leu Arg Asn Pro Pro Ala Pro Trp Gln Pro Pro
            180                 185                 190

Thr Pro Pro Pro Ile Tyr Asn Cys Val Gln Ser Gly Ser Phe Ala Asp
        195                 200                 205

Pro Ala Asp Lys Thr Cys Lys Val Tyr Phe Glu Cys Val Arg Leu Ser
    210                 215                 220

Gly Gly Asn Phe Asn Val Gly Arg Phe Thr Cys Ala Gly Gln Thr Tyr
225                 230                 235                 240

Phe Ser Ala Leu Tyr Gln Gln Cys Val Gln Ala Pro Leu Ser Glu Cys
                245                 250                 255

Leu Ala Thr Ala Ala Pro Pro Pro Pro Gly Pro Gly Pro Ser
            260                 265                 270

Gln Pro Phe Ala Cys Val Arg Thr Gly Leu Phe Leu Asp Tyr Thr Asp
        275                 280                 285

Asn Ser Cys Lys Trp Tyr Tyr Glu Cys Thr Leu Asn Ala Gln Gly Val
    290                 295                 300

Phe Asp Val Ala Arg Tyr Ala Cys Ala Ala Glu Leu Tyr Phe Asn Ser
305                 310                 315                 320
```

```
Val Leu Gln Gln Cys Val Pro Ala Tyr Gln Ser Asp Cys Leu Gly Ala
            325                 330                 335

Ser Val Thr Ser Ser Pro Ser Ile Pro Ser Leu Pro Ser Leu Pro Ser
            340                 345                 350

Phe Pro Thr Leu Pro Thr Ser Ser Pro Thr Ala Gly Phe Pro Phe Gly
            355                 360                 365

Arg Lys Ser Leu Asp Met Gln Thr Lys Thr Gly Thr Lys Cys Thr Lys
            370                 375                 380

Gly Glu Val Ser Lys Asp Asp Leu Asn Ser Thr Cys Thr
385                 390                 395

<210> SEQ ID NO 44
<211> LENGTH: 1832
<212> TYPE: DNA
<213> ORGANISM: Ctenocephalides felis
<220> FEATURE:
<221> NAME/KEY: misc_feature
<222> LOCATION: (19)..(19)
<223> OTHER INFORMATION: n = unknown
<220> FEATURE:
<221> NAME/KEY: misc_feature
<222> LOCATION: (23)..(23)
<223> OTHER INFORMATION: n = unknown
<220> FEATURE:
<221> NAME/KEY: misc_feature
<222> LOCATION: (84)..(84)
<223> OTHER INFORMATION: n = unknown
<220> FEATURE:
<221> NAME/KEY: misc_feature
<222> LOCATION: (158)..(158)
<223> OTHER INFORMATION: n = unknown
<220> FEATURE:
<221> NAME/KEY: misc_feature
<222> LOCATION: (1830)..(1830)
<223> OTHER INFORMATION: n = unknown

<400> SEQUENCE: 44
agaataaata aagcatttnt tgnttttttc ccagcataaa taaaatttct taacttaata      60
gcgcaagaag catattgata aaanagcttt tgtataaagt tctttatttt tattttcata     120
ttgtgcccta ataagattta tacttaaaac aataaaanat gcgttttatt aaaagttgca     180
agcagttaaa taaatgttg aataaataat agtgataaat cattgcataa tgatgccact      240
cataattatt aagtaaattg tctataccaa ctactacatt atcagatcta tccgtcactt     300
cttaatattc aataatatta tggatatcag gcctcttatc actttataga tttttaatta     360
atctatttaa tattaaataa aaaataaatt taaaaccatt aaaccgatac attgccttta     420
aatgaaataa atcaccataa cctttattaa gcttgtatgt aatatgcaat agcaatttca     480
tataacacac tcactaggta catgtagaat ttaaatcgtc tttagaaact tctccttttg     540
tacatttagt tccagttttt gtttgcatat caagagattt tcggccaaaa ggaaatcctg     600
ctgttgggga agatgttggc aaggttggga aagatggtaa ggatggtaag gatggtatgg     660
atggggaaga agtgacactt gcacctaaac agtctgactg gtatgcaggt acgcactgct     720
gcagaacgct gttgaaatat aactcagctg cacaagcata tcgggccacg tcgaatacac     780
cttgagcgtt taatgtgcac tcgtagtacc atttgcaaga attatcagtg taatccaaaa     840
acaatcctgt ccgcacgcaa gcaaagggtt gcgatggtcc tggtcctggt ggcggtggtg     900
gaggtgcagc tgtcgccaag cactcggata aggcgcttg cacgcattgt tggtaaagcg      960
cgctgaagta tgtctgtccg gcgcatgtaa acgacccac gttgaaattt cctccagaga     1020
gtctcacaca ttcaaaatat actttgcatg ttttgtctgc tggatctgca aatgagccgc    1080
```

-continued

| | |
|---|---|
| tctgcacgca gttgtatatg ggcggcggcg taggtggttg ccaaggcgct ggaggatttc | 1140 |
| ttaggcactc cgaaagggaa gcgaccacac attgctgata cgtgctgctg aagtaagtag | 1200 |
| aaccaggaca attgtaacgc gctacactga atcctccgcc tgctttcaaa gcacatttgt | 1260 |
| agtatccttt gcaagtgctg tcatagggat ctataaacat ccctcctgc acgcatgaaa | 1320 |
| aaagaggcgg cggtgctggt gtagttgtcg tagtcgtagt agtcggaaca attggaggag | 1380 |
| gcagaggtgt aattaaacat tccgaatatg tagggcccac acatctttgg taaaactcac | 1440 |
| ttatatacaa gttccatggg cataaaaaat gaccgctttg cagagcacca tttagaccaa | 1500 |
| gtttgcactt gtagtacctt tgcatgtag gatccaatgg atcgcgaaat agtccaactc | 1560 |
| ttggacaaat gaatggttgc tgccaaatac gaacgctgct ggaatttgtt tcaactggaa | 1620 |
| ttagttcttg agactccaaa gacaatgtac acgagaaggt agccaagagc actaaaagca | 1680 |
| gtttcatcgt aatgaaacgc gatttaacag attccacttt aaaataaaca attttttga | 1740 |
| taatgatatt gtaccaaaaa tttgaagtta ctaaatcccc cgcgtactct gcgttgttac | 1800 |
| ccactgcttg ccctatagtg agtcgtattn ga | 1832 |

<210> SEQ ID NO 45
<211> LENGTH: 1191
<212> TYPE: DNA
<213> ORGANISM: Ctenocephalides felis

<400> SEQUENCE: 45

| | |
|---|---|
| atgaaactgc ttttagtgct cttggctacc ttctcgtgta cattgtcttt ggagtctcaa | 60 |
| gaactaattc cagttgaaac aaattccagc agcgttcgta tttggcagca accattcatt | 120 |
| tgtccaagag ttggactatt tcgcgatcca ttggatccta catgcaaaag gtactacaag | 180 |
| tgcaaacttg gtctaaatgg tgctctgcaa agcggtcatt ttttatgccc atggaacttg | 240 |
| tatataagtg agttttacca aagatgtgtg ggccctacat attcggaatg tttaattaca | 300 |
| cctctgcctc ctccaattgt tccgactact acgactacga caactacacc agcaccgccg | 360 |
| cctcttttt catgcgtgca ggaagggatg tttatagatc cctatgacag cacttgcaaa | 420 |
| ggatactaca aatgtgcttt gaaagcaggc ggaggattca gtgtagcgcg ttacaattgt | 480 |
| cctggttcta cttacttcag cagcacgtat cagcaatgtg tggtcgcttc cctttcggag | 540 |
| tgcctaagaa atcctccagc gccttggcaa ccacctacgc cgccgcccat atacaactgc | 600 |
| gtgcagagcg gctcatttgc agatccagca gacaaaacat gcaaagtata ttttgaatgt | 660 |
| gtgagactct ctggaggaaa tttcaacgtg ggtcgtttta catgcgccgg acagacatac | 720 |
| ttcagcgcgc tttaccaaca atgcgtgcaa gcgcctttat ccgagtgctt ggcgacagct | 780 |
| gcacctccac caccgccacc aggaccagga ccatcgcaac cctttgcttg cgtgcggaca | 840 |
| ggattgtttt tggattacac tgataattct tgcaaatggt actacgagtg cacattaaac | 900 |
| gctcaaggtg tattcgacgt ggcccgatat gcttgtgcag ctgagttata tttcaacagc | 960 |
| gttctgcagc agtgcgtacc tgcataccag tcagactgtt taggtgcaag tgtcacttct | 1020 |
| tccccatcca taccatcctt accatcctta ccatcttcc caaccttgcc aacatcttcc | 1080 |
| ccaacagcag gatttccttt tggccgaaaa tctcttgata tgcaaacaaa aactggaact | 1140 |
| aaatgtacaa aaggagaagt ttctaaagac gatttaaatt ctacatgtac c | 1191 |

<210> SEQ ID NO 46
<211> LENGTH: 1191
<212> TYPE: DNA
<213> ORGANISM: Ctenocephalides felis

<400> SEQUENCE: 46

| | | | | | |
|---|---|---|---|---|---|
| ggtacatgta | gaatttaaat | cgtctttaga | aacttctcct | tttgtacatt | tagttccagt | 60 |
| ttttgtttgc | atatcaagag | attttcggcc | aaaaggaaat | cctgctgttg | gggaagatgt | 120 |
| tggcaaggtt | gggaaagatg | gtaaggatgg | taaggatggt | atggatgggg | aagaagtgac | 180 |
| acttgcacct | aaacagtctg | actggtatgc | aggtacgcac | tgctgcagaa | cgctgttgaa | 240 |
| atataactca | gctgcacaag | catatcgggc | cacgtcgaat | acaccttgag | cgtttaatgt | 300 |
| gcactcgtag | taccatttgc | aagaattatc | agtgtaatcc | aaaaacaatc | ctgtccgcac | 360 |
| gcaagcaaag | ggttgcgatg | gtcctggtcc | tggtggcggt | ggtggaggtg | cagctgtcgc | 420 |
| caagcactcg | gataaaggcg | cttgcacgca | ttgttggtaa | agcgcgctga | agtatgtctg | 480 |
| tccggcgcat | gtaaaacgac | ccacgttgaa | atttcctcca | gagagtctca | cacattcaaa | 540 |
| atatactttg | catgttttgt | ctgctggatc | tgcaaatgag | ccgctctgca | cgcagttgta | 600 |
| tatgggcggc | ggcgtaggtg | gttgccaagg | cgctggagga | tttcttaggc | actccgaaag | 660 |
| ggaagcgacc | acacattgct | gatacgtgct | gctgaagtaa | gtagaaccag | gacaattgta | 720 |
| acgcgctaca | ctgaatcctc | cgcctgcttt | caaagcacat | ttgtagtatc | ctttgcaagt | 780 |
| gctgtcatag | ggatctataa | acatcccttc | ctgcacgcat | gaaaaaagag | gcggcggtgc | 840 |
| tggtgtagtt | gtcgtagtcg | tagtagtcgg | aacaattgga | ggaggcagag | gtgtaattaa | 900 |
| acattccgaa | tatgtagggc | ccacacatct | ttggtaaaac | tcacttatat | acaagttcca | 960 |
| tgggcataaa | aaatgaccgc | tttgcagagc | accatttaga | ccaagtttgc | acttgtagta | 1020 |
| ccttttgcat | gtaggatcca | atggatcgcg | aaatagtcca | actcttggac | aaatgaatgg | 1080 |
| ttgctgccaa | atacgaacgc | tgctggaatt | tgtttcaact | ggaattagtt | cttgagactc | 1140 |
| caaagacaat | gtacacgaga | aggtagccaa | gagcactaaa | agcagtttca | t | 1191 |

<210> SEQ ID NO 47
<211> LENGTH: 1161
<212> TYPE: DNA
<213> ORGANISM: Ctenocephalides felis
<220> FEATURE:
<221> NAME/KEY: CDS
<222> LOCATION: (1)..(1143)
<223> OTHER INFORMATION:

<400> SEQUENCE: 47

| | | | | | | | | | | | | | | | | |
|---|---|---|---|---|---|---|---|---|---|---|---|---|---|---|---|---|
| ttg | gag | tct | caa | gaa | cta | att | cca | gtt | gaa | aca | aat | tcc | agc | agc | gtt | 48 |
| Leu | Glu | Ser | Gln | Glu | Leu | Ile | Pro | Val | Glu | Thr | Asn | Ser | Ser | Ser | Val | |
| 1 | | | | 5 | | | | | 10 | | | | | 15 | | |

| cgt | att | tgg | cag | caa | cca | ttc | att | tgt | cca | aga | gtt | gga | cta | ttt | cgc | 96 |
|---|---|---|---|---|---|---|---|---|---|---|---|---|---|---|---|---|
| Arg | Ile | Trp | Gln | Gln | Pro | Phe | Ile | Cys | Pro | Arg | Val | Gly | Leu | Phe | Arg | |
| | | | 20 | | | | | 25 | | | | | 30 | | | |

| gat | cca | ttg | gat | cct | aca | tgc | aaa | agg | tac | tac | aag | tgc | aaa | ctt | ggt | 144 |
|---|---|---|---|---|---|---|---|---|---|---|---|---|---|---|---|---|
| Asp | Pro | Leu | Asp | Pro | Thr | Cys | Lys | Arg | Tyr | Tyr | Lys | Cys | Lys | Leu | Gly | |
| | | 35 | | | | | 40 | | | | | 45 | | | | |

| cta | aat | ggt | gct | ctg | caa | agc | ggt | cat | ttt | tta | tgc | cca | tgg | aac | ttg | 192 |
|---|---|---|---|---|---|---|---|---|---|---|---|---|---|---|---|---|
| Leu | Asn | Gly | Ala | Leu | Gln | Ser | Gly | His | Phe | Leu | Cys | Pro | Trp | Asn | Leu | |
| | 50 | | | | | 55 | | | | | 60 | | | | | |

| tat | ata | agt | gag | ttt | tac | caa | aga | tgt | gtg | ggc | cct | aca | tat | tcg | gaa | 240 |
|---|---|---|---|---|---|---|---|---|---|---|---|---|---|---|---|---|
| Tyr | Ile | Ser | Glu | Phe | Tyr | Gln | Arg | Cys | Val | Gly | Pro | Thr | Tyr | Ser | Glu | |
| 65 | | | | 70 | | | | | 75 | | | | | 80 | | |

-continued

| | | |
|---|---|---|
| tgt tta att aca cct ctg cct cct cca att gtt ccg act act acg act<br>Cys Leu Ile Thr Pro Leu Pro Pro Pro Ile Val Pro Thr Thr Thr Thr<br>                          85                              90                       95 | 288 |
| acg aca act aca cca gca ccg ccg cct ctt ttt tca tgc gtg cag gaa<br>Thr Thr Thr Thr Pro Ala Pro Pro Pro Leu Phe Ser Cys Val Gln Glu<br>            100                              105                      110 | 336 |
| ggg atg ttt ata gat ccc tat gac agc act tgc aaa gga tac tac aaa<br>Gly Met Phe Ile Asp Pro Tyr Asp Ser Thr Cys Lys Gly Tyr Tyr Lys<br>              115                          120                      125 | 384 |
| tgt gct ttg aaa gca ggc gga gga ttc agt gta gcg cgt tac aat tgt<br>Cys Ala Leu Lys Ala Gly Gly Gly Phe Ser Val Ala Arg Tyr Asn Cys<br>130                            135                          140 | 432 |
| cct ggt tct act tac ttc agc agc acg tat cag caa tgt gtg gtc gct<br>Pro Gly Ser Thr Tyr Phe Ser Ser Thr Tyr Gln Gln Cys Val Val Ala<br>145                            150                          155                      160 | 480 |
| tcc ctt tcg gag tgc cta aga aat cct cca gcg cct tgg caa cca cct<br>Ser Leu Ser Glu Cys Leu Arg Asn Pro Pro Ala Pro Trp Gln Pro Pro<br>                          165                              170                      175 | 528 |
| acg ccg ccg ccc ata tac aac tgc gtg cag agc ggc tca ttt gca gat<br>Thr Pro Pro Pro Ile Tyr Asn Cys Val Gln Ser Gly Ser Phe Ala Asp<br>            180                              185                      190 | 576 |
| cca gca gac aaa aca tgc aaa gta tat ttt gaa tgt gtg aga ctc tct<br>Pro Ala Asp Lys Thr Cys Lys Val Tyr Phe Glu Cys Val Arg Leu Ser<br>              195                          200                      205 | 624 |
| gga gga aat ttc aac gtg ggt cgt ttt aca tgc gcc gga cag aca tac<br>Gly Gly Asn Phe Asn Val Gly Arg Phe Thr Cys Ala Gly Gln Thr Tyr<br>            210                              215                      220 | 672 |
| ttc agc gcg ctt tac caa caa tgc gtg caa gcg cct tta tcc gag tgc<br>Phe Ser Ala Leu Tyr Gln Gln Cys Val Gln Ala Pro Leu Ser Glu Cys<br>225                            230                          235                      240 | 720 |
| ttg gcg aca gct gca cct cca cca ccg cca cca gga cca gga cca tcg<br>Leu Ala Thr Ala Ala Pro Pro Pro Pro Pro Pro Gly Pro Gly Pro Ser<br>                          245                              250                      255 | 768 |
| caa ccc ttt gct tgc gtg cgg aca gga ttg ttt ttg gat tac act gat<br>Gln Pro Phe Ala Cys Val Arg Thr Gly Leu Phe Leu Asp Tyr Thr Asp<br>            260                              265                      270 | 816 |
| aat tct tgc aaa tgg tac tac gag tgc aca tta aac gct caa ggt gta<br>Asn Ser Cys Lys Trp Tyr Tyr Glu Cys Thr Leu Asn Ala Gln Gly Val<br>              275                          280                      285 | 864 |
| ttc gac gtg gcc cga tat gct tgt gca gct gag tta tat ttc aac agc<br>Phe Asp Val Ala Arg Tyr Ala Cys Ala Ala Glu Leu Tyr Phe Asn Ser<br>290                            295                          300 | 912 |
| gtt ctg cag cag tgc gta cct gca tac cag tca gac tgt tta ggt gca<br>Val Leu Gln Gln Cys Val Pro Ala Tyr Gln Ser Asp Cys Leu Gly Ala<br>305                            310                          315                      320 | 960 |
| agt gtc act tct tcc cca tcc ata cca tcc tta cca tcc tta cca tct<br>Ser Val Thr Ser Ser Pro Ser Ile Pro Ser Leu Pro Ser Leu Pro Ser<br>              325                          330                      335 | 1008 |
| ttc cca acc ttg cca aca tct tcc cca aca gca gga ttt cct ttt ggc<br>Phe Pro Thr Leu Pro Thr Ser Ser Pro Thr Ala Gly Phe Pro Phe Gly<br>            340                              345                      350 | 1056 |
| cga aaa tct ctt gat atg caa aca aaa act gga act aaa tgt aca aaa<br>Arg Lys Ser Leu Asp Met Gln Thr Lys Thr Gly Thr Lys Cys Thr Lys<br>              355                          360                      365 | 1104 |
| gga gaa gtt tct aaa gac gat tta aat tct aca tgt acc tagtgagtgt<br>Gly Glu Val Ser Lys Asp Asp Leu Asn Ser Thr Cys Thr<br>370                          375                          380 | 1153 |
| gttatatg | 1161 |

```
<210> SEQ ID NO 48
<211> LENGTH: 381
<212> TYPE: PRT
<213> ORGANISM: Ctenocephalides felis

<400> SEQUENCE: 48

Leu Glu Ser Gln Glu Leu Ile Pro Val Glu Thr Asn Ser Ser Ser Val
1               5                   10                  15

Arg Ile Trp Gln Gln Pro Phe Ile Cys Pro Arg Val Gly Leu Phe Arg
            20                  25                  30

Asp Pro Leu Asp Pro Thr Cys Lys Arg Tyr Tyr Lys Cys Lys Leu Gly
        35                  40                  45

Leu Asn Gly Ala Leu Gln Ser Gly His Phe Leu Cys Pro Trp Asn Leu
    50                  55                  60

Tyr Ile Ser Glu Phe Tyr Gln Arg Cys Val Gly Pro Thr Tyr Ser Glu
65                  70                  75                  80

Cys Leu Ile Thr Pro Leu Pro Pro Ile Val Pro Thr Thr Thr
                85                  90                  95

Thr Thr Thr Thr Pro Ala Pro Pro Leu Phe Ser Cys Val Gln Glu
            100                 105                 110

Gly Met Phe Ile Asp Pro Tyr Asp Ser Thr Cys Lys Gly Tyr Tyr Lys
        115                 120                 125

Cys Ala Leu Lys Ala Gly Gly Phe Ser Val Ala Arg Tyr Asn Cys
    130                 135                 140

Pro Gly Ser Thr Tyr Phe Ser Ser Thr Tyr Gln Gln Cys Val Val Ala
145                 150                 155                 160

Ser Leu Ser Glu Cys Leu Arg Asn Pro Ala Pro Trp Gln Pro Pro
                165                 170                 175

Thr Pro Pro Pro Ile Tyr Asn Cys Val Gln Ser Gly Ser Phe Ala Asp
            180                 185                 190

Pro Ala Asp Lys Thr Cys Lys Val Tyr Phe Glu Cys Val Arg Leu Ser
        195                 200                 205

Gly Gly Asn Phe Asn Val Gly Arg Phe Thr Cys Ala Gly Gln Thr Tyr
    210                 215                 220

Phe Ser Ala Leu Tyr Gln Gln Cys Val Gln Ala Pro Leu Ser Glu Cys
225                 230                 235                 240

Leu Ala Thr Ala Ala Pro Pro Pro Pro Gly Pro Gly Pro Ser
                245                 250                 255

Gln Pro Phe Ala Cys Val Arg Thr Gly Leu Phe Leu Asp Tyr Thr Asp
            260                 265                 270

Asn Ser Cys Lys Trp Tyr Tyr Glu Cys Thr Leu Asn Ala Gln Gly Val
        275                 280                 285

Phe Asp Val Ala Arg Tyr Ala Cys Ala Ala Glu Leu Tyr Phe Asn Ser
    290                 295                 300

Val Leu Gln Gln Cys Val Pro Ala Tyr Gln Ser Asp Cys Leu Gly Ala
305                 310                 315                 320

Ser Val Thr Ser Ser Pro Ser Ile Pro Ser Leu Pro Ser Leu Pro Ser
                325                 330                 335

Phe Pro Thr Leu Pro Thr Ser Ser Pro Thr Ala Gly Phe Pro Phe Gly
            340                 345                 350

Arg Lys Ser Leu Asp Met Gln Thr Lys Thr Gly Thr Lys Cys Thr Lys
        355                 360                 365

Gly Glu Val Ser Lys Asp Asp Leu Asn Ser Thr Cys Thr
    370                 375                 380
```

<210> SEQ ID NO 49
<211> LENGTH: 1161
<212> TYPE: DNA
<213> ORGANISM: Ctenocephalides felis

<400> SEQUENCE: 49

```
catataacac actcactagg tacatgtaga atttaaatcg tctttagaaa cttctccttt      60
tgtacattta gttccagttt ttgtttgcat atcaagagat tttcggccaa aaggaaatcc     120
tgctgttggg gaagatgttg gcaaggttgg gaaagatggt aaggatggta aggatggtat     180
ggatggggaa gaagtgacac ttgcacctaa acagtctgac tggtatgcag gtacgcactg     240
ctgcagaacg ctgttgaaat ataactcagc tgcacaagca tatcgggcca cgtcgaatac     300
accttgagcg tttaatgtgc actcgtagta ccatttgcaa gaattatcag tgtaatccaa     360
aaacaatcct gtccgcacgc aagcaaaggg ttgcgatggt cctggtcctg gtggcggtgg     420
tggaggtgca gctgtcgcca agcactcgga taaaggcgct tgcacgcatt gttggtaaag     480
cgcgctgaag tatgtctgtc cggcgcatgt aaaacgaccc acgttgaaat ttcctccaga     540
gagtctcaca cattcaaaat atactttgca tgttttgtct gctggatctg caaatgagcc     600
gctctgcacg cagttgtata tgggcggcgg cgtaggtggt tgccaaggcg ctggaggatt     660
tcttaggcac tccgaaaggg aagcgaccac acattgctga tacgtgctgc tgaagtaagt     720
agaaccagga caattgtaac gcgctacact gaatcctccg cctgctttca aagcacattt     780
gtagtatcct ttgcaagtgc tgtcataggg atctataaac atcccttcct gcacgcatga     840
aaaagaggc ggcggtgctg gtgtagttgt cgtagtcgta gtagtcggaa caattggagg     900
aggcagaggt gtaattaaac attccgaata tgtagggccc acacatcttt ggtaaaactc     960
acttatatac aagttccatg ggcataaaaa atgaccgctt tgcagagcac catttagacc    1020
aagtttgcac ttgtagtacc ttttgcatgt aggatccaat ggatcgcgaa atagtccaac    1080
tcttggacaa atgaatggtt gctgccaaat acgaacgctg ctggaatttg tttcaactgg    1140
aattagttct tgagactcca a                                               1161
```

<210> SEQ ID NO 50
<211> LENGTH: 29
<212> TYPE: DNA
<213> ORGANISM: Artificial sequence
<220> FEATURE:
<223> OTHER INFORMATION: Synthetic Primer

<400> SEQUENCE: 50
cgggatcctg ctgacaggaa ttcgcccac       29

<210> SEQ ID NO 51
<211> LENGTH: 31
<212> TYPE: DNA
<213> ORGANISM: Artificial sequence
<220> FEATURE:
<223> OTHER INFORMATION: Synthetic Primer

<400> SEQUENCE: 51
catggtaccc ctggtttaag ccttacttag c       31

<210> SEQ ID NO 52
<211> LENGTH: 21
<212> TYPE: DNA
<213> ORGANISM: Artificial sequence
<220> FEATURE:
<223> OTHER INFORMATION: Synthetic Primer

```
<400> SEQUENCE: 52
gtctggaagc tcaggaagag g                                              21

<210> SEQ ID NO 53
<211> LENGTH: 27
<212> TYPE: DNA
<213> ORGANISM: Artificial sequence
<220> FEATURE:
<223> OTHER INFORMATION: Synthetic Primer

<400> SEQUENCE: 53
ccatcctaat acgactcact atagggc                                        27

<210> SEQ ID NO 54
<211> LENGTH: 23
<212> TYPE: DNA
<213> ORGANISM: Artificial sequence
<220> FEATURE:
<223> OTHER INFORMATION: Synthetic Primer

<400> SEQUENCE: 54
actcactata gggctcgagc ggc                                            23

<210> SEQ ID NO 55
<211> LENGTH: 24
<212> TYPE: DNA
<213> ORGANISM: Artificial sequence
<220> FEATURE:
<223> OTHER INFORMATION: Synthetic Primer

<400> SEQUENCE: 55
gtaatatgcg tgacaatcgt gtgg                                           24

<210> SEQ ID NO 56
<211> LENGTH: 24
<212> TYPE: DNA
<213> ORGANISM: Artificial sequence
<220> FEATURE:
<223> OTHER INFORMATION: Synthetic Primer

<400> SEQUENCE: 56
cggtgcaagt tatagaacct tccg                                           24

<210> SEQ ID NO 57
<211> LENGTH: 32
<212> TYPE: DNA
<213> ORGANISM: Artificial sequence
<220> FEATURE:
<223> OTHER INFORMATION: Synthetic Primer

<400> SEQUENCE: 57
cgggatcccg aatatgctga cgtagatgtg tg                                  32

<210> SEQ ID NO 58
<211> LENGTH: 32
<212> TYPE: DNA
<213> ORGANISM: Artificial sequence
<220> FEATURE:
<223> OTHER INFORMATION: Synthetic Primer

<400> SEQUENCE: 58
ggaattctgt tttattctgg ttggtaacat tc                                  32

<210> SEQ ID NO 59
<211> LENGTH: 23
```

```
<212> TYPE: DNA
<213> ORGANISM: Artificial sequence
<220> FEATURE:
<223> OTHER INFORMATION: Synthetic Primer

<400> SEQUENCE: 59
gatatccact ttgatcagcg cac                                          23

<210> SEQ ID NO 60
<211> LENGTH: 21
<212> TYPE: DNA
<213> ORGANISM: Artificial sequence
<220> FEATURE:
<223> OTHER INFORMATION: Synthetic Primer

<400> SEQUENCE: 60
ggtactactc ctggtgcggg c                                            21

<210> SEQ ID NO 61
<211> LENGTH: 23
<212> TYPE: DNA
<213> ORGANISM: Artificial sequence
<220> FEATURE:
<223> OTHER INFORMATION: Synthetic Primer

<400> SEQUENCE: 61
ccgtcgacat taaactcacc atc                                          23

<210> SEQ ID NO 62
<211> LENGTH: 31
<212> TYPE: DNA
<213> ORGANISM: Artificial sequence
<220> FEATURE:
<223> OTHER INFORMATION: Synthetic Primer

<400> SEQUENCE: 62
cgggatcctt atgatggtga gtttaatgtc g                                 31

<210> SEQ ID NO 63
<211> LENGTH: 34
<212> TYPE: DNA
<213> ORGANISM: Artificial sequence
<220> FEATURE:
<223> OTHER INFORMATION: Synthetic Primer

<400> SEQUENCE: 63
ggggtacctt aatataattt aggtttcctc tcgc                              34

<210> SEQ ID NO 64
<211> LENGTH: 21
<212> TYPE: DNA
<213> ORGANISM: Artificial sequence
<220> FEATURE:
<223> OTHER INFORMATION: Synthetic Primer

<400> SEQUENCE: 64
gcgcatgtaa aacgacccac g                                            21

<210> SEQ ID NO 65
<211> LENGTH: 45
<212> TYPE: DNA
<213> ORGANISM: Artificial sequence
<220> FEATURE:
<223> OTHER INFORMATION: Synthetic Primer
```

-continued

```
<400> SEQUENCE: 65
ctaatacgac tcactatagg gcaagcagtg gtaacaacgc agagt                          45

<210> SEQ ID NO 66
<211> LENGTH: 22
<212> TYPE: DNA
<213> ORGANISM: Artificial sequence
<220> FEATURE:
<223> OTHER INFORMATION: Synthetic Primer

<400> SEQUENCE: 66
ctaatacgac tcactatagg gc                                                   22

<210> SEQ ID NO 67
<211> LENGTH: 30
<212> TYPE: DNA
<213> ORGANISM: Artificial sequence
<220> FEATURE:
<223> OTHER INFORMATION: Synthetic Primer

<400> SEQUENCE: 67
cgggtacctt ggagtctcaa gaactaattc                                           30

<210> SEQ ID NO 68
<211> LENGTH: 37
<212> TYPE: DNA
<213> ORGANISM: Artificial sequence
<220> FEATURE:
<223> OTHER INFORMATION: Synthetic Primer

<400> SEQUENCE: 68
aggaattcca tataacacac tcactaggta catgtag                                   37
```

FLEA PERITROPHIN NUCLEIC ACID MOLECULES, PROTEINS AND USES THEREOF

CROSS REFERENCE TO RELATED APPLICATIONS

This application is a Continuation-in-Part of U.S. patent application Ser. No. 09/543,668, filed Apr. 7, 2000, which claims priority to U.S. Provisional Patent Application Serial No. 60/128,704, filed Apr. 9, 1999, each entitled "NOVEL FLEA HEAD, NERVE CORD, HINDGUT AND MALPIGHIAN TUBULE NUCLEIC ACID MOLECULES, PROTEINS AND USES THEREOF".

FIELD OF THE INVENTION

The present invention relates to flea peritrophin nucleic acid molecules, proteins encoded by such nucleic acid molecules, antibodies raised against such proteins, and inhibitors of such proteins. The present invention also includes methods to obtain such proteins, nucleic acid molecules, antibodies, and inhibitory compounds. The present invention also includes therapeutic compositions comprising such inhibitors, as well as uses thereof.

BACKGROUND OF THE INVENTION

Flea infestation of animals is a health and economic concern for pet owners. In particular, the bites of fleas are a problem for animals maintained as pets because the infestation becomes a source of annoyance not only for the pet but also for the pet owner who may find his or her home generally contaminated with insects. Fleas also directly cause a variety of diseases, including allergy, and also carry a variety of infectious agents including, but not limited to, endoparasites (e.g., nematodes, cestodes, trematodes and protozoa), bacteria and viruses. As such, fleas are a problem not only when they are on an animal but also when they are in the general environment of the animal.

The medical importance of flea infestation has prompted the development of reagents capable of controlling flea infestation. Commonly encountered methods to control flea infestation are generally focused on use of insecticides, which are often unsuccessful for one or more of the following reasons: (1) failure of owner compliance (frequent administration is required); (2) behavioral or physiological intolerance of the pet to the pesticide product or means of administration; and (3) the emergence of flea populations resistant to the prescribed dose of pesticide.

Peritrophins, including flea PL1, PL2, PL3, PL4 and PL5 proteins of the present invention, are a family of putative chitin-binding proteins that comprise a structural component of the peritrophic matrix, an acellular membrane composed of proteins and sugars, most commonly chitin which forms a barrier between the contents of an ingested meal and the gut epithelia. Peritrophin-like proteins have also been shown to be present in the trachea of Drosophila embryos, indicating that such proteins may have additional roles outside the midgut. The function of the peritrophin-like proteins in adult fleas is not clear, since adult fleas do not produce a peritrophic matrix in the gut. Peritrophins have been investigated as targets for immunological control of hematophagous insects including the sheep blowfly, *Lucilia cuprina*. It has been shown in this insect that ingestion of antibodies against peritrophins inhibits the growth of larvae and can result in increased larval mortality. It has also been shown that the ingestion of antibodies against peritrophins reduces the permeability of the peritrophic matrix in *L. cuprina* larvae. This in turn may inhibit the movement of digested food across the peritrophic matrix to the gut epithelium, resulting in starvation. As such, a flea peritrophin of the present invention represents a novel target for anti-flea vaccines and chemotherapeutic drugs.

Therefore, isolation and sequencing of flea peritrophin genes may be critical for use in identifying specific agents for treating animals for flea infestation.

SUMMARY OF THE INVENTION

The present invention provides flea peritrophin nucleic acid molecules, proteins encoded by such nucleic acid molecules; antibodies raised against such proteins (i.e., anti-flea peritrophin antibodies); mimetopes of such proteins or antibodies; compositions comprising such nucleic acid molecules, proteins, antibodies, and mimetopes; and compounds that inhibit flea peritrophin activity (i.e. inhibitory compounds or inhibitors).

The present invention also includes methods to obtain such proteins, mimetopes, nucleic acid molecules, antibodies and inhibitory compounds. The present invention also includes the use of proteins and antibodies to identify such inhibitory compounds as well as assay kits to identify such inhibitory compounds. Also included in the present invention are therapeutic compositions comprising proteins, mimetopes, nucleic acid molecules, antibodies and inhibitory compounds of the present invention including therapeutic compounds derived from a protein of the present invention that inhibit the activity of flea peritrophin proteins; also included are uses of such therapeutic compounds.

One embodiment of the present invention is an isolated flea peritrophin nucleic acid molecule that hybridizes with a nucleic acid sequence having SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, and/or SEQ ID NO:49, under conditions that allow less than or equal to 30% base pair mismatch. Another embodiment of the present invention is an isolated flea peritrophin nucleic acid molecule having a nucleic acid sequence that is at least 70% identical to SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, and/or SEQ ID NO:49 and fragments of any of such nucleic acid sequences of at least 35 nucleotides in length.

The present invention also relates to recombinant molecules, recombinant viruses and recombinant cells that include a nucleic acid molecule of the present invention.

Also included are methods to produce such nucleic acid molecules, recombinant molecules, recombinant viruses and recombinant cells.

Another embodiment of the present invention includes an isolated flea peritrophin protein that is at least 70% identical to an amino acid sequence selected from the group consisting of SEQ ID NO:2, SEQ ID NO:12, SEQ ID NO:17, SEQ ID NO:26, SEQ ID NO:31, SEQ ID NO:40, SEQ ID NO:43, and/or SEQ ID NO:48 and fragments thereof having at least 10 amino acid residues, wherein such fragments can elicit an immune response against respective flea peritrophin proteins or selectively binds to an antibody that binds any of such amino acid sequences.

Another embodiment of the present invention includes an isolated flea peritrophin protein encoded by a nucleic acid molecule at least 35 nucleotides in length that hybridizes with a nucleic acid sequence having SEQ ID NO:3, SEQ ID NO:5, SEQ ID NO:8, SEQ ID NO:10, SEQ ID NO:13, SEQ ID NO:15, SEQ ID NO:18, SEQ ID NO:20, SEQ ID NO:22, SEQ ID NO:24, SEQ ID NO:27, SEQ ID NO:29, SEQ ID NO:32, SEQ ID NO:41, SEQ ID NO:44, SEQ ID NO:46, and/or SEQ ID NO:49, under conditions that allow less than or equal to 30% base pair mismatch.

Another embodiment of the present invention includes a composition comprising an excipient and a compound selected from the group consisting of nucleic acid molecules, proteins, and antibodies of the present invention and a method to treat an animal for flea infestation comprising administering such a composition to such an animal.

Another embodiment of the present invention includes a method to detect an inhibitor of flea peritrophin activity, said method comprising (a) contacting an isolated flea peritrophin protein of the present invention, with a putative inhibitory compound under conditions in which, in the absence of said compound, said protein has flea peritrophin protein activity, and (b) determining if said putative inhibitory compound inhibits flea peritrophin protein activity.

DETAILED DESCRIPTION OF THE INVENTION

The present invention provides for flea peritrophin nucleic acid molecules, proteins encoded by such nucleic acid molecules, antibodies raised against such proteins, and inhibitors of such proteins. As used herein, flea peritrophin nucleic acid molecules and proteins encoded by such nucleic acid molecules are also referred to as peritrophin nucleic acid molecules and proteins, or PL nucleic acid molecules and PL proteins, respectively. Flea peritrophin nucleic acid molecules and proteins of the present invention can be isolated from a flea or prepared recombinantly or synthetically. Flea peritrophin nucleic acid molecules of the present invention can be RNA or DNA, or modified forms thereof, and can be double-stranded or single-stranded; examples of nucleic acid molecules include, but are not limited to, complementary DNA (cDNA) molecules, genomic DNA molecules, synthetic DNA molecules, DNA molecules which are specific tags for messenger RNA, and corresponding mRNA molecules. As such, a flea nucleic acid molecule of the present invention is not intended refer to an entire chromosome within which such a nucleic acid molecule is contained, however, a flea peritrophin cDNA of the present invention may include all regions such as regulatory regions that control production of flea peritrophin proteins encoded by such a cDNA (such as, but not limited to, transcription, translation or post-translation control regions) as well as the coding region itself, and any introns or non-translated coding regions. As used herein, the phrase "flea peritrophin protein" refers to a protein encoded by a flea peritrophin nucleic acid molecule.

Peritrophins, including flea PL1, PL2, PL3, PL4 and PL5 proteins of the present invention, are a family of putative chitin-binding proteins that comprise a structural component of the peritrophic matrix, an acellular membrane composed of proteins and sugars, most commonly chitin which forms a barrier between the contents of an ingested meal and the gut epithelia. Flea peritrophin proteins of the present invention are characterized as containing a 6 cysteine motif, including a highly conserved motif at cysteine 2 through cysteine 3 of "CNNYYNC", where "N" represents any amino acid residue and "Y" represents an aromatic amino acid residue.

Flea peritrophin nucleic acid molecules of known length isolated from a flea, such as *Ctenocephalides felis* are denoted "nCfPL1$_\#$", for example nCfPL1$_{1096}$, wherein "#" refers to the number of nucleotides in that molecule, and flea peritrophin proteins of known length are denoted "PCfPL1$_\#$" (for example PCfPL1$_{272}$) wherein "#" refers to the number of amino acid residues in that molecule.

The present invention also provides for flea peritrophin DNA molecules that are specific tags for messenger RNA molecules. Such DNA molecules can correspond to an entire or partial sequence of a messenger RNA, and therefore, a DNA molecule corresponding to such a messenger RNA molecule (i.e. a cDNA molecule), can encode a full-length or partial-length protein. A nucleic acid molecule encoding a partial-length protein can be used directly as a probe or indirectly to generate primers to identify and/or isolate a cDNA nucleic acid molecule encoding a corresponding, or structurally related, full-length protein. Such a partial cDNA nucleic acid molecule can also be used in a similar manner to identify a genomic nucleic acid molecule, such as a nucleic acid molecule that contains the complete gene including regulatory regions, exons and introns. Methods for using partial flea peritrophin cDNA molecules and sequences to isolate full-length and corresponding cDNA molecules are described in the examples herein below.

The proteins and nucleic acid molecules of the present invention can be obtained from their natural source, or can be produced using, for example, recombinant nucleic acid technology or chemical synthesis. Also included in the present invention is the use of these proteins and nucleic acid molecules as well as antibodies and inhibitory compounds thereto as therapeutic compositions to protect animals from flea infestation as well as in other applications, such as those disclosed below.

One embodiment of the present invention is an isolated protein that includes a flea peritrophin protein. It is to be noted that the term "a" or "an" entity refers to one or more of that entity; for example, a protein, a nucleic acid molecule, an antibody and a therapeutic composition refers to "one or more" or "at least one" protein, nucleic acid molecule, antibody and therapeutic composition respectively. As such, the terms "a" (or "an"), "one or more" and "at least one" can be used interchangeably herein. It is also to be noted that the terms "comprising", "including", and "having" can be used interchangeably. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology, or can be produced by chemical synthesis.

As used herein, isolated flea peritrophin proteins of the present invention can be full-length proteins or any homologue of such proteins. An isolated protein of the present invention, including a homologue, can be identified in a straight-forward manner by the protein's ability to elicit an immune response against a flea peritrophin protein or by the protein's ability to exhibit flea peritrophin activity. Examples of flea peritrophin homologue proteins include flea peritrophin proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homologue includes at least one epitope capable of eliciting an immune response against a flea peritrophin protein, and/or of binding to an antibody directed against a flea peritrophin protein. That is, when the homologue is administered to an animal as an immunogen, using techniques known to those skilled in the art, the animal will produce an immune response against at least one epitope of a natural flea peritrophin protein. The ability of a protein to effect an immune response can be measured using techniques known to those skilled in the art. As used herein, the term "epitope" refers to the smallest portion of a protein or other antigen capable of selectively binding to the antigen binding site of an antibody or a T cell receptor. It is well accepted by those skilled in the art that the minimal size of a protein epitope is about four to six amino acids. As is appreciated by those skilled in the art, an epitope can include amino acids that naturally are contiguous to each other as well as amino acids that, due to the tertiary structure of the natural protein, are in sufficiently close proximity to form an epitope. According to the present invention, an epitope includes a portion of a protein comprising at least 4 amino acids, at least 5 amino acids, at least 6 amino acids, at least 10 amino acids, at least 15 amino acids, at least 20 amino acids, at least 25 amino acids, at least 30 amino acids, at least 35 amino acids, at least 40 amino acids or at least 50 amino acids in length.

Flea peritrophin homologue proteins can be the result of natural allelic variation or natural mutation. Flea peritrophin protein homologues of the present invention can also be produced using techniques known in the art including, but not limited to, direct modifications to the protein or modifications to the gene encoding the protein using, for example, classic or recombinant DNA techniques to effect random or targeted mutagenesis.

Flea peritrophin proteins of the present invention are encoded by flea peritrophin nucleic acid molecules. As used herein, flea peritrophin nucleic acid molecules include nucleic acid sequences related to natural flea peritrophin genes, and, preferably, to C. felis flea peritrophin genes. As used herein, flea peritrophin genes include all regions such as regulatory regions that control production of flea peritrophin proteins encoded by such genes (such as, but not limited to, transcription, translation or post-translation control regions) as well as the coding region itself, and any introns or non-translated coding regions. As used herein, a nucleic acid molecule that "includes" or "comprises" a sequence may include that sequence in one contiguous array, or may include the sequence as fragmented exons such as is often found for a flea gene. As used herein, the term "coding region" refers to a continuous linear array of nucleotides that translates into a protein. A full-length coding region is that coding region that is translated into a full-length, i.e., a complete protein as would be initially translated in its natural millieu, prior to any post-translational modifications.

One embodiment of the present invention is a C. felis flea peritrophin gene that includes the nucleic acid sequence SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, and/or SEQ ID NO:49. These nucleic acid sequences are further described herein. For example, nucleic acid sequence SEQ ID NO:1 represents the deduced sequence of the coding strand of a C. felis cDNA denoted herein as C. felis peritrophin nucleic acid molecule nCfPL1$_{1096}$, the production of which is disclosed in the Examples. Nucleic acid molecule SEQ ID NO:1 comprises an apparently full-length coding region. The complement of SEQ ID NO:1 (represented herein by SEQ ID NO:3) refers to the nucleic acid sequence of the strand fully complementary to the strand having SEQ ID NO:1, which can easily be determined by those skilled in the art. Likewise, a nucleic acid sequence complement of any nucleic acid sequence of the present invention refers to the nucleic acid sequence of the nucleic acid strand that is fully complementary to (i.e., can form a complete double helix with) the strand for which the sequence is cited. It should be noted that since nucleic acid sequencing technology is not entirely error-free, SEQ ID NO:1 (as well as other nucleic acid and protein sequences presented herein) represents an apparent nucleic acid sequence of the nucleic acid molecule encoding a flea peritrophin protein of the present invention.

Translation of SEQ ID NO:1, the coding strand of nCfPL1$_{1096}$, as well as translation of SEQ ID NO:4, the coding strand of nCfPL1$_{816}$, which represents the coding region of nCfPL1$_{1096}$, yields a protein of 272 amino acids, denoted herein as PCfPL1$_{272}$, the amino acid sequence of which is presented in SEQ ID NO:2, assuming (a) an initiation codon extending from nucleotide 6 to 8 of SEQ ID NO:1, or from nucleotide 1 to nucleotide 3 of SEQ ID NO:4, respectively; and (b) a stop codon extending from nucleotide 822 to 824 of SEQ ID NO:1.

Translation of SEQ ID NO:11, the coding strand of nCfPL2$_{1465}$, as well as translation of SEQ ID NO:14, the coding strand of nCfPL2$_{1359}$, which represents the coding region of nCfPL2$_{1465}$, yields a protein of 453 amino acids, denoted herein as PCfPL2$_{453}$, the amino acid sequence of which is presented in SEQ ID NO:12, assuming (a) an initiation codon extending from nucleotide 3 to5 of SEQ ID NO:11, or from nucleotide 1 to nucleotide 3 of SEQ ID NO:14, respectively; and (b) a stop codon extending from nucleotide 1362 to 1364 of SEQ ID NO:11.

Translation of SEQ ID NO:16, the coding strand of nCfPL3$_{387}$, as well as translation of SEQ ID NO:19, the coding strand of nCfPL3$_{243}$, which represents the coding region of nCfPL3$_{387}$, yields a protein of 81 amino acids, denoted herein as PCfPL3$_{81}$, the amino acid sequence of which is presented in SEQ ID NO:17, assuming (a) an initiation codon extending from nucleotide 20–22 of SEQ ID NO:16, or from nucleotide 1 to nucleotide 3 of SEQ ID NO:19, respectively; and (b) a stop codon extending from nucleotide 263 to 265 of SEQ ID NO:16.

Translation of SEQ ID NO:25, the coding strand of nCfPL4$_{1048}$, as well as translation of SEQ ID NO:28, the coding strand of nCfPL4$_{855}$, which represents the coding region of nCfPL4$_{1048}$, yields a protein of 285 amino acids, denoted herein as PCfP4$_{285}$, the amino acid sequence of which is presented in SEQ ID NO:26, assuming (a) an initiation codon extending from nucleotide 19–21 of SEQ ID NO:25, or from nucleotide 1 to nucleotide 3 of SEQ ID NO:28, respectively; and (b) a stop codon extending from nucleotide 874 to 876 of SEQ ID NO:25.

Translation of SEQ ID NO:42, the coding strand of nCfPL5$_{1832}$, as well as translation of SEQ ID NO:45, the coding strand of nCfPL5$_{1191}$, which represents the coding region of nCfPL5$_{1832}$, yields a protein of 397 amino acids, denoted herein as PCfPL5$_{397}$, the amino acid sequence of which is presented in SEQ ID NO:43, assuming (a) an initiation codon extending from nucleotide 146–148 of SEQ ID NO:42, or from nucleotide 1 to nucleotide 3 of SEQ ID NO:45, respectively; and (b) a stop codon extending from nucleotide 1337 to 1339 of SEQ ID NO:42.

In one embodiment, a gene or other nucleic acid molecule of the present invention can be an allelic variant that includes a similar but not identical sequence to SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, and/or SEQ ID NO:49. For example, an allelic variant of a C. felis peritrophin gene including SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, and/or SEQ ID NO:49 is a gene that occurs at essentially the same locus (or loci) in the genome as the gene including SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ iD NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, and/or SEQ ID NO:49, but which, due to natural variations caused by, for example, mutation or recombination, has a similar but not identical sequence. Because natural selection typically selects against alterations that affect function, allelic variants (i.e. alleles corresponding to, or of, cited nucleic acid sequences) usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to occur naturally within a given flea species, since the genome is diploid, and sexual reproduction will result in the reassortment of alleles.

In one embodiment of the present invention, isolated flea peritrophin proteins are encoded by nucleic acid molecules that hybridize under stringent hybridization conditions to genes or other nucleic acid molecules encoding flea peritrophin proteins, respectively. The minimal size of flea peritrophin proteins of the present invention is a size sufficient to be encoded by a nucleic acid molecule capable of forming a stable hybrid (i.e., hybridizing under stringent hybridization conditions) with the complementary sequence of a nucleic acid molecule encoding the corresponding natural protein. The size of a nucleic acid molecule encoding such a protein is dependent on the nucleic acid composition and the percent homology between the flea peritrophin nucleic acid molecule and the complementary nucleic acid sequence. It can easily be understood that the extent of homology required to form a stable hybrid under stringent conditions can vary depending on whether the homologous sequences are interspersed throughout a given nucleic acid molecule or are clustered (i.e., localized) in distinct regions on a given nucleic acid molecule.

The minimal size of a nucleic acid molecule capable of forming a stable hybrid with a gene encoding a flea peritrophin protein is at least about 12 to about 15 nucleotides in length if the nucleic acid molecule is GC-rich and at least about 15 to about 17 bases in length if it is AT-rich. The minimal size of a nucleic acid molecule used to encode a flea peritrophin protein homologue of the present invention is from about 12 to about 18 nucleotides in length. Thus, the minimal size of flea peritrophin protein homologues of the present invention is from about 4 to about 6 amino acids in length. There is no limit, other than a practical limit, on the maximal size of a nucleic acid molecule encoding a flea peritrophin protein of the present invention because a nucleic acid molecule of the present invention can include a portion of a gene or cDNA or RNA, an entire gene or cDNA or RNA, or multiple genes or cDNA or RNA. The preferred size of a protein encoded by a nucleic acid molecule of the present invention depends on whether a full-length, fusion, multivalent, or functional portion of such a protein is desired.

Stringent hybridization conditions are determined based on defined physical properties of the flea peritrophin nucleic acid molecule to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual*, Cold Spring Harbor Labs Press, and Meinkoth, et al., 1984, *Anal. Biochem.* 138, 267–284, each of which is incorporated by reference herein in its entirety. As explained in detail in the cited references, the determination of hybridization conditions involves the manipulation of a set of variables including the ionic strength (M, in moles/liter), the hybridization temperature (° C.), the concentration of nucleic acid helix destabilizing agents (such as formamide), the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m = 81.5° \text{ C.} + 16.6\log M + 0.41(\%G+C) - 500/n - 0.61(\%\text{formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d = 4(G+C) + 2(A+T).$$

A temperature of 5° C. below $T_d$ is used to detect hybridization between perfectly matched molecules.

Also well known to those skilled in the art is how base pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base pairs for hybrids greater than about 150 bp, and $T_d$ decreases about 5° C. for each mismatched base pair for hybrids below about 50 bp. Conditions for hybrids between about 50 and about 150 base pairs can be determined empirically and without undue experimentation using standard laboratory procedures well known to those skilled in the art. These simple procedures allow one skilled in the art to set the hybridization conditions (by altering, for example, the salt concentration, the helix destabilizing compound concentration or the temperature) so that only nucleic acid hybrids with greater than a specified % base pair mismatch will hybridize. Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under conditions that would allow less than or equal to 30% pair mismatch with a flea peritrophin nucleic acid molecule of about 150 bp in length or greater, the following conditions could preferably be used. The average G+C content of flea DNA is about 37%, as calculated from known flea nucleic acid sequences. The unknown nucleic acid molecules would be attached to a support membrane, and the 150 bp probe would be labeled, e.g. with a radioactive tag. The hybridization reaction could be carried out in a solution comprising 2×SSC in the absence of nucleic acid helix destabilizing compounds, at a temperature of about 37° C. (low stringency conditions). Solutions of differing concentrations of SSC can be made by one of skill in the art by diluting a stock solution of 20×SSC (175.3 gram NaCl and about 88.2 gram sodium citrate in 1 liter of water, pH 7) to obtain the desired concentration of SSC. The skilled artisan would calculate the washing conditions required to allow up to 30% base pair mismatch. For example, in a wash solution comprising 1×SSC in the absence of nucleic acid helix destabilizing compounds, the $T_m$ of perfect hybrids would be about 77° C.:

$$81.5° \text{ C.} + 16.6\log(0.15M) + (0.41 \times 73) - (500/150) - (0.61 \times 0) = 77.5° \text{ C.}$$

Thus, to achieve hybridization with nucleic acid molecules having about 30% base pair mismatch, hybridization washes would be carried out at a temperature of less than or equal to 47.5° C. It is thus within the skill of one in the art to calculate additional hybridization temperatures based on the desired percentage base pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 30% base pair mismatch will not vary significantly from 47.5° C.

Furthermore, it is known in the art that there are commercially available computer programs for determining the degree of similarity between two nucleic acid or protein sequences. These computer programs include various known methods to determine the percentage identity and the number and length of gaps between hybrid nucleic acid molecules or proteins. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, the SeqLab® Wisconsin Package™ Version 10.0-UNIX sequence analysis software, available from Genetics Computer Group, Madison, Wis. (hereinafter "SeqLab"); and DNAsis® sequence analysis software, version 2.0, available from Hitachi Software, San Bruno, Calif. (hereinafter "DNAsis"). Such software programs represent a collection of algorithms paired with a graphical user interface for using the algorithms. The DNAsis and SeqLab software, for example, employ a particular algorithm, the Needleman-Wunsch algorithm to perform pair-wise comparisons between two sequences to yield a percentage identity score, see Needleman, S. B. and Wunch, C. D., 1970, *J. Mol. Biol.*, 48, 443, which is incorporated herein by reference in its entirety. Such algorithms, including the Needleman-Wunsch algorithm, are commonly used by those skilled in the nucleic acid and amino acid sequencing art to compare sequences. A preferred method to determine percent identity among amino acid sequences and also among nucleic acid sequences includes using the Needleman-Wunsch algorithm, available in the SeqLab software, using the Pairwise Comparison/Gap function with the nwsgapdna.cmp scoring matrix, the gap creation penalty and the gap extension penalties set at default values, and the gap shift limits set at maximum (hereinafter referred to as "SeqLab default parameters"). An additional preferred method to determine percent identity among amino acid sequences and also among nucleic acid sequences includes using the Higgins-Sharp algorithm, available in the DNAsis software, with the gap penalty set at 5, the number of top diagonals set at 5, the fixed gap penalty set at 10, the k-tuple set at 2, the window size set at 5, and the floating gap penalty set at 10. A particularly preferred method to determine percent identity among amino acid sequences and also among nucleic acid sequences includes using the Needleman-Wunsch algorithm available in the SeqLab software, using the SeqLab default parameters.

One embodiment of the present invention includes a flea peritrophin protein. A preferred flea peritrophin protein includes a protein encoded by a nucleic acid molecule that hybridizes under conditions that preferably allow less than or equal to 30% base pair mismatch, preferably under conditions that allow less than or equal to 20% base pair mismatch, preferably under conditions that allow less than or equal to 10% base pair mismatch, preferably under conditions that allow less than or equal to 8% base pair mismatch, preferably under conditions that allow less than or equal to 5% base pair mismatch or preferably under conditions that allow less than or equal to 2% base pair mismatch with a nucleic acid molecule selected from the group consisting of SEQ ID NO:3, SEQ ID NO:5, SEQ ID NO:8, SEQ ID NO:10, SEQ ID NO:13, SEQ ID NO:15, SEQ ID NO:18, SEQ ID NO:20, SEQ ID NO:22, SEQ ID NO:24, SEQ ID NO:27, SEQ ID NO:29, SEQ ID NO:32, SEQ ID NO:41, SEQ ID NO:44, SEQ ID NO:46, and/or SEQ ID NO:49.

Another embodiment of the present invention includes a flea peritrophin protein encoded by a nucleic acid molecule that hybridizes under conditions comprising, (a) hybridizing in a solution comprising 1×SSC in the absence of nucleic acid helix destabilizing compounds, at a temperature of 37° C. and (b) washing in a solution comprising 1×SSC in the absence of nucleic acid helix destabilizing compounds, at a temperature of 47° C., to an isolated nucleic acid molecule selected from the group consisting of SEQ ID NO:3, SEQ ID NO:5, SEQ ID NO:8, SEQ ID NO:10, SEQ ID NO:13, SEQ ID NO:15, SEQ ID NO:18, SEQ ID NO:20, SEQ ID NO:22, SEQ ID NO:24, SEQ ID NO:27, SEQ ID NO:29, SEQ ID NO:32, SEQ ID NO:41, SEQ ID NO:44, SEQ ID NO:46, and/or SEQ ID NO:49.

Another preferred flea peritrophin protein of the present invention includes a protein that is encoded by a nucleic acid molecule that is preferably at least 70% identical, preferably at least 80% identical, preferably at least 90% identical, preferably at least 92% identical, preferably at least 95% identical or preferably at least 98% identical to a nucleic acid molecule having the nucleic acid sequence SEQ ID NO:1, SEQ ID NO:4, SEQ ID NO:6, SEQ ID NO:7, SEQ ID NO:9, SEQ ID NO:11, SEQ ID NO:14, SEQ ID NO:16, SEQ ID NO:19, SEQ ID NO:21, SEQ ID NO:23, SEQ ID NO:25, SEQ ID NO:28, SEQ ID NO:30, SEQ ID NO:33, SEQ ID NO:34, SEQ ID NO:35, SEQ ID NO:36, SEQ ID NO:37, SEQ ID NO:38, SEQ ID NO:39, SEQ ID NO:42, SEQ ID NO:45, and/or SEQ ID NO:47; also preferred are fragments (i.e. portions) of such proteins encoded by nucleic acid molecules that are at least 25 nucleotides. Percent identity as used herein is determined using the Needleman-Wunsch algorithm, available in the SeqLab software using default parameters.

Additional preferred flea peritrophin proteins of the present invention include proteins having the amino acid sequence SEQ ID NO:2, SEQ ID NO:12, SEQ ID NO:17, SEQ ID NO:26, SEQ ID NO:31, SEQ ID NO:40, SEQ ID NO:43, and/or SEQ ID NO:48, and proteins comprising homologues of a protein having the amino acid sequence SEQ ID NO:2, SEQ ID NO:12, SEQ ID NO:17, SEQ ID NO:26, SEQ ID NO:31, SEQ ID NO:40, SEQ ID NO:43, and/or SEQ ID NO:48, wherein such a homologue comprises at least one epitope that elicits an immune response against a protein having an amino acid sequence SEQ ID NO:2, SEQ ID NO:12, SEQ ID NO:17, SEQ ID NO:26, SEQ ID NO:31, SEQ ID NO:40, SEQ ID NO:43, and/or SEQ ID NO:48. Likewise, also preferred are proteins encoded by nucleic acid molecules comprising nucleic acid sequence SEQ ID NO:1, SEQ ID NO:4, SEQ ID NO:6, SEQ ID NO:7, SEQ ID NO:9, SEQ ID NO:11, SEQ ID NO:14, SEQ ID NO:16, SEQ ID NO:19, SEQ ID NO:21, SEQ ID NO:23, SEQ ID NO:25, SEQ ID NO:28, SEQ ID NO:30, SEQ ID NO:33, SEQ ID NO:34, SEQ ID NO:35, SEQ ID NO:36, SEQ ID NO:37, SEQ ID NO:38, SEQ ID NO:39, SEQ ID NO:42, SEQ ID NO:45, and/or SEQ ID NO:47, or by homologues thereof.

A preferred isolated flea peritrophin protein of the present invention is a protein encoded by at least one of the following nucleic acid molecules: $nCfPL1_{1096}$, $nCfPL1_{816}$, $nCfPL2_{445}$, $nCfPL2_{1279}$, $nCfPL2_{279}$, $nCfPL2_{1465}$, $nCfPL2_{1359}$, $nCfPL3_{387}$, $nCfPL3_{243}$, $nCfPL4_{960}$, $nCfPL4_{1029}$, $nCfPL4_{1048}$, $nCfPL4_{855}$, $nCfPL4_{802}$, $nCfPL5_{1513}$, $nCfPL5_{1832}$, $nCfPL5_{1191}$, and/or $nCfPL5_{1161}$, or allelic variants of any of these nucleic acid molecules. Also preferred is an isolated protein encoded by a nucleic acid molecule having nucleic acid sequence SEQ ID NO:1, SEQ ID NO:4, SEQ ID NO:6, SEQ ID NO:7, SEQ ID NO:9, SEQ ID NO:11, SEQ ID NO:14, SEQ ID NO:16, SEQ ID NO:19, SEQ ID NO:21, SEQ ID NO:23, SEQ ID NO:25, SEQ ID NO:28, SEQ ID NO:30, SEQ ID NO:33, SEQ ID NO:34, SEQ ID NO:35, SEQ ID NO:36, SEQ ID NO:37, SEQ ID NO:38, SEQ ID NO:39, SEQ ID NO:42, SEQ ID NO:45, and/or SEQ ID NO:47; or a protein encoded by an allelic variant of any of these listed nucleic acid molecules.

Preferred flea peritrophin proteins of the present invention include proteins having amino acid sequences that are at least 70%, preferably 80%, preferably 90%, preferably 92%, preferably 95%, preferably at least 98%, preferably at least 99%, or preferably 100% identical to amino acid sequence SEQ ID NO:2, SEQ ID NO:12, SEQ ID NO:17, SEQ ID NO:26, SEQ ID NO:31, SEQ ID NO:40, SEQ ID NO:43, and/or SEQ ID NO:48; and proteins encoded by allelic variants of nucleic acid molecules encoding flea peritrophin proteins having amino acid sequences SEQ ID NO:2, SEQ ID NO:12, SEQ ID NO:17, SEQ ID NO:26, SEQ ID NO:31, SEQ ID NO:40, SEQ ID NO:43, and/or SEQ ID NO:48. Also preferred are fragments thereof having at least 10 amino acid residues.

In one embodiment of the present invention, C. felis peritrophin proteins comprise amino acid sequence SEQ ID NO:2, SEQ ID NO:12, SEQ ID NO:17, SEQ ID NO:26, SEQ ID NO:31, SEQ ID NO:40, SEQ ID NO:43, and/or SEQ ID NO:48 (including, but not limited to, the proteins consisting of amino acid sequence SEQ ID NO:2, SEQ ID NO:12, SEQ ID NO:17, SEQ ID NO:26, SEQ ID NO:31, SEQ ID NO:40, SEQ ID NO:43, and/or SEQ ID NO:48, fusion proteins and multivalent proteins), and proteins encoded by allelic variants of nucleic acid molecules encoding proteins having amino acid sequence SEQ ID NO:2, SEQ ID NO:12, SEQ ID NO:17, SEQ ID NO:26, SEQ ID NO:31, SEQ ID NO:40, SEQ ID NO:43, and/or SEQ ID NO:48.

In one embodiment, a preferred flea peritrophin protein comprises an amino acid sequence of at least 6 amino acids, preferably at least 10 amino acids, preferably at least 15 amino acids, preferably at least 20 amino acids, preferably at least 25 amino acids, preferably at least 30 amino acids, preferably at least 35 amino acids, preferably at least 40 amino acids, preferably at least 50 amino acids, preferably at least 75 amino acids, preferably at least 100 amino acids, preferably at least 125 amino acids, preferably at least 150 amino acids, preferably at least 175 amino acids, preferably at least 200 amino acids, preferably at least 250 amino acids, preferably at least 300 amino acids, preferably at least 350 amino acids, preferably at least 400 amino acids, or preferably at least 450 amino acids. In another embodiment, preferred flea peritrophin proteins comprise full-length proteins, i.e., proteins encoded by full-length coding regions, or post-translationally modified proteins thereof, such as mature proteins from which initiating methionine and/or signal sequences or "pro" sequences have been removed.

Additional preferred flea peritrophin proteins of the present invention include proteins encoded by nucleic acid molecules comprising at least a portion of $nCfPL1_{1096}$, $nCfPL1_{816}$, $nCfPL2_{445}$, $nCfPL2_{1279}$, $nCfPL2_{279}$, $nCfPL2_{1465}$, $nCfPL2_{1359}$, $nCfPL3_{387}$, $nCfPL3_{243}$, $nCfPL4_{960}$, $nCfPL4_{1029}$, $nCfPL4_{1048}$, $nCfPL4_{855}$, $nCfPL4_{802}$, $nCfPL5_{1513}$, $nCfPL5_{1832}$, $nCfPL5_{1191}$, and/or $nCfPL5_{1161}$, as well as flea peritrophin proteins encoded by allelic variants of such nucleic acid molecules. A portion of such flea peritrophin nucleic acid molecule is preferably at least 25 nucleotides in length.

Also preferred are flea peritrophin proteins encoded by nucleic acid molecules having nucleic acid sequences comprising at least a portion of SEQ ID NO:1, SEQ ID NO:4, SEQ ID NO:6, SEQ ID NO:7, SEQ ID NO:9, SEQ ID NO:11, SEQ ID NO:14, SEQ ID NO:16, SEQ ID NO:19, SEQ ID NO:21, SEQ ID NO:23, SEQ ID NO:25, SEQ ID NO:28, SEQ ID NO:30, SEQ ID NO:33, SEQ ID NO:34, SEQ ID NO:35, SEQ ID NO:36, SEQ ID NO:37, SEQ ID NO:38, SEQ ID NO:39, SEQ ID NO:42, SEQ ID NO:45, and/or SEQ ID NO:47, as well as allelic variants of these nucleic acid molecules. A portion of such flea peritrophin nucleic acid molecule is preferably at least 25 nucleotides in length.

In another embodiment, a preferred flea peritrophin protein of the present invention is encoded by a nucleic acid molecule comprising at least 20 nucleotides, preferably at least 25 nucleotides, preferably at least 30 nucleotides, preferably at least 40 nucleotides, preferably at least 50 nucleotides, preferably at least 75 nucleotides, preferably at least 100 nucleotides, preferably at least 125 nucleotides, preferably at least 150 nucleotides, preferably at least 175 nucleotides, preferably at least 200 nucleotides, preferably at least 250 nucleotides, preferably at least 350 nucleotides, preferably at least 450 nucleotides, preferably at least 550 nucleotides, preferably at least 650 nucleotides, preferably at least 750 nucleotides, preferably at least 1000 nucleotides, preferably at least 1100 nucleotides, preferably at least 1200 nucleotides, preferably at least 1500 nucleotides, preferably at least 1750 nucleotides, or preferably at least 1850 nucleotides in length. Within this embodiment is a flea peritrophin protein encoded by at least a portion of $nCfPL1_{1096}$, $nCfPL1_{816}$, $nCfPL2_{445}$, $nCfPL2_{1279}$, $nCfPL2_{279}$, $nCfPL2_{1465}$, $nCfPL2_{1359}$, $nCfPL3_{387}$, $nCfPL3_{243}$, $nCfPL4_{960}$, $nCfPL4_{1029}$, $nCfPL4_{1048}$, $nCfPL4_{855}$, $nCfPL4_{802}$, $nCfPL5_{1513}$, $nCfPL5_{1832}$, $nCfPL5_{1191}$, and/or $nCfPL5_{1161}$, or by an an allelic variant of any of these nucleic acid molecules. Preferred flea peritrophin proteins of the present invention are encoded by nucleic acid molecules comprising apparently full-length flea peritrophin coding region, i.e., nucleic acid molecules encoding an apparently full-length flea peritrophin protein.

Preferred flea peritrophin proteins of the present invention can be used to develop inhibitors that, when administered to an animal in an effective manner, are capable of protecting that animal from flea infestation. In accordance with the present invention, the ability of an inhibitor of the present invention to protect an animal from flea infestation refers to the ability of that protein to, for example, treat, ameliorate and/or prevent infestation caused by fleas. In particular, the phrase "to protect an animal from flea infestation" refers to reducing the potential for flea population expansion on and around the animal (i.e., reducing the flea burden). Preferably, the flea population size is decreased, optimally to an extent that the animal is no longer bothered by fleas. A host animal, as used herein, is an animal from which fleas can feed by attaching to and feeding through the skin of the animal. Fleas, and other ectoparasites, can live on a host animal for an extended period of time or can attach temporarily to an animal in order to feed. At any given time, a certain percentage of a flea population can be on a host animal whereas the remainder can be in the environment of the animal. Such an environment can include not only adult fleas, but also flea eggs and/or flea larvae. The environment can be of any size such that fleas in the environment are able to jump onto and off of a host animal. For example, the environment of an animal can include plants, such as crops, from which fleas infest an animal. As such, it is desirable not only to reduce the flea burden on an animal per se, but also to reduce the flea burden in the environment of the animal.

Suitable fleas to target include any flea that is essentially incapable of causing disease in an animal administered an inhibitor of the present invention. As such, fleas to target include any flea that produces a protein that can be targeted by an inhibitory compound that inhibits a flea flea peritrophin protein function, thereby resulting in the decreased ability of the parasite to cause disease in an animal. Preferred fleas to target include fleas of the following genera: Ctenocephalides, Cyopsyllus, Diamanus (Oropsylla), Echidnophaga, Nosopsyllus, Pulex, Tunga, and Xenopsylla, with those of the species *Ctenocephalides canis, Ctenocephalides felis, Diamanus montanus, Echidnophaga gallinacea, Nosopsyllus faciatus, Pulex irritans, Pulex simulans, Tunga penetrans* and *Xenopsylla cheopis* being more preferred, with *C. felis* being even more preferred. Such fleas are also preferred for the isolation of proteins or nucleic acid molecules of the present invention.

One embodiment of a flea peritrophin protein of the present invention is a fusion protein that includes a flea peritrophin protein-containing domain attached to one or more fusion segments. Suitable fusion segments for use with the present invention include, but are not limited to, segments that can: enhance a protein's stability; act as an immunopotentiator; and/or assist in purification of a flea peritrophin protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the flea peritrophin-containing domain of the protein and can be susceptible to cleavage in order to enable straight-forward recovery of a flea peritrophin protein. Fusion proteins are preferably produced by culturing a recombinant cell transformed with a fusion nucleic acid molecule that encodes a protein including the fusion segment attached to either the carboxyl and/or amino terminal end of a flea peritrophin-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7 tag peptide, a Flag™ peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide.

The present invention also includes mimetopes of flea peritrophin proteins of the present invention. As used herein, a mimetope of a flea peritrophin protein of the present invention refers to any compound that is able to mimic the activity of such a flea peritrophin protein, often because the mimetope has a structure that mimics the particular flea peritrophin protein. Mimetopes can be, but are not limited to: peptides that have been modified to decrease their susceptibility to degradation such as all-D retro peptides; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

Another embodiment of the present invention is an isolated nucleic acid molecule comprising a flea peritrophin nucleic acid molecule, i.e. a nucleic acid molecule that can be isolated from a flea cDNA library. As used herein, flea peritrophin nucleic acid molecules has the same meaning as flea peritrophin nucleic acid molecule. The identifying characteristics of such nucleic acid molecules are heretofore described. A nucleic acid molecule of the present invention can include an isolated natural flea peritrophin gene or a homologue thereof, the latter of which is described in more detail below. A nucleic acid molecule of the present invention can include one or more regulatory regions, full-length or partial coding regions, or combinations thereof. The minimal size of a nucleic acid molecule of the present invention is a size sufficient to allow the formation of a stable hybrid (i.e., hybridization under stringent hybridization conditions) with the complementary sequence of another nucleic acid molecule. As such, the minimal size of a flea peritrophin nucleic acid molecule of the present invention is from 12 to 18 nucleotides in length.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As such, "isolated" does not reflect the extent to which the nucleic acid molecule has been purified. Isolated flea peritrophin nucleic acid molecules of the present invention, or homologues thereof, can be isolated from a natural source or produced using recombinant DNA technology (e.g., polymerase chain reaction (PCR) amplification or cloning) or chemical synthesis. Isolated flea peritrophin nucleic acid molecules, and homologues thereof, can include, for example, natural allelic variants and nucleic acid molecules modified by nucleotide insertions, deletions, substitutions, and/or inversions in a manner such that the modifications do not substantially interfere with the nucleic acid molecule's ability to encode a flea peritrophin protein of the present invention.

A flea peritrophin nucleic acid molecule homologue can be produced using a number of methods known to those skilled in the art, see, for example, Sambrook et al., ibid., which is incorporated by reference herein in its entirety. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecule homologues can be selected by hybridization with flea peritrophin nucleic acid molecules or by screening the function of a protein encoded by the nucleic acid molecule (e.g., ability to elicit an immune response against at least one epitope of a flea peritrophin protein, to selectively bind to an antibody that binds a flea peritrophin protein or to effect flea peritrophin activity).

An isolated flea peritrophin nucleic acid molecule of the present invention can include a nucleic acid sequence that encodes at least one flea peritrophin protein of the present invention respectively, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a flea peritrophin protein.

A preferred nucleic acid molecule of the present invention, when administered to an animal, is capable of protecting that animal from flea infestation. As will be disclosed in more detail below, a nucleic acid molecule of the present invention can be, or encode, an antisense RNA, a molecule capable of triple helix formation, a ribozyme, or other nucleic acid-based drug compound. In additional embodiments, a nucleic acid molecule of the present invention can encode a protective protein (e.g., a flea peritrophin protein of the present invention), the nucleic acid molecule being delivered to the animal, for example, by direct injection (i.e, as a genetic vaccine) or in a vehicle such as a recombinant virus vaccine or a recombinant cell vaccine.

In one embodiment of the present invention, a preferred flea peritrophin nucleic acid molecule includes an isolated nucleic acid molecule that hybridizes under conditions that preferably allow less than or equal to 30% base pair mismatch, preferably under conditions that allow less than or equal to 20% base pair mismatch, preferably under conditions that allow less than or equal to 10% base pair mismatch preferably under conditions that allow less than or equal to 5% base pair mismatch or preferably under conditions that allow less than or equal to 2% base pair mismatch with a nucleic acid molecule selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ IDNO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, and/or SEQ ID NO:49.

Another embodiment of the present invention includes a flea peritrophin nucleic acid molecule, wherein said nucleic acid molecule hybridizes under conditions comprising, (a) hybridizing in solution comprising 1×SSC in the absence of nucleic acid helix destabilizing compounds, at a temperature of 37° C. and (b) washing in a solution comprising 1×SSC in the absence of nucleic acid helix destabilizing compounds, at a temperature of 47° C., to an isolated nucleic acid molecule selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, and/or SEQ ID NO:49. Additional preferred nucleic acid molecules of the present invention include oligonucleotides of an isolated nucleic acid molecule, wherein said nucleic acid molecule hybridizes under conditions comprising, (a) hybridizing in solution comprising 1×SSC in the absence of nucleic acid helix destabilizing compounds, at a temperature of 37° C. and (b) washing in a solution comprising 1×SSC in the absence of nucleic acid helix destabilizing compounds, at a temperature of 47° C., to an isolated nucleic acid molecule selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, and/or SEQ ID NO:49, wherein said oligonucleotide comprises at least 25 nucleotides.

Additional preferred flea peritrophin nucleic acid molecules of the present invention include nucleic acid molecules comprising a nucleic acid sequence that is preferably at least 70%, preferably at least 80%, preferably at least 90%, preferably at least 92%, preferably at least 95%, or preferably at least 98% identical to a nucleic acid sequence selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, and/or SEQ ID NO:49. Also preferred are oligonucleotides of any of such nucleic acid molecules. Percent identity as used herein is determined using the Needleman-Wunsch algorithm, available in the SeqLab software using default parameters.

One embodiment of the present invention is a nucleic acid molecule comprising all or part of nucleic acid molecules $nCfPL1_{1096}$, $nCfPL1_{816}$, $nCfPL2_{445}$, $nCfPL2_{1279}$, $nCfPL2_{279}$, $nCfPL2_{1465}$, $nCfPL2_{1359}$, $nCfPL3_{387}$, $nCfPL3_{243}$, $nCfPL4_{960}$, $nCfPL4_{1029}$, $nCfPL4_{1048}$, $nCfPL4_{855}$, $nCfPL4_{802}$, $nCfPL5_{1513}$, $nCfPL5_{1832}$, $nCfPL5_{1191}$, and/or $nCfPL5_{1161}$, or allelic variants of these nucleic acid molecules. Another preferred nucleic acid molecule of the present invention includes at least a portion of nucleic acid sequence SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, and/or SEQ ID NO:49, as well as allelic variants of nucleic acid molecules having these nucleic acid sequences and homologues of nucleic acid molecules having these nucleic acid sequences; preferably such a homologue encodes or is complementary to a nucleic acid molecule that encodes at least one epitope that elicits an immune response against a protein having an amino acid sequence SEQ ID NO:2, SEQ ID NO:12, SEQ ID NO:17, SEQ ID NO:26, SEQ ID NO:31, SEQ ID NO:40, SEQ ID NO:43, and/or SEQ ID NO:48. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound.

In one embodiment, a flea peritrophin nucleic acid molecule of the present invention encodes a protein having an amino acid sequence that is at least 70%, preferably at least 80%, preferably at least 90%, preferably at least 95%, preferably at least 98%, preferably at least 99%, or preferably at least 100% identical to SEQ ID NO:2, SEQ ID NO:12, SEQ ID NO:17, SEQ ID NO:26, SEQ ID NO:31, SEQ ID NO:40, SEQ ID NO:43, and/or SEQ ID NO:48. The present invention also includes a flea peritrophin nucleic acid molecule encoding a protein having at least a portion of SEQ ID NO:2, SEQ ID NO:12, SEQ ID NO:17, SEQ ID NO:26, SEQ ID NO:31, SEQ ID NO:40, SEQ ID NO:43, and/or SEQ ID NO:48, as well as allelic variants of a nucleic acid molecule encoding a protein having these sequences, including nucleic acid molecules that have been modified to accommodate codon usage properties of the cells in which such nucleic acid molecules are to be expressed.

In another embodiment, a preferred flea peritrophin nucleic acid molecule of the present invention comprises a nucleic acid molecule comprising at least 20 nucleotides, preferably at least 25 nucleotides, preferably at least 30 nucleotides, preferably at least 40 nucleotides, preferably at least 50 nucleotides, preferably at least 75 nucleotides, preferably at least 100 nucleotides, preferably at least 125 nucleotides, preferably at least 150 nucleotides, preferably at least 175 nucleotides, preferably at least 200 nucleotides, preferably at least 250 nucleotides, preferably at least 350 nucleotides, preferably at least 450 nucleotides, preferably at least 550 nucleotides, preferably at least 650 nucleotides, preferably at least 750 nucleotides, preferably at least 1000 nucleotides, preferably at least 1100 nucleotides, preferably at least 1200 nucleotides, preferably at least 1500 nucleotides, preferably at least 1750 nucleotides, or preferably at least 1850 nucleotides in length.

In another embodiment, a preferred flea peritrophin nucleic acid molecule encodes a protein comprising at least 6 amino acids, preferably at least 10 amino acids, preferably at least 20 amino acids, preferably at least 30 amino acids, preferably at least 40 amino acids, preferably at least 50 amino acids, preferably at least 75 amino acids, preferably at least 100 amino acids, preferably at least 200 amino acids, preferably at least 300 amino acids, preferably at least 400 amino acids, or preferably at least 450 amino acids.

In another embodiment, a preferred flea peritrophin nucleic acid molecule of the present invention comprises an apparently full-length flea peritrophin coding region, i.e., the preferred nucleic acid molecule encodes an apparently full-length flea peritrophin protein, respectively, or a post-translationally modified protein thereof. In one embodiment, a preferred flea peritrophin nucleic acid molecule of the present invention encodes a mature protein.

In another embodiment, a preferred flea peritrophin nucleic acid molecule of the present invention comprises a nucleic acid molecule comprising SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, and/or SEQ ID NO:49, or a fragment thereof.

A fragment of a flea peritrophin nucleic acid molecule of the present invention preferably comprises at least 15 nucleotides, preferably at least 18 nucleotides, preferably at least 21 nucleotides, preferably at least 25 nucleotides, preferably at least 30 nucleotides, preferably at least 35 nucleotides, preferably at least 40 nucleotides, preferably at least 50 nucleotides, preferably at least 75 nucleotides, preferably at least 100 nucleotides, preferably at least 125 nucleotides, preferably at least 150 nucleotides, preferably at least 175 nucleotides, preferably at least 200 nucleotides, preferably at least 250 nucleotides, preferably at least 350 nucleotides, preferably at least 450 nucleotides, preferably at least 550 nucleotides, preferably at least 650 nucleotides, preferably at least 750 nucleotides, preferably at least 1000 nucleotides, preferably at least 1100 nucleotides, preferably at least 1200 nucleotides, preferably at least 1500 nucleotides, preferably at least 1750 nucleotides, or preferably at least 1850 nucleotides identical in sequence to a corresponding contiguous sequence selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, and/or SEQ ID NO:49.

The phrase, a nucleic acid molecule comprising at least "x" contiguous, or consecutive nucleotides identical in sequence to at least "x" contiguous, or consecutive nucleotides of a nucleic acid molecule selected from the group consisting of SEQ ID NO:"y", refers to an "x"-nucleotide in length nucleic acid molecule that is identical in sequence to an "x"-nucleotide portion of SEQ ID NO:"y", as well as to nucleic acid molecules that are longer in length than "x". The additional length may be in the form of nucleotides that extend from either the 5' or the 3' end(s) of the contiguous identical "x"-nucleotide portion. The 5' and/or 3' extensions can include one or more extensions that have no identity to a molecule of the present invention, as well as extensions that show similarity or identity to cited nucleic acids sequences or portions thereof.

Knowing the nucleic acid sequences of certain flea peritrophin nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other flea peritrophin nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include cDNA libraries as well as genomic DNA libraries. Similarly, preferred DNA sources to screen or from which to amplify nucleic acid molecules include cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising *C. felis* peritrophin nucleic acid molecules or other flea peritrophin nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of preferably 100 to 200 nucleotides. The present invention includes oligonucleotides that can be used as, for example, probes to identify nucleic acid molecules, primers to produce nucleic acid molecules, or therapeutic reagents to inhibit flea peritrophin protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of flea peritrophin nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, insect and mammalian cells, and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences that control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those that function in bacterial, yeast, or insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with fleas, such as *C. felis* transcription control sequences.

Suitable and preferred nucleic acid molecules to include in recombinant vectors of the present invention are as disclosed herein. Preferred nucleic acid molecules to include in recombinant vectors, and particularly in recombinant molecules, include $nCfPL1_{1096}$, $nCfPL1_{816}$, $nCfPL2_{445}$, $nCfPL2_{1279}$, $nCfPL2_{279}$, $nCfPL2_{1465}$, $nCfPL2_{1359}$, $nCfPL3_{387}$, $nCfPL3_{243}$, $nCfPL4_{960}$, $nCfPL4_{1029}$, $nCfPL4_{1048}$, $nCfPL4_{855}$, $nCfPL4_{802}$, $nCfPL5_{1513}$, $nCfPL5_{1832}$, $nCfPL5_{1191}$, and/or $nCfPL5_{1161}$.

Recombinant molecules of the present invention may also (a) contain secretory signals (i.e., signal segment nucleic acid sequences) to enable an expressed flea peritrophin protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. It is to be noted that a cell line refers to any recombinant cell of the present invention that is not a transgenic animal. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include flea peritrophin nucleic acid molecules disclosed herein. Preferred nucleic acid molecules with which to transform a cell include $nCfPL1_{1096}$, $nCfPL1_{816}$, $nCfPL2_{445}$, $nCfPL2_{1279}$, $nCfPL2_{279}$, $nCfPL2_{1465}$, $nCfPL2_{1359}$, $nCfPL3_{387}$, $nCfPL3_{243}$, $nCfPL4_{960}$, $nCfPL4_{1029}$, $nCfPL4_{1048}$, $nCfPL4_{855}$, $nCfPL4_{802}$, $nCfPL5_{1513}$, $nCfPL5_{1832}$, $nCfPL5_{1191}$, and/or $nCfPL5_{1161}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing flea peritrophin proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, insect and mammalian cells. More preferred host cells include Salmonella, Escherichia, Bacillus, Caulobacter, Listeria, Saccharomyces, Pichia, Spodoptera, Mycobacteria, Trichoplusia, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, and Vero cells. Particularly preferred host cells are *Escherichia coli,* including *E. coli* K-12 derivatives; *Salmonella typhi; Salmonella typhimurium,* including attenuated strains such as UK-1$_x$3987 and SR-11$_x$4072; Caulobacter; Pichia; *Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein. The phrase operatively linked refers to insertion of a nucleic acid molecule into an expression vector in a manner such that the molecule is able to be expressed when transformed into a host cell.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transformed with one or more recombinant molecules including flea peritrophin nucleic acid molecules encoding one or more proteins of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated flea peritrophin proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce a flea peritrophin protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in *E. coli;* or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a flea peritrophin protein of the present invention or a mimetope thereof (e.g., anti-flea peritrophin antibodies). As used herein, the term "selectively binds to" a protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid., and Harlow, et al., 1988, *Antibodies, a Laboratory Manual*, Cold Spring Harbor Labs Press; Harlow et al., ibid., is incorporated by reference herein in its entirety. An anti-flea peritrophin antibody of the present invention preferably selectively binds to a flea peritrophin protein, respectively, in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce flea peritrophin proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from fleas susceptible to treatment by such antibodies and/or (b) as tools to screen expression libraries and/or to recover desired proteins of the present invention from a mixture of proteins and other contaminants. Furthermore, antibodies of the present invention can be used to target cytotoxic agents to fleas in order to directly kill such fleas. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal susceptible to flea infestation, is capable of protecting that animal from flea infestation. Therapeutic compositions of the present invention include at least one of the following protective molecules: an isolated flea peritrophin protein; a mimetope of an isolated flea peritrophin protein; an isolated flea peritrophin nucleic acid molecule; and/or a compound derived from said isolated flea peritrophin protein that inhibits flea peritrophin protein activity. A therapeutic composition of the present invention can further comprise a component selected from the group of an excipient, a carrier, and/or an adjuvant; these components are described further herein. As used herein, a protective molecule or protective compound refers to a compound that, when administered to an animal in an effective manner, is able to treat, ameliorate, and/or prevent flea infestation. Preferred fleas to target are heretofore disclosed. One example of a protective molecule is a vaccine, such as, but not limited to, a naked nucleic acid vaccine, a recombinant virus vaccine, a recombinant cell vaccine, and a recombinant protein vaccine. Another example of a protective molecule is a compound that inhibits flea peritrophin protein activity, such as an isolated antibody that selectively binds to a flea peritrophin protein, a substrate analog of a flea peritrophin protein, anti-sense-, triplex formation-, ribozyme-, and/or RNA drug-based compounds, or other inorganic or organic molecules that inhibit flea peritrophin protein activity. Inhibiting flea peritrophin protein activity can refer to the ability of a compound to reduce the activity of flea peritrophin proteins. Inhibiting flea peritrophin protein activity can also refer to the ability of a compound to reduce the amount of flea peritrophin protein in a flea.

One embodiment of the present invention is a therapeutic composition comprising an excipient and a compound selected from the group consisting of: (a) an isolated nucleic acid molecule selected from the group consisting of a flea cDNA molecule and a flea RNA molecule, wherein said nucleic acid molecule is selected from the group consisting of (a) a nucleic acid molecule at least 25 nucleotides in length that hybridizes with a nucleic acid molecule having a nucleic acid sequence selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:27, SEQ ID NO:28, SEQ ID NO:29, SEQ ID NO:30, and SEQ ID NO:32, and (b) a nucleic acid molecule at least 35 nucleotides in length that hybridizes with a nucleic acid molecule having a nucleic acid sequence selected from the group consisting of SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, and SEQ ID NO:49; wherein said hybridization of (a) and (b) is performed under conditions comprising (1) hybridizing in a solution comprising 1×SSC in the absence of nucleic acid helix destabilizing compounds, at a temperature of 37° C. and (2) washing in a solution comprising 1×SSC in the absence of helix destabilizing compounds, at a temperature of 47° C.; (b) an isolated protein selected from the group consisting of (1) a protein encoded by a nucleic acid molecule selected from the group consisting of (i) a nucleic acid molecule at least 25 nucleotides in length that hybridizes with a nucleic acid molecule having a nucleic acid sequence selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:27, SEQ ID NO:28, SEQ ID NO:29, SEQ ID NO:30, and SEQ ID NO:32, and (ii) a nucleic acid molecule at least 35 nucleotides in length that hybridizes with a nucleic acid molecule having a nucleic acid sequence selected from the group consisting of SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, and SEQ ID NO:49; wherein said hybridization of (i) and (ii) is performed under conditions comprising (a) hybridizing in a solution comprising 1×SSC in the absence of nucleic acid helix destabilizing compounds, at a temperature of 37° C. and (b) washing in a solution comprising 1×SSC in the absence of helix destabilizing compounds, at a temperature of 47° C.; and (2) an isolated protein, comprising at least 10 amino acids identical in sequence to a 10 amino acid portion of an amino acid sequence selected from the group consisting of SEQ ID NO:2, SEQ ID NO:12, SEQ ID NO:17, SEQ ID NO:26, SEQ ID NO:31, SEQ ID NO:40, SEQ ID NO:43, and SEQ ID NO:48; and (c) an isolated antibody that selectively binds to a protein as set forth in (b).

Another embodiment of the present invention includes a method to reduce flea infestation in an animal susceptible to flea infestation. Such a method includes the step of administering to the animal a therapeutic molecule comprising a protective compound selected from the group consisting of (a) an isolated flea peritrophin protein; (b) a mimetope of an isolated flea peritrophin protein; (c) an isolated flea peritrophin nucleic acid molecule; and (d) a compound derived from an isolated flea peritrophin protein that inhibits flea peritrophin protein activity.

Therapeutic compositions of the present invention can be administered to any animal susceptible to flea infestation, preferably to mammals, and more preferably to dogs, cats, humans, ferrets, horses, cattle, sheep, and other pets, economic food animals, work animals and/or zoo animals. Preferred animals to protect against flea infestation include dogs, cats, humans, and ferrets, with dogs and cats being particularly preferred.

As used herein, the term derived, or the term derived from, refers to a peptide, antibody, mimetope, nucleic acid molecule, or other compound that was obtained from or using a flea peritrophin protein or nucleic acid molecule of the present invention. Methods to obtain derivatives from a flea peritrophin molecule of the present invention are known in the art, and as such include, but are not limited to molecular modeling of flea peritrophin proteins to determine active sites, and predicting from these active sites smaller fragments and/or mimetopes that retain and/or mimic these active sites, thereby inhibiting flea peritrophin protein activity. Other inhibitors of flea peritrophin activity can also be obtained in a variety of ways, including but not limited to screening of peptide or small chemical compound libraries against flea peritrophin proteins of the present invention; and screening of polyclonal or monoclonal antibodies to find antibodies that specifically bind flea peritrophin proteins of the present invention.

A flea peritrophin protein inhibitor of the present invention (i.e. an inhibitor of a flea peritrophin protein) is identified by its ability to mimic, bind to, modify, or otherwise interact with, a flea peritrophin protein, thereby inhibiting the activity of a natural flea peritrophin protein. Suitable inhibitors of flea peritrophin protein activity are compounds that inhibit flea peritrophin protein activity in at least one of a variety of ways: (a) by binding to or otherwise interacting with or otherwise modifying flea peritrophin protein sites; (b) by binding to the flea peritrophin protein and thus reducing the availability of the flea peritrophin protein in solution; (c) by mimicking a flea peritrophin protein; and (d) by interacting with other regions of the flea peritrophin protein to inhibit flea peritrophin protein activity, for example, by allosteric interaction.

Flea peritrophin protein inhibitors can be used directly as compounds in compositions of the present invention to treat animals as long as such compounds are not harmful to host animals being treated. Preferred flea peritrophin protein inhibitors of the present invention include, but are not limited to, flea peritrophin protein substrate analogs, and other molecules that bind to a flea peritrophin protein (e.g., to an allosteric site) in such a manner that the activity of the flea peritrophin protein is inhibited. A flea peritrophin protein substrate analog refers to a compound that interacts with (e.g., binds to, associates with, modifies) the active site of a flea peritrophin protein. A preferred flea peritrophin protein substrate analog inhibits flea peritrophin protein activity. Flea peritrophin protein substrate analogs can be of any inorganic or organic composition. Flea peritrophin protein substrate analogs can be, but need not be, structurally similar to a flea peritrophin protein natural substrate as long as they can interact with the active site of that flea peritrophin protein. Flea peritrophin protein substrate analogs can be designed using computer-generated structures of flea peritrophin proteins of the present invention or computer structures of flea peritrophin protein's natural substrates. Preferred sites to model include one or more of the active sites of flea peritrophin proteins. Substrate analogs can also be obtained by generating random samples of molecules, such as oligonucleotides, peptides, peptidomimetic compounds, or other inorganic or organic molecules, and screening such samples for their ability to interfere with interaction between flea peritrophin proteins and their substrates, e.g. by affinity chromatography techniques. A preferred flea peritrophin protein substrate analog is a flea peritrophin protein mimetic compound, i.e., a compound that is structurally and/or functionally similar to a natural substrate of a flea peritrophin protein of the present invention, particularly to the region of the substrate that interacts with the flea peritrophin protein active site, but that inhibits flea peritrophin protein activity upon interacting with the flea peritrophin protein active site.

The present invention also includes a therapeutic composition comprising at least one protective molecule of the present invention in combination with at least one additional compound protective against one or more infectious agents.

In one embodiment, a therapeutic composition of the present invention can be used to protect an animal from flea infestation by administering such composition to a flea in order to prevent infestation. Such administration to the flea and/or animal could be oral, or by application to the animal's body surface (e.g. topical spot-on, or spraying onto the animal), or by application to the environment (e.g., spraying). Examples of such compositions include, but are not limited to, transgenic vectors capable of producing at least one therapeutic composition of the present invention. In another embodiment a flea can ingest therapeutic compositions, or products thereof, present on the surface of or in the blood of a host animal that has been administered a therapeutic composition of the present invention.

In accordance with the present invention, a host animal (i.e., an animal that is or is capable of being infested with fleas) is treated by administering to the animal a therapeutic composition of the present invention in such a manner that the composition itself (e.g., a flea peritrophin protein, a flea peritrophin nucleic acid molecule, a flea peritrophin protein inhibitor, a peritrophin protein synthesis suppressor (i.e., a compound that decreases the production or half-life of a peritrophin protein in fleas), a flea peritrophin protein mimetope, or a anti-flea peritrophin antibody) or a product generated by the animal in response to administration of the composition (e.g., antibodies produced in response to administration of a flea peritrophin protein or nucleic acid molecule, or conversion of an inactive inhibitor "prodrug" to an active flea peritrophin protein inhibitor) ultimately enters the flea. A host animal is preferably treated in such a way that the compound or product thereof is present on the body surface of the animal or enters the blood stream of the animal. Fleas are then exposed to the composition or product when they feed from the animal. For example, flea peritrophin protein inhibitors administered to an animal are administered in such a way that the inhibitors enter the blood stream of the animal, where they can be taken up by feeding fleas.

The present invention also includes the ability to reduce larval flea infestation in that when fleas feed from a host animal that has been administered a therapeutic composition of the present invention, at least a portion of compounds of the present invention, or products thereof, in the blood taken up by the fleas are excreted by the fleas in feces, which is subsequently ingested by flea larvae. In particular, it is of note that flea larvae obtain most, if not all, of their nutrition from flea feces.

In accordance with the present invention, reducing flea peritrophin protein activity in a flea can lead to a number of outcomes that reduce flea burden on treated animals and their surrounding environments. Such outcomes include, but are not limited to, (a) reducing the viability of fleas that feed from the treated animal, (b) reducing the fecundity of female fleas that feed from the treated animal, (c) reducing the reproductive capacity of male fleas that feed from the treated animal, (d) reducing the viability of eggs laid by female fleas that feed from the treated animal, (e) altering the blood feeding behavior of fleas that feed from the treated animal (e.g., fleas take up less volume per feeding or feed less frequently), (f) reducing the viability of flea larvae, for example due to the feeding of larvae from feces of fleas that feed from the treated animal, (g) altering the development of flea larvae (e.g., by decreasing feeding behavior, inhibiting growth, inhibiting (e.g., slowing or blocking) molting, and/or otherwise inhibiting maturation to adults), and/or (h) altering or decreasing the ability of fleas or flea larvae to digest a blood meal.

In order to protect an animal from flea infestation, a therapeutic composition of the present invention is administered to the animal in an effective manner such that the composition is capable of protecting that animal from flea infestation. Therapeutic compositions of the present invention can be administered to animals prior to infestation in order to prevent infestation (i.e., as a preventative vaccine) and/or can be administered to animals after infestation. For example, proteins, mimetopes thereof, and antibodies thereof can be used as immunotherapeutic agents.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), Flt-3 ligand, granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), and Leishmania elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition. The therapeutic composition is preferably released over a period of time ranging from 1 to 12 months. A controlled release formulation of the present invention is capable of effecting a treatment preferably for at least 1 month, preferably for at least 3 months, preferably for at least 6 months, preferably for at least 9 months, and preferably for at least 12 months.

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of treating an animal when administered one or more times over a suitable time period. For example, a preferred single dose of an inhibitor is from 1 microgram (µg) to 10 milligrams (mg) of the therapeutic composition per kilogram body weight of the animal. Booster vaccinations can be administered from 2 weeks to several years after the original administration. Booster administrations preferably are administered when the immune response of the animal becomes insufficient to protect the animal from disease. A preferred administration schedule is one in which from 10 µg to 1 mg of the therapeutic composition per kg body weight of the animal is administered from one to two times over a time period of from 2 weeks to 12 months. Modes of administration can include, but are not limited to, subcutaneous, intradermal, intravenous, intranasal, oral, transdermal, intraocular, intranasal, conjunctival, and intramuscular routes. Methods of administration for other therapeutic compounds can be determined by one skilled in the art, and may include administration of a therapeutic composition one or more times, on a daily, weekly, monthly or yearly regimen; routes of administration can be determined by one skilled in the art, and may include any route. A preferred route of administration of an inhibitory compound when administering to fleas is a topical, or "spot-on" formulation administered to the body surface of the animal, so that a flea would encounter the inhibitory compound when attached to the animal; another preferred route of administration of an inhibitory compound is an oral formulation that, when fed to an animal, would enter the bloodstream of the animal, which would then be transferred to a flea while feeding from the animal.

A recombinant protein vaccine of the present invention comprises a recombinantly-produced flea peritrophin protein of the present invention that is administered to an animal according to a protocol that results in the animal producing a sufficient immune response to protect itself from a flea infestation. Such protocols can be determined by those skilled in the art.

According to one embodiment, a nucleic acid molecule of the present invention can be administered to an animal in a fashion to enable expression of that nucleic acid molecule into a protective protein or protective RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid as a genetic vaccine (e.g., as naked DNA or RNA molecules, such as is taught, for example in Wolff et al., 1990, *Science* 247, 1465–1468) or (b) administering a nucleic acid molecule packaged as a recombinant virus vaccine or as a recombinant cell vaccine (i.e., the nucleic acid molecule is delivered by a viral or cellular vehicle).

A genetic (i.e., naked nucleic acid) vaccine of the present invention includes a nucleic acid molecule of the present invention and preferably includes a recombinant molecule of the present invention that preferably is replication, or otherwise amplification, competent. A genetic vaccine of the present invention can comprise one or more nucleic acid molecules of the present invention in the form of, for example, a dicistronic recombinant molecule. Preferred genetic vaccines include at least a portion of a viral genome, i.e., a viral vector. Preferred viral vectors include those based on alphaviruses, poxviruses, adenoviruses, herpesviruses, picornaviruses, and retroviruses, with those based on alphaviruses, such as sindbis or Semliki forest virus, species-specific herpesviruses and poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic vaccines of the present invention can be administered in a variety of ways, with intramuscular, subcutaneous, intradermal, transdermal, conjunctival, intraocular, intranasal and oral routes of administration being preferred. A preferred single dose of a genetic vaccine ranges from 1 nanogram (ng) to 600 µg, depending on the route of administration and/or method of delivery, as can be determined by those skilled in the art. Suitable delivery methods include, for example, by injection, as drops, aerosolized and/or topically. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picornaviruses, and retroviruses. Preferred recombinant virus vaccines are those based on alphaviruses (such as Sindbis virus), raccoon poxviruses, species-specific herpesviruses and species-specific poxviruses. An example of methods to produce and use alphavirus recombinant virus vaccines are disclosed in U.S. Pat. No. 5,766,602 to Xiong and Grieve, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from flea infestation as disclosed herein. For example, a recombinant virus vaccine comprising a flea peritrophin nucleic acid molecule of the present invention is administered according to a protocol that results in the animal producing a sufficient immune response to protect itself from flea infestation. A preferred single dose of a recombinant virus vaccine of the present invention is from $1 \times 10^4$ to $1 \times 10^8$ virus plaque forming units (pfu) per kilogram body weight of the animal. Administration protocols are similar to those described herein for protein-based vaccines, with subcutaneous, intramuscular, intranasal, intraocular, conjunctival, and oral administration routes being preferred.

A recombinant cell vaccine of the present invention includes recombinant cells of the present invention that express at least one protein of the present invention. Preferred recombinant cells for this embodiment include Salmonella, *E. coli*, Listeria, Mycobacterium, *S. frugiperda*, yeast, (including *Saccharomyces cerevisiae* and *Pichia pastoris*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from $10^8$ to $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to protect an animal from flea infestation can be tested in a variety of ways including, but not limited to, detection of protective antibodies (using, for example, proteins or mimetopes of the present invention), detection of cellular immunity within the treated animal, or challenge of the treated animal with the fleas to determine whether the treated animal is resistant to infestation. Challenge studies can include direct administration of fleas to the treated animal. In one embodiment, therapeutic compositions can be tested in animal models such as mice. Such techniques are known to those skilled in the art.

As discussed herein, one therapeutic composition of the present invention includes an inhibitor of flea peritrophin protein activity, i.e., a compound capable of substantially interfering with the function of a flea peritrophin protein. An inhibitor of flea peritrophin protein activity, or function, can be identified using flea peritrophin proteins of the present invention. A preferred inhibitor of flea peritrophin protein function is a compound capable of substantially interfering with the function of a flea peritrophin protein and which does not substantially interfere with the function of host animal peritrophin proteins. As used herein, a compound that does not substantially inhibit or interfere with host animal peritrophin proteins is one that, when administered to a host animal, the host animal shows no significant adverse effects attributable to the inhibition of peritrophin and which, when administered to an animal in an effective manner, is capable of protecting that animal from flea infestation.

One embodiment of the present invention is a method to identify a compound capable of inhibiting flea peritrophin protein activity. Such a method includes the steps of (a) contacting (e.g., combining, mixing) an isolated flea peritrophin protein of the present invention, with a putative inhibitory compound under conditions in which, in the absence of the compound, the protein has flea peritrophin protein activity, and (b) determining if the putative inhibitory compound inhibits the activity. Such conditions under which a flea peritrophin protein has flea peritrophin protein activity include conditions in which a flea peritrophin protein has a correct three-dimensionally folded structure under physiologic conditions, i.e. physiologic pH, physiologic ionic concentrations, and physiologic temperatures. Putative inhibitory compounds to screen include antibodies (including fragments and mimetopes thereof), putative substrate analogs, and other, preferably small, organic or inorganic molecules.

A preferred method to identify a compound capable of inhibiting flea peritrophin protein activity includes contacting an isolated flea peritrophin protein of the present invention with a putative inhibitory compound under conditions in which, in the absence of the compound, the protein has flea peritrophin protein activity; and determining if the putative inhibitory compound inhibits the activity.

Another embodiment of the present invention is an assay kit to identify an inhibitor of a flea peritrophin protein of the present invention. This kit comprises an isolated flea peritrophin protein of the present invention, and a means for determining inhibition of an activity of flea peritrophin protein, where the means enables detection of inhibition. Detection of inhibition of flea peritrophin protein identifies a putative inhibitor to be an inhibitor of a flea peritrophin protein. Means for determining inhibition of a flea peritrophin protein include, for example, an assay system that detects binding of a putative inhibitor to a flea peritrophin molecule, and an assay system that detects interference by a putative inhibitor of the ability of flea peritrophin protein to hydrolyze a substrate. Means and methods are described herein and are known to those skilled in the art.

The following examples are provided for the purposes of illustration and are not intended to limit the scope of the present invention. The following examples include a number of recombinant DNA and protein chemistry techniques known to those skilled in the art; see, for example, Sambrook et al., ibid.

EXAMPLE 1

This Example describes the isolation of RNA from the hindgut and Malpighian tubules (HMT) of *Ctenocephalides felis* and the use of isolated RNA to construct subtracted and unsubtracted cDNA libraries.

Approximately 10,000 hindguts and Malpighian tubules were dissected from equal numbers of cat blood fed and unfed adult *C. felis* with a male to female ratio of 1 to 4, and total RNA was extracted using a guanidine isothiocyanate lysis buffer and the standard procedure described by Sambrook et al. Poly-A enriched mRNA was purified from total RNA above using a mRNA Purification Kit, available from Pharmacia Biotech, Piscataway, N.J., following the manufacturer's protocol. The same procedures were used to extract total RNA and isolate poly-A enriched mRNA from the dissected *C. felis* bodies following removal of HMT, referred to hereinafter as "non-HMT mRNA".

Poly-A enriched mRNA was used to construct a cDNA library using subtractive hybridization and suppression PCR as follows. Subtractive hybridization and suppression PCR was conducted using a PCR-Select™ cDNA Subtraction Kit, available from Clontech Laboratories, Inc., Palo Alto, Calif. according to the manufacturer's instructions. Briefly, this kit uses subtractive hybridization and suppression PCR to specifically amplify cDNA sequences that are present in the tester cDNA and absent in the driver cDNA, thus enriching for tester-specific sequences. The efficiency of the subtraction process can be assessed by semi-quantitative PCR and by comparing the ethidium bromide staining patterns of the subtracted and unsubtracted samples on agarose gels as described in section V.D. of the manufacturer's protocol. For the semi-quantitative PCR, three genes with mRNAs known to be expressed outside of the HMT tissue were used to test for specific subtraction. These genes encoded putative actin, N-aminopeptidase, and serine protease proteins.

Subtractive hybridization and suppression PCR was conducted under the following conditions. Two micrograms ($\mu$g) of HMT mRNA was used as the template for synthesis of the tester material and 2 $\mu$g of non-HMT mRNA was used as template for synthesis of the driver material in this reaction. The number of cycles used in the selective amplification steps was optimized using the manufacturer's protocols. Optimization resulted in the use of 24 rather than the standard 27 cycles of primary PCR in combination with 15 cycles of secondary PCR rather than the standard 12 cycles.

The products from the suppressive PCR reaction were ligated into the pCR®2.1 vector, available from Invitrogen, Carlsbad, Calif., using an Original TA Cloning® Kit, available from Invitrogen. The ligation reaction was then used to transform INVαF' One Shot™ competent cells, available from Invitrogen, which were plated on Luria broth (LB) agar with 50 micrograms per milliliter (μg/ml) ampicillin, available from Sigma-Aldrich Co., St. Louis, Mo., and 50 μg/ml 5-bromo-4-chloro-3-indoyl β-D-galactopyranoside (X-Gal), available from Fisher Biotech, Fair Lawn, N.J. Transformed colonies were amplified and the DNA isolated using the standard alkaline lysis procedure described by Sambrook et al., ibid.

Automated cycle sequencing of DNA samples was performed using an ABI PRISM™ Model 377, available from Perkins Elmer, with XL upgrade DNA Sequencer, available from PE Applied Biosystems, Foster City, Calif., after reactions were carried out using the PRISM™ Dye Terminator Cycle Sequencing Ready Reaction Kit or the PRISM™ dRhodamine Terminator Cycle Sequencing Ready Reaction Kit or the PRISM™ BigDye™ Terminator Cycle sequencing Ready Reaction Kit, available from PE Applied Biosystems, following the manufacturer's protocol, hereinafter "standard sequencing methods". Sequence analysis was performed using SeqLab, using default parameters. Each sequence read was trimmed of vector sequence at either end and submitted for a search through the National Center for Biotechnology Information (NCBI), National Library of Medicine, National Institute of Health, Baltimore, Md., using the BLAST network. This database includes SwissProt+PIR+SPupdate+GenPept+GPUpdate+PDB databases. The search was conducted using the xBLAST function, which compares the translated sequences in all 6 reading frames to the protein sequences contained in the database.

An unsubtracted HMT cDNA library was constructed as follows. Approximately 10,000 HMT tissues were dissected from equal numbers of unfed and cat blood-fed adult *C. felis* with a male to female ratio of 1:4. Total RNA was extracted using a guanidine isothiocyanate lysis buffer and procedures described in Sambrook et al., followed by isolation using a mRNA purification kit, available from Pharmacia, according to the manufacturer's protocols. The library was constructed with 5 μg of isolated mRNA using a ZAP-cDNA® cDNA synthesis kit, and packaged using a ZAP-cDNA® Gigapack® gold cloning kit, both available from Stratagene, La Jolla, Calif. The resultant HMT library was amplified to a titer of $5\times10^9$ plaque forming units per milliliter (pfu/ml). Single clone excisions were performed using the Ex-Assist™ helper phage, available from Stratagene, and used to create double stranded plasmid template for sequencing using the manufacturer's protocols with the following exceptions. Following incubation of the SOLR cells with the cleared phage lysate, the mixture was used to inoculate LB broth, and the mix was incubated overnight and then subjected to mini-prep plasmid preparation and sequencing as described for the subtracted HMT library above.

EXAMPLE 2

This example describes the production of a *C. felis* cDNA pool by Rapid Amplification of cDNA Ends (RACE cDNA pool).

Total RNA was extracted from adult fed and unfed fleas as follows. Approximately 1000 adult fed fleas and 1000 adult unfed fleas were frozen on dry ice and separately ground into powder using a mortar and pestle and total RNA was extracted from each powder as follows. Ten ml of solution D (4 M guanidine isothiocyanate, 25 mM Sodium Citrate pH 7.0, 1.5% Sarcosyl, 0.5 M 2-mercaptoethanol) were added to the powder and the suspension was mixed by shaking. One ml of 2M sodium acetate, pH 4.0 and 3 ml of pH 4.7 phenol/chloroform/isoamyl alcohol (125:24:1), available from Sigma, were added and the suspension was mixed on a vortex shaker then incubated on ice for 15 minutes. Following incubation, the mixture was centrifuged at 10,000×g for 20 minutes and the supernatant was removed and extracted twice with pH 4.7 phenol/chloroform/isoamyl alcohol. Next, an equal volume of isopropanol was added to the supernatant and incubated at −20° C. for 2 hours followed by centrifugation at 10,000×g for 20 minutes. Following centrifugation, the supernatant was removed and discarded and the pellet was washed in 70% ethanol and allowed to dry at room temperature. The pellet was resuspended in 10 mM Tris 1 mM EDTA pH 8.0. Spectrophotometer analysis indicated that the yield of total RNA from unfed fleas was 1140 μg and the yield from fed fleas was 1500 μg.

Six-hundred pg from each of the fed and unfed adult flea total RNA extractions were combined and mRNA was then extracted using a mRNA Purification Kit, available from Amersham Pharmacia Biotech, Piscataway, N.J., using the manufacture's protocol. Approximately 15–25 μg of mRNA were isolated based on spectrophotometer analysis and ethidium bromide staining. One μg of purified mRNA was used as template to construct a RACE cDNA pool using a SMART™ RACE cDNA Amplification Kit, available from Clontech Laboratories, Inc., Palo Alto, Calif., according to the manufacture's instructions.

EXAMPLE 3

This example describes the cloning, sequencing, recombinant protein expression and purification of a *C. felis* peritrophin-like nucleic acid molecule, referred to herein as PL1. This example also describes the expression of PL1 mRNA in a variety of flea tissues.

A. Isolation of PL1 Nucleic Acid Molecules

A TA clone from the HMT EST library described in Example 1 was sequenced using standard sequencing methods and shown to have homology to a chitinase-like gene from *Bombyx mori* (silkworm). This clone was digested with EcoRI to excise an insert 429 nucleotides in length, referred to as peritrophin-like molecule 1 (PL1) nucleic acid molecule nCfPL1$_{429}$. The insert was isolated by gel purification using a Gel Purification kit, available from Qiagen, Valencia, Calif. Approximately 50 ng of purified nCfPL1$_{429}$ was used to construct a $^{32}$P α-dATP labeled DNA probe using a Megaprime DNA labeling kit, available from Amersham, using the manufacturer's protocols.

The $^{32}$P α-dATP labeled probe was used in a plaque lift hybridization procedure to isolate a clone from the HMT lambda-ZAP unsubtracted cDNA library described in Example 1 as follows. Filters were hybridized with $1\times10^6$ counts per minute (cpm) per ml of the probe in 5×SSPE, (see Sambrook et al., ibid.), 1.2% sodium dodecyl sulfate (SDS), 0.1 mg/ml salmon sperm DNA and 5×Denhardt's reagent, (see Sambrook et al., ibid.), at 55° C. for 14 hours. The filters were washed as follows: (a) 10 minutes with 5×SSPE and 1% SDS, (b) 10 minutes with 2×SSPE and 1% SDS, (c) 10 minutes with 1×SSPE and 0.5% SDS, and (d) 10 minutes with 0.5×SSPE and 1% SDS. All washes were conducted at 55° C. Plaques that hybridized strongly to the probe were isolated and subjected to in vivo excision. In vivo excision was performed using the Stratagene Ex-Assist™ helper phage system and protocols, to convert a positive plaque to pBluescript™ plasmid DNA. Sequencing was conducted using standard sequencing methods following preparation of DNA with a Qiagen Qiaprep™ spin mini prep kit using the manufacturer's instructions and restriction enzyme digestion with 1 µl of 20 U/µl each of EcoRI and XhoI, available from New England Biolabs, Beverly, Mass. Plaques that hybridized strongly to the probe were isolated and subjected to in vivo excision. In vivo excision was performed using the Stratagene Ex-Assist™ helper phage system and protocols, to convert a positive plaque to pBluescript™ plasmid DNA, and sequencing was conducted following preparation of DNA with a Qiagen Qiaprep™ spin mini prep kit using the manufacturer's instructions and restriction enzyme digestion with 1 µl of 20 U/µl each of EcoRI and XhoI, available from New England Biolabs. A clone was isolated from a primary plaque, containing a nucleic acid molecule of 1096 base pairs, referred to herein as $nCfPL1_{1096}$, the coding strand of which has a nucleotide sequence denoted herein as SEQ ID NO:1. The complement of SEQ ID NO:1 is represented herein as SEQ ID NO:3. Sequencing of $nCfPL1_{429}$ indicated that $nCfPL1_{429}$ shares 100% identity with nucleotides 148 through 576 of SEQ ID NO:1.

Translation of SEQ ID NO:1 suggests that nucleic acid molecule $nCfPL1_{1096}$ encodes a full-length chitin-binding protein of 272 amino acids, referred to herein as $PCfCfPL1_{272}$, having an amino acid sequence represented by SEQ ID NO:2, assuming the initiation codon spans from nucleotide 6 through nucleotide 8 of SEQ ID NO:1 and the termination codon spans from nucleotide 822 through nucleotide 824 of SEQ ID NO:1. The coding region encoding $PCfPL1_{272}$, is represented by nucleic acid molecule $nCfPL1_{816}$, having a coding strand with the nucleic acid sequence represented by SEQ ID NO:4 and a complementary strand with nucleic acid sequence represented by SEQ ID NO:5. The amino acid sequence of $PCfPL1_{272}$ predicts that $PCfPL1_{272}$ has an estimated molecular weight of 30.6 kDa and an estimated pI of 7.3.

Comparison of amino acid sequence SEQ ID NO:2 with amino acid sequences reported in GenBank indicates that SEQ ID NO:2 showed the most homology, i.e., 26% identity, with a *Lucilia cuprina* peritrophin-44 protein, GenBank Accession No. 407976. Comparison of SEQ ID NO:4 with nucleic acid sequences reported in GenBank indicates that SEQ ID NO:4 showed the most homology, i.e., 40%, with a *Lucilia cuprina* peritrophin-44 nucleic acid molecule, GenBank Accession number L25106. Percent identity calculations were performed using the SeqLab software with default parameters.

B. Expression of a PL1 Nucleic Acid Molecule

A nucleic acid molecule comprising nucleotides 59 through 827 of SEQ ID NO:1, encoding a predicted mature flea PL1, was PCR amplified from the pBluescript™ clone described above as the template, using sense primer PL1-FE, having nucleotide sequence 5' CGG GAT CCT GCT GAC AGG AAT TCG CCC AC 3', having a BamHI site indicated in bold, designated herein as SEQ ID NO:50, and anti-sense primer PL1-RE, having nucleotide sequence 5' CAT GGT ACC CCT GGT TTA AGC CTT ACT TAG C 3', having a KpnI site indicated in bold, designated herein as SEQ ID NO:51. PCR reactions were performed using standard PCR reaction and thermocycling conditions described herein. The PCR product was digested with BamHI and KpnI and ligated into the vector pTrcHisB, available from Invitrogen, that had been digested with BamHI and KpnI and treated with alkaline phosphatase. The resulting recombinant molecule, referred to herein as $pTrc-nCfPL1_{769}$, was transformed into *E. coli* strain BL21, available from Novagen, to form recombinant cell *E. coli*:$pTrc-nCfPL1_{769}$. The recombinant cell was grown under standard conditions and then incubated in the presence of 0.5 µM IPTG to induce expression of recombinant protein, predicted to be a protein of approximately 32 kDa. Expression of protein was confirmed using Coomassie-blue-stained Tris-glycine gel and by Western blot using a T7 tag antibody which showed expression of an 32-kDa protein. The protein product was purified by liquid chromatography using a HiTrap™ chelating column charged with $NiCl_2$, available from Pharmacia, and was shown to contain the His tag of the vector when subjected to automated protein sequencing by Edman degradation.

C. Northern Blot Analysis

A Northern Blot analysis was conducted as follows to determine whether PL1 is expressed exclusively in HMT tissues. HMT tissues were dissected from 1000 adult cat blood-fed *C. felis* having a male to female ratio of 1:4. Total RNA was separately extracted from HMT tissues and the HMT-less carcasses that resulted from these dissections as follows. The tissues were frozen at −80° C., ground into a powder with a mortar and pestle, and the powders were equally divided into four 2-ml eppendorf tubes each containing 1 ml of lysis buffer. The lysis buffer contained 4 M guanidinium thiocyanate, 25 mM sodium citrate, pH 7.0, 3% sarcosyl, 0.5M 2-mercaptoethanol, 0.1% antifoam, and 1 mM aurintricarboxylic acid, all available from Sigma Chemical Corporation, St. Louis, Mo. After mixing, the tubes were spun at 14,000 rpm for 2 minutes and the supernatants were transferred to separate 2 ml eppendorf tubes containing 250 µl of phenol, available from Aldrich, Milwaukee, Wis. After mixing, the tubes were spun at 14,000 rpm for 5 minutes and the supernatants were transferred to new 2-ml tubes. This process was repeated 3 times until no proteinaceous matter was visible at the phenol/lysis buffer interface, then 250 µl of chloroform was added to each tube and the contents mixed and spun at 14,000 rpm for 5 minutes followed by transferring the supernatant to a new tube. A volume of isopropanol equal to the volume of the supernatant was added to each tube and the tubes placed on ice for 5 minutes. The tubes were then spun at 14,000 rpm at room temperature for 15 minutes, the supernatants were removed and discarded and the remaining RNA pellets were washed with 70% ethanol and dried. The RNA pellets were resuspended in 100 µl of TE (10 mM Tris, 1 mM ethylenediaminetetraacetic acid (EDTA)). The quantity of RNA in each tube was then determined using a spectrophotometer.

Approximately 10 µg of each RNA was added to separate tubes containing 18.75 µl of loading buffer, which consists of 50% formamide, 16% formaldehyde, 17% water, 7% glycerol, 1×MOPS buffer (a 1:20 dilution of 0.4 M 93-[N-morpholino]propanesulfonic acid (MOPS), 0.1 M sodium acetate, and 20 mM EDTA), 10 µl ethidium bromide, and 10 µl bromophenol blue dye, all available from Sigma. The tubes were heated to 95° C. for 2 minutes then placed on ice. The RNA samples were separated by gel electrophoresis on a 1.5% agarose gel with 3.2% formaldehyde and 1×MOPS buffer; the gel was then soaked in water for 30 minutes prior to transfer to remove excess formaldehyde. The gel was then transferred using standard techniques, described by Sambrook et al., ibid, with 10×SSPE as the transfer buffer onto Nytran® nylon membrane, available from Schleicher and Schuell Inc., Keene, N.H. The membrane was UV cross-linked using the Stratalinker®, available from Stratagene, then prehybridized at 42° C. in 50% formamide, 5×SSPE, 1.2% SDS, 5×Denhardt's reagent, 2.5 mM EDTA, and 100 µg/ml salmon sperm DNA. A probe comprising the PL1 nucleic acid molecule, $nCfPL1_{1096}$ was labeled with $\alpha$-$^{32}$P-ATP using a DNA labeling kit, available from Amersham and added to the buffer at a concentration of approximately 1×10$^6$ cpm/ml, and allowed to hybridize for 18 hours at 42°

C. The blot was then washed as follows: 10 minutes at 42° C. in 4×SSPE and 1% SDS; 10 minutes at 42° C. in 2×SSPE and 1% SDS; 10 minutes 42° C. with 0.5×SSPE and 0.5×SDS; and 10 minutes at 42° C. with 0.25×SSPE and 0.25% SDS. The blot was then exposed to film for 1 hour, and the film was developed using standard procedures. Analysis of the developed film revealed that PL1 mRNA was present in HMT tissues but was not present in non-HMT tissues.

Northern Blot analysis was also conducted to determine whether PL1 mRNA is expressed only in certain stages of the flea life cycle and whether PL1 mRNA expression is influenced by feeding. Total RNA was extracted as described above from 1000 fleas at each of the following flea life stages; eggs; first instar larvae; third instar larvae; wandering larvae and pupae as well as from 1000 adult fleas under the following feeding conditions: unfed; fed on cat blood for 15 minutes; fed on cat blood for 2 hours; fed on cat blood for 8 hours; and fed on cat blood for 24 hours. Each RNA sample was separated by gel electrophoresis, transferred to nylon membrane and hybridized with α-$^{32}$P-ATP labeled nCfPL1$_{429}$ probe as described above. Analysis of the developed film revealed that PL1 mRNA was detected in all adult fleas tested regardless of feeding conditions but was not detected in any of the non-adult life stages.

EXAMPLE 4

This Example describes the further isolation and characterization of a Peritrophin-like cDNA nucleic acid molecules, referred to herein as PL2.

A cDNA designated clone 2232–23 was isolated from the unsubtracted HMT library as described in Example 1, denoted herein as SEQ ID NO:6. Analysis of clone 2232–23 indicated that the cDNA, denoted nCfPL2$_{445}$ is 445 nucleotides in length. Translation of the coding strand of nCfPL2$_{445}$ suggests that nucleic acid molecule nCfPL2$_{445}$ encodes a partial-length Peritrophin-like protein of 113 amino acids, referred to herein as PCfPL2$_{113}$, assuming a stop coding spanning nucleotides 342 through 344 of nCfPL2$_{445}$.

Additional coding sequence corresponding to the 5' end of nCfPL2$_{445}$ was isolated by PCR performed using a RACE cDNA pool prepared as described in Example 2 as template. A first PCR reaction was performed using reverse primer PL2-R1, which is complementary to nucleotides 167 through 187 of the nCfPL2$_{445}$ cDNA, having a nucleic acid sequence 5' GTC TGG AAG CTC AGG AAG AGG 3', denoted herein as SEQ ID NO:52, in conjunction with forward Adapter Primer 1, having a nucleic acid sequence 5' CCA TCC TAA TAC GAC TCA CTA TAG GGC 3', denoted herein as SEQ ID NO:53, under the following thermocycling conditions: (1) 94° C. for 30 seconds, (2) 5 cycles of 94° C. for 10 seconds and 72° C. for 4 minutes, (3) 5 cycles of 94° C. for 10 seconds and 70° C. for 4 minutes, and (4) 25 cycles of 94° C. for 10 seconds then 68° C. for 4 minutes. The product of this reaction was diluted 1:50 and used as template for a second PCR reaction as follows. Forward adapter primer 2, having nucleic acid sequence 5' ACT CAC TAT AGG GCT CGA GCG GC 3', denoted herein as SEQ ID NO:54, was used with reverse primer PL2-R2, which is complementary to nucleotides 29–52 of the nCfPL2$_{445}$ cDNA, having a nucleic acid sequence 5' GTA ATA TGC GTG ACA ATC GTG TGG 3', denoted herein as SEQ ID NO:55, using the thermocycling conditions described for the first PCR reaction. The resulting product was gel purified to reveal a distinct band corresponding to a nucleic acid molecule of approximately 900 bp in length. The fragment was then ligated into the pCR II TA Cloning vector, available from Qiagen, and sequenced using an ABI PRISM 377 automatic DNA Sequencer. Sequencing revealed that nucleotides 791–835 of the fragment had 100% identity with nucleotides 1–45 of the nCfPL2$_{445}$ cDNA. The 900 nucleotide and 445 nucleotide sequences were aligned to form a contiguous sequence, denoted nCfPL2$_{1279}$, which is 1279 nucleotides in length, having a coding strand with nucleic acid sequence SEQ ID NO:7 and a complementary sequence having SEQ ID NO:8. Translation of SEQ ID NO:7 suggests that nucleic acid molecule nCfPL2$_{1279}$ encodes a non full-length Peritrophin-like protein of 391 amino acids.

In order to isolate additional sequence 5' to SEQ ID NO:7, nested PCR reactions were performed using the RACE cDNA pool as template. For the first PCR, forward adapter primer AP1 (SEQ ID NO:53) was used with reverse primer PL2-R1 (SEQ ID NO:52) under standard PCR reaction conditions and the following thermocycling conditions: (1) 94° C. for 1 minute, (2) 5 cycles of 94° C. for 20 seconds and 70° C. for 1 minute, (3) 5 cycles of 94° C. for 20 seconds and 68° C. for 1 minute, (4) 10 cycles of 94° C. for 20 seconds and 66° C. for 1 minute. The products of this reaction were diluted 1:50 in water and used as template for the second, nested PCR. The second PCR reaction used forward adapter primer AP2 in conjunction with reverse primer PL2-R5, which is complementary to nucleotides 70–93 of SEQ ID NO:7, having a nucleotide sequence 5' CGG TGC AAG TTA TAG AAC CTT CCG 3', denoted herein as SEQ ID NO:56 under standard PCR reaction conditions using the following thermocycling conditions: (1) 94° C. for 1 minute, (2) 5 cycles of 94° C. for 20 seconds and 70° C. for 1 minute, (3) 5 cycles of 94° C. for 20 seconds and 68° C. for 1 minute, (4) 40 cycles of 94° C. for 20 seconds and 66° C. for 1 minute. The products of this reaction were separated by agarose gel electrophoresis and a band approximately 279 nucleotides in length was excised from the gel and purified. The fragment, referred to as nCfPL2$_{279}$, having a coding nucleic acid sequence designated SEQ ID NO:9 and a complementary sequence designated SEQ ID NO:10, was then ligated into the pCROII TA Cloning vector, available from Qiagen, and sequenced as described above. Sequencing revealed that nucleotides 228–279 of nCfPL2$_{279}$ were identical to nucleotides 42–93 of SEQ ID NO:7, however, nucleotides 186–228 of nCfPL2$_{279}$ had no significant similarity to SEQ ID NO:7. This discrepancy may be the result of alternative RNA splicing or may be an artifact of the cDNA pool. To determine the reason for this discrepancy, additional fragments corresponding to this region were isolated by PCR from flea cDNA libraries from adult midguts, hindgut and Malpighian tubules and mixed instar larvae using techniques described herein. Sequence analysis of fragments obtained from these libraries revealed that these fragments were identical in sequence to the sequence of nCfPL2$_{279}$, therefore, the region of SEQ ID NO:7 which did not align to nCfPL2$_{279}$ was deemed to be an artifact and was not used in subsequent alignments.

The PL2 sequences described above were aligned to form a contiguous sequence, denoted nCfPL2$_{1465}$, which is 1465 nucleotides in length, having a coding strand with nucleic acid sequence SEQ ID NO:11 and a complementary sequence having SEQ ID NO:13. Translation of SEQ ID NO:11 suggests that nucleic acid molecule nCfPL2$_{1465}$ encodes a full-length Peritrophin-like protein of 453 amino acids, referred to herein as PCfPL2$_{453}$, having an amino acid sequence represented by SEQ ID NO:12, assuming an initiation codon spanning from nucleotide 3 through nucleotide 5 of SEQ ID NO:11 and a termination codon spanning from nucleotide 1362 through nucleotide 1364 of SEQ ID NO:11. The coding region encoding PCfPL2$_{453}$, is represented by nucleic acid molecule nCfPL2$_{1359}$, having a coding strand with the nucleic acid sequence represented by SEQ ID NO:14 and a complementary strand with nucleic acid sequence represented by SEQ ID NO:15. The amino acid sequence of SEQ ID NO:12, predicts that PCfPL2$_{453}$ has an estimated molecular weight of 49 kDa and an estimated isoelectric point (pI) of 4.7.

Comparison of amino acid sequence SEQ ID NO:12 with amino acid sequences reported in GenBank indicates that SEQ ID NO:12 showed the most homology, i.e., 28% identity, with a Drosophila melanogaster locus AE003474 protein (Accession # AAF47629). Comparison of SEQ ID NO:14 with nucleic acid sequences reported in GenBank indicates that SEQ ID NO:14 showed the most homology, i.e., 50% identity, with a Penaeus semisulcatus (a crustacean) peritrophin-like protein 1 cDNA (Accession # AF095580). Percent identity calculations were performed using the SeqLab software with default parameters.

EXAMPLE 5

This Example describes the further characterization and expression of a flea Peritrophin-like sequence cDNA, referred to herein as PL3.

A. Isolation of PL3 Nucleic Acid Molecules

A cDNA designated clone 2240-17 was isolated from the unsubtracted HMT library as described in Example 1. Analysis of clone 2240-17 indicated that the cDNA, denoted nCfPL3$_{387}$, is 387 nucleotides in length, having a coding strand with nucleic acid sequence SEQ ID NO:16 and a complementary sequence having SEQ ID NO:18. Translation of SEQ ID NO:16 suggests that nucleic acid molecule nCfPL3$_{387}$ encodes a full-length Peritrophin-like protein of 81 amino acids, referred to herein as PCfPL3$_{81}$, having an amino acid sequence represented by SEQ ID NO:17, assuming the initiation codon spans from nucleotide 20 through nucleotide 22 of SEQ ID NO:16 and the termination codon spans from nucleotide 263 through nucleotide 265 of SEQ ID NO:16. The coding region encoding PCfPL3$_{81}$, is represented by nucleic acid molecule nCfPL3$_{243}$, having a coding strand with the nucleic acid sequence represented by SEQ ID NO:19 and a complementary strand with nucleic acid sequence represented by SEQ ID NO:20. The amino acid sequence of SEQ ID NO:17, predicts that PCfPL3$_{81}$ has an estimated molecular weight of 9.1 kDa and an estimated isoelectric point (pI) of 3.64.

Comparison of amino acid sequence SEQ ID NO:17 with amino acid sequences reported in GenBank indicates that SEQ ID NO:17 showed the most homology, i.e., 34.2% identity, with a Anopheles gambiae peritrophin 1 protein (Accession # AAC39127). Comparison of SEQ ID NO:19 with nucleic acid sequences reported in GenBank indicates that SEQ ID NO:19 showed the most homology, i.e., 37% identity, with a Anopheles gambiae chloride intracellular channel 2 (Accession # AF030431). Percent identity calculations were performed using the SeqLab software with default parameters.

B. Expression of a PL3 Protein

In order to express a PL3 protein, the entire coding region was amplified by PCR and then ligated into the E. coli expression vector pTrcHisB, available from Invitrogen, as follows. Forward primer PL3FE, which corresponds to nucleotides 70–93 of SEQ ID NO:16, having the sequence 5' CGG GAT CCC GAA TAT GCT GAC GTA GAT GTG TG 3', denoted SEQ ID NO:57, and having a BamHI restriction endonuclease site indicated in bold, was used in conjunction with reverse primer PL3RE, which is complementary to nucleotides 245–269 of SEQ ID NO:16, having the sequence 5' GGA ATT CTG TTT TAT TCT GGT TGG TAA CAT TC 3', denoted herein as SEQ ID NO:58 and having an EcoRI restriction endonuclease site indicated in bold, in a PCR reaction using SEQ ID NO:16 as the template under standard PCR reaction conditions and the following thermocycling conditions: (1) 94° C. for 30 seconds, (2) 25 cycles of 94° C. for 10 seconds, 55° C. for 10 seconds and 72° C. for 3 minutes. The reaction product was separated on a 1.5% agarose gel, and a band corresponding to an approximately 200 nucleotide molecule, as visualized by agarose gel electrophoresis and ethidium bromide staining, was cut from the gel and purified using a QIAquick Gel Extraction Kit, available from Qiagen.

The product of the PCR reaction was the digested with BamHI and EcoRI restriction endonucleases, available from New England BioLabs, Inc. for 18 hours at 37° C., purified using the QIAquick Nucleotide Removal Kit, available from Qiagen, and ligated into the vector pTrcHisB which had been similarly digested, treated with shrimp alkaline phosphatase, available from New England BioLabs, Inc., for 30 minutes at 37° C., and purified. Following standard transformation procedures into E. coli BL-21 competent cells, a bacterial clone containing the plasmid pTrcPL3$_{200}$ was isolated. DNA sequence analysis of the clone confirmed that nucleotides 70 through 269 of SEQ ID NO:16 had been successfully ligated into the pTrcHisB expression vector in frame with the N-terminal T7 Tag epitope encoded by the vector. The recombinant protein encoded thereby is predicted to be 97 amino acids in length (including the T7 Tag) and have a molecular mass of 10.9 kDa, including the T7 Tag, and have a pI of 4.08.

The 97 amino acid recombinant PL3 protein described above was expressed as follows. Five mls of Luria broth were inoculated with a glycerol stock of E. coli BL-21 competent cells, available from Novagen, Madison, Wis., that had been transformed with the pTrcPL3$_{200}$ plasmid prepared as described above and allowed to grow overnight at 37° C. under selection with 100 μg/ml ampicillin. A 1-ml aliquot of this culture was then used to inoculate 10 mls of fresh Luria broth containing 100 μg/ml ampicillin and the culture was allowed to grow to an approximate OD reading of 0.5. A 1 ml aliquot of the culture was removed, the cells were pelleted by centrifugation and the supernatant discarded. The cells were resuspended in a solution of 100 μl PBS and 100 μl of 2×SDS-PAGE loading buffer (100 mM Tris pH 6.8, 4% SDS, 20% glycerol, 0.02% bromophenol blue, and 10% 2-mercaptoethanol). Following removal of the 1 ml aliquot described above, IPTG was added to the remaining 9 ml culture to a final concentration of 5 mM of IPTG, the culture was incubated at 37° C. for an additional 60 minutes, 1 ml was removed and the OD measured at approximately 0.6. The cells in this 1 ml sample were then pelleted by centrifugation and resuspended in a solution of 120 μl of PBS and 120 μl of SDS-PAGE loading buffer. Equal volumes of the IPTG-induced and uninduced lysates were loaded onto a 14% Tris-Glycine SDS-PAGE gel, available from Novex, San Diego, Calif. Following electrophoresis, the proteins were transferred from the SDS-PAGE gel to a nitrocellulose membrane and a Western blot analysis was performed using the T7 tag antibody, available from Novagen, which revealed an approximately 18 kDa protein was induced by IPTG. The fact that the recombinant nCfPL3$_{200}$ protein ran at a higher molecular weight than predicted is consistent with previous published results for other peritrophin proteins, and is thought to be due in part to the characteristically low pI of these proteins; See Tellam et al., 1999, Insect Biochemistry and Molecular Biology, 29:87–101. Sequence analysis of this protein indicates that it contained the N-terminal T7 Tag encoded by the vector.

Four flasks, each containing 1 liter of Luria broth with 100 µg/ml ampicillin were inoculated with a starter culture of 5 ml of *E. coli* BL-21 cells transformed with the pTrc-nCfPL3$_{200}$ plasmid as described above. The cultures were allowed to grow at 37° C. until the optical density reached approximately 0.500, at which time a 1 ml aliquot was removed from each flask as the pre-induction sample. IPTG was added to each 1 liter flask to a final concentration of 0.5 mM and the cultures allowed to grow at 37° C. for 135 additional minutes, at which time a 1 ml aliquot was removed from each flask as the post-induction sample. The 1 ml aliquots were centrifuged, the supernatants were discarded and the pellets were resuspended in 100 µl 2×SDS-PAGE loading buffer per each 0.5 optical density units measured. The pre-induction and post induction samples were then tested for recombinant PL3 protein expression using standard Western blot techniques and the T7 Tag antibody. A protein running at approximately 18 kDa was detected in the post-induced but not in the pre-induced samples.

The cells from the remaining 4 liters of culture were centrifuged, the supernatants were discarded and the cell pellets were combined and resuspended in 120 mls of buffer A (50 mM Tris, PH 8.0, 20 mM NaCl, 1 mM phenylmethylsulfonyl fluoride (PMSF)). The sample was then passed through a microfluidizer five times then rocked at 4° C. for 20 minutes. The sample was then centrifuged for 30 minutes and the supernatant collected. Western blot analysis of the supernatant showed that the recombinant nCfPL3$_{200}$ protein was soluble in the first buffer A extraction. The buffer A supernatant containing the recombinant nCfPL3$_{200}$ protein was then further purified by a nickel column, a Q2 anion exchange chromatography column, and cation exchange chromatography, using techniques well known to those of skill in the art.

EXAMPLE 6

This Example describes the characterization, expression, and Northern Blot analysis of a Peritrophin-like sequence cDNA, referred to herein as PL4.

A. Isolation of PL4 Nucleic Acid Molecules

A cDNA designated clone 2244-71 was isolated from the unsubtracted HMT library as described in Example 1. Analysis of clone 2244-71 indicated that the cDNA, denoted nCfPL4$_{960}$, is 960 nucleotides in length, having a coding strand with nucleic acid sequence SEQ ID NO:21 and a complementary sequence having SEQ ID NO:22. Translation of SEQ ID NO:21 suggests that nucleic acid molecule nCfPL4$_{960}$ encodes a partial-length Peritrophin-like protein of 285 amino acids. Additional sequence 5' to nCfPL4$_{960}$ was isolated by PCR using the RACE cDNA pool described in Example 2 as the template, as follows. Adapter Primer 1, i.e. SEQ ID NO:53, was used as the forward primer in conjunction with reverse primer PL4-R1, which is complementary to nucleotides 229–251 of SEQ ID NO:21, having a nucleic acid sequence 5' GAT ATC CAC TTT GAT CAG CGC AC 3', denoted herein as SEQ ID NO:59 in a PCR reaction under standard PCR reaction conditions and the following thermocycling conditions: (1) 94° C. for 30 seconds, (2) 5 cycles of 94° C. for 10 seconds and 72° C. for 4 minutes, (3) 5 cycles of 94° C. for 10 seconds and 70° C. for 4 minutes, (4) 25 cycles of 94° C. for 10 seconds then 68° C. for 4 minutes. The products of this reaction were diluted 1:50 and used as template in a second PCR reaction using Adapter Primer 2, i.e. SEQ ID NO:54, as the forward primer and reverse primer PL4-R2, which is complementary to nucleotides 58–78 of SEQ ID NO:21, having a nucleic acid sequence 5' GGT ACT ACT CCT GGT GCG GGC 3', denoted herein as SEQ ID NO:60, using the thermocycling conditions described for the first PCR reaction. The products of this reaction were gel purified as previously described and the fragment was ligated into the pCR II TA Cloning vector, available from Qiagen, and sequenced to reveal a fragment of approximately 150 nucleotides in length. Sequence analysis revealed that nucleotides 68–146 of the fragment had 100% identity with nucleotides 1–79 of nCfPL4$_{960}$. The two sequences were aligned to form a contiguous sequence of 1029 nucleotides in length, referred to as nCfPL4$_{1029}$, having a coding strand with SEQ ID NO:23 and a complementary strand having SEQ ID NO:24. However, the contiguous sequence did not appear to encode a starting methionine in the predicted protein sequence; thus, a second attempt to isolate the remaining coding sequences at the 5' end was performed as follows. A first PCR reaction was performed with Adapter Primer 1 (SEQ ID NO:53) as the forward primer and PL4-R2 (SEQ ID NO:60) as the reverse primer using the RACE cDNA pool as the template under the thermocycling conditions described above. The products of this reaction were diluted 1:50 and used as the template in a second PCR reaction which used Adapter Primer 2 (SEQ ID NO:54) as the forward primer and reverse primer PL4-R4, which is complementary to nucleotides 58–80 of SEQ ID NO:23, having the nucleic acid sequence 5' CCG TCG ACA TTA AAC TCA CCA TC 3', denoted SEQ ID NO:61, under the thermocycling conditions described for the first PCR reaction. The products of this reaction were gel purified as previously described and the fragment was ligated into the pCR II TA Cloning vector, available from Qiagen, and sequenced to reveal a fragment of approximately 100 nucleotides in length. Sequence analysis revealed that nucleotides 21–101 of the fragment had 100% identity with nucleotides 1–81 of SEQ ID NO:21. The two sequences were aligned to form a contiguous sequence that is 1048 nucleotides in length, referred to herein as nCfPL4$_{1048}$, having a coding strand with SEQ ID NO:25 and a complementary strand with SEQ ID NO:27. Translation of SEQ ID NO:25 suggests that nucleic acid molecule nCfPL4$_{1048}$ encodes a full-length Peritrophin-like protein of 285 amino acids, referred to herein as PCfPL4$_{285}$, having an amino acid sequence represented by SEQ ID NO:26, assuming the initiation codon spans from nucleotide 19 through nucleotide 21 of SEQ ID NO:25 and the termination codon spans from nucleotide 874 through nucleotide 876 of SEQ ID NO:25. The coding region encoding PCfPL4$_{285}$ is represented by nucleic acid molecule nCfPL4$_{855}$, having a coding strand with the nucleic acid sequence represented by SEQ ID NO:28 and a complementary strand with nucleic acid sequence represented by SEQ ID NO:29. The amino acid sequence of SEQ ID NO:26 predicts that PCfPL4$_{285}$ has an estimated molecular weight of 31.4 kDa and an estimated isoelectric point (pI) of 6.99.

Comparison of amino acid sequence SEQ ID NO:26 with amino acid sequences reported in GenBank indicates that SEQ ID NO:26 showed the most homology, i.e., 31.5% identity, with a *Drosophila melanogaster* Gasp precourser (Accession # AAD09748). Comparison of SEQ ID NO:28 with nucleic acid sequences reported in GenBank indicates that SEQ ID NO:28 showed the most homology, i.e., 39.4% identity, with a *Drosophila melanogaster* Gasp precourser (Accession #AF070734). Percent identity calculations were performed using the SeqLab software with default parameters.

B. Northern Blot Analysis

A Northern Blot analysis was conducted as described in Example 3 to determine whether PL4 mRNA is expressed only in certain life stages of the flea life cycle and whether PL4 mRNA is expressed only in HMT tissue. Total RNA was extracted from eggs, first instar larvae, third instar larvae, and wandering larvae, pupae, unfed adults, and adults fed on cat blood for 0.25, 2, 8, or 24 hours, respectively. In addition, total RNA was extracted from hindguts and Malpighian tubules extracted from 24-hour cat blood-fed adult fleas, and from the remaining body parts following the removal of hindguts and Malpighian tubules. Each RNA sample was separated by gel electrophoresis, transferred to nylon membranes and hybridized with $\alpha$-$^{32}$P-ATP labeled nCfPL4$_{960}$ using the conditions described in Example 3.

The results of the Northern blot assay were complex. Although stringent conditions were used, several bands with distinct expression patterns were seen. An approximately 1600 nucleotide message was detected in the egg, first instar, third instar and wandering larval stages only. An approximately 1500 nucleotide message was detected in all life-stages and adult fed timepoints, but with the strongest signals in the egg, first instar larval, and unfed adult stages. A third message, of approximately 1200 nucleotides, was detected in the egg, first instar larval, pupal, and adult lifestages, including all unfed and fed adult timepoints. All three of the messages detected were seen only in the HMT tissues, and were not detected in the carcass tissues.

The detection of three mRNAs instead of one may be the result of the expression of three highly homologous transcripts. It has been reported in the literature that peritrophin gene families have been found that consist of a number of highly related genes, See Schorderet et al., 1998, *Insect Biochemistry and Molecular Biology* 28, 99–111. It is possible that these transcripts represent the products of such a family or that the messages are the RNA products of alternative splicing from a single gene locus.

The coding region of SEQ ID NO:25, was PCR amplified from the RACE cDNA pool described above as the template, using sense primer PL4FE, having nucleotide sequence 5' CGG GAT CCT TAT GAT GGT GAG TTT AAT GTC G 3', which corresponds to nucleotides 75–96 of SEQ ID NO:25, having a BamHI site indicated in bold, designated herein as SEQ ID NO:62, and anti-sense primer PL4RE, having nucleotide sequence 5' GGG GTA CCT TAA TAT AAT TTA GGT TTC CTC TCG C 3', which is complementary to nucleotides 851–876 of SEQ ID NO:25, having a KpnI site indicated in bold, designated herein as SEQ ID NO:63. PCR reactions were performed using the following amplification cycles: (a) one cycle at 94° C. for thirty seconds; (b) thirty cycles at 94° C. for twenty seconds, 68° C. for thirty seconds, and 72° C. for three minutes; and (c) one cycle at 72° C. for five minutes, in reactions containing 2.5 mM MgCl$_2$, 0.2 mM dNTPs, 1 $\mu$M of each primer, 0.5 $\mu$l of 5 U/$\mu$l Taq polymerase, 1 $\mu$l of 1 $\mu$g/$\mu$l template, and 3 $\mu$l of 10×Taq buffer. The products of this reaction were separated on a 1.5% agarose gel, and the appropriate band cut from the gel and purified using the QIAquick Gel Extraction Kit, available from Qiagen, Valencia, Calif. The resulting nucleic acid molecule, referred to herein as nCfPL4$_{802}$, is approximately 802 nucleotides in length, having a coding strand designated SEQ ID NO:30 and a complementary strand designated SEQ ID NO:32. Translation of SEQ ID NO:30 indicates that SEQ ID NO:30 encodes an approximately 266 amino acid protein, designated SEQ ID NO:31, assuming a first codon at nucleotides 2 through 4 and a stop codon at nucleotides 800 through 802 of SEQ ID NO:30.

The purified PCR product was digested with BamHI and KpnI, purified using a QIAquick Nucleotide Removal Kit, available from Qiagen, and ligated into the vector pTrcHisB, available from Invitrogen, that had been similarly purified, digested with BamHI and KpnI and treated with alkaline phosphatase. DNA sequence analysis of the clone confirmed that nucleotides 75 through 876 of SEQ ID NO:25 had been successfully ligated into the pTrcHisB expression vector in frame with the N-terminal T7 Tag epitope encoded by the vector. The resulting recombinant molecule, referred to herein as pTrc-nCfPL4$_{894}$ (which includes the T7 tag), was transformed into *E. coli* strain BL21, available from Novagen Inc., Madison, Wis., to form recombinant cell *E. coli*:pTrc-nCfPL4$_{894}$. Recombinant molecule pTrc-nCfPL4$_{894}$ is predicted to encode a protein including the T7 Tag of 298 amino acids in length, having a molecular mass of 32.8 kDa, and a pI of 5.97.

Recombinant cell *E. coli*:pTrc-nCfPL4$_{894}$ was grown as described in Example 5 and then incubated in the presence of 0.5 mM isopropylthio-$\beta$-galactoside (IPTG) to induce expression of recombinant protein PCfPL4$_{298}$. Expression was confirmed by Western blot using a T7 tag antibody, available from Novagen, which showed expression of an 48-kDa protein. Sequence analysis of PCfPL4$_{298}$ indicates that it contained the N-terminal T7 Tag encoded by the vector. The fact that PCfPL4$_{298}$ ran at a higher molecular weight than predicted is consistent with previous published results for other peritrophin proteins, and is thought to be due in part to the characteristically low pI of these proteins, See Tellam et al. ibid.

Recombinant protein PCfPL4$_{298}$ was produced and purified as follows. Four flasks containing 1 liter each of Luria broth with 100 ug/ml ampicillin were innoculated with *E. coli* BL21 cells transformed with the pTrc PCfPL4$_{298}$ plasmid as described above. The cultures were allowed to grow at 37° until the optical density (OD$_{600}$) reached approximately 0.500 then a one ml aliquot was removed as the pre-induction sample. Next, IPTG was added to a final concentration of 0.5 mM and the cultures allowed to grow at 37° C. for 135 minutes. A one-ml aliquot was then removed as the post-induction sample. Both one-ml aliquots were centrifuged to pellet the cells. The cells were resuspended in 100 $\mu$l 2×SDS-PAGE loading buffer for each 0.5 optical density unit measured. The pre-induction and post induction samples were then tested for expression of PCfPL4$_{298}$ using by Western blot with the T7 Tag antibody described previously. A protein running at approximately 48 kDa was detected in the post-induced but not in the pre-induced samples.

The cells from the remaining 4 liters of culture were pelleted by centrifugation and resuspended in 120 ml of Buffer A. The sample was passed through a microfluidizer five times, rocked at 4° for 20 minutes, then centrifuged for 30 minutes and the supernatant collected. Western blot analysis of the supernatant showed that the recombinant protein PCfPL4$_{298}$ was soluble in Buffer A. Protein contained in the Buffer A supernatant was then purified by nickel ion exchange chromatography and hydroxyapatite chromatography.

EXAMPLE 7

This Example describes the characterization and expression of a flea Peritrophin-like sequence cDNA, referred to herein as PL5.

cDNA nucleic acid molecules 2109–28, 2234–75, 2241–70, 2164–22, 2183–05, and 2162–56, designated SEQ ID NO:33, SEQ ID NO:34, SEQ ID NO:35, SEQ ID NO:36, SEQ ID NO:37 and SEQ ID NO:38, respectively, were isolated from the unsubtracted HMT library as described in Example 1. Sequence analysis revealed that these clones contain overlapping sequence to form a 1513-nucleotide cDNA consensus sequence denoted nCfPL5$_{1513}$, having a coding strand designated SEQ ID NO:39 and a complementary strand designated SEQ ID NO:41. Translation of the coding strand of nCfPL5$_{1513}$ suggests that nucleic acid molecule nCfPL5$_{1513}$ encodes a partial-length Peritrophin-like protein of 339 amino acids, referred to herein as PCfPL5$_{339}$ with an amino acid sequence designated SEQ ID NO:40, assuming a stop codon at nucleotides 1018–1020 of nCfPL5$_{1513}$. Protein PCfPL5$_{339}$ has a predicted weight of 36.5 kDa and a predicted pI of 6.98.

Additional coding sequence 5' to nCfPL5$_{1513}$ was isolated by PCR performed using a RACE cDNA pool prepared as described in Example 2 as template. A first PCR reaction was performed using reverse primer PL5-R1, which is complementary to nucleotides 513–533 of the nCfPL5$_{1513}$ cDNA, having nucleic acid sequence 5' GCG CAT GTA AAA CGA CCC ACG 3', denoted herein as SEQ ID NO:64, in conjunction with the universal primer mix from the SMART RACE cDNA amplification kit described in Example 2, which contains two primers, the first having nucleic acid sequence 5' CTA ATA CGA CTC ACT ATA GGG CAA GCA GTG GTA ACA ACG CAG AGT 3', and the second having nucleotide sequence 5' CTA ATA CGA CTC ACT ATA GGG C 3', denoted as SEQ ID NO:65 and SEQ ID NO:66 respectively, under the following thermocycling conditions: (1) 94° C. for 30 seconds, (2) 35 cycles of 94° C. for 30 seconds, 68 C. for 30 seconds and 72° C. for 3 minutes, (3) 72° C. for 7 minutes. The resulting product was gel purified to reveal a distinct band corresponding to nucleic acid molecule of approximately 850 nucleotides in length, referred to herein as nCfPL5$_{850}$. Fragment nCfPL5$_{850}$ was purified using a QIAquick Gel Extraction Kit, ligated into the pCR II TA Cloning vector, available from Invitrogen, and sequenced using an ABI PRISM 377 automatic DNA Sequencer, available from Perkin Elmer. Sequencing revealed that nucleotides 320–852 of nCfPL5$_{850}$ had 100% identity with nucleotides 1–533 of the nCfPL5$_{1513}$ cDNA. The two sequences were aligned to form a contiguous sequence, denoted nCfPL5$_{1832}$, which is 1832 nucleotides in length, having a coding strand with nucleic acid sequence SEQ ID NO:42 and a complementary sequence having SEQ ID NO:44.

Translation of SEQ ID NO:42 suggests that nucleic acid molecule nCfPL5$_{1832}$ encodes a full-length Peritrophin-like protein of 397 amino acids, referred to herein as PCfCfPL5$_{397}$, having an amino acid sequence represented by SEQ ID NO:43, assuming a start codon spanning nucleotides 146 through 148 and a stop codon spanning nucleotides 1337 through 1339 of SEQ ID NO:42. The coding region encoding PCfCfPL5$_{397}$, is represented by nucleic acid molecule nCfPL5$_{1191}$, having a coding strand with the nucleic acid sequence represented by SEQ ID NO:45 and a complementary strand with nucleic acid sequence represented by SEQ ID NO:46. The amino acid sequence of PCfCfPL5$_{397}$ predicts that PCfCfPL5$_{397}$ has an estimated molecular weight of 43.2 kDa and an estimated pI of 7.4.

Comparison of amino acid sequence SEQ ID NO:43 with amino acid sequences reported in GenBank indicates that SEQ ID NO:43 showed the most homology, i.e., 28% identity with the protein encoded by a *Drosophila melanogaster* cDNA Accession # CAA19845.2. Comparison of SEQ ID NO:45 with nucleic acid sequences reported in GenBank indicates that SEQ ID NO:45 showed the most homology, i.e., 40% with a *Trichoplusia ni* insect intestinal mucin IIM22, GenBank Accession #AF000606. Percent identity calculations were performed using the SeqLab software with default parameters.

A nucleic acid molecule comprising nucleotides 194 through 1354 of SEQ ID NO:42, encoding a predicted mature PL5 protein, was PCR amplified from the HMT RACE pool cDNA described above as follows. Sense primer PL5-FE, having nucleotide sequence 5' CGG GTA CCT TGG AGT CTC AAG AAC TAA TTC 3', which corresponds to nucleotides 194–215 of SEQ ID NO:42 and having a KpnI site indicated in bold, designated herein as SEQ ID NO:67, was used in conjunction with anti-sense primer PL5-RE, having nucleotide sequence 5' AGG AAT TCC ATA TAA CAC ACT CAC TAG GTA CAT GTA G 3', which is complementary to nucleotides 194–215 of SEQ ID NO:42 and having an EcoRI site indicated in bold, designated herein as SEQ ID NO:68 under the following thermocycling conditions: (1) one cycle of 94° for 30 seconds, (2) 30 cycles of 94° for 30 seconds, 68° for 30 seconds, and 72° for 3 minutes, (3) one cycle of 72° for 7 minutes. The products of this reaction were separated on a 1.5% agarose gel, and the appropriate band cut from the gel and purified using the QIAquick Gel Extraction Kit, available from Qiagen. The resulting nucleic acid molecule, referred to herein as nCfPL5$_{1161}$, has a coding strand designated SEQ ID NO:47 and a complementary strand designated SEQ ID NO:49. Translation of SEQ ID NO:47 indicates that SEQ ID NO:47 encodes an approximately 381 amino acid protein, the amino acid sequence of which is designated SEQ ID NO:48, assuming a first codon at nucleotides 1 through 3 and a stop codon at nucleotides 1144 through 1146 of SEQ ID NO:47. The purified product was digested with KpnI and EcoRI and ligated into the vector pTrcHisB, available from Invitrogen, that had been digested with KpnI and EcoRI and treated with alkaline phosphatase. An individual clone was isolated and the DNA extracted and sequenced. DNA sequence analysis of the clone confirmed that nucleotides 194–1354 of SEQ ID NO:42, had been successfully ligated into the pTrcHisB expression vector in frame with the N-terminal T7 Tag epitope encoded by the vector. The recombinant protein, including the T7 Tag, is predicted to be 423 amino acids in length, have a molecular mass of 45.9 kDa and have a pI of 6.36.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. An isolated flea cDNA or flea RNA molecule selected from the group consisting of (a) a flea cDNA or a flea RNA that encodes a protein having an amino acid sequence selected from the group consisting of SEQ ID NO:2 and variants thereof that are at least 95% identical to SEQ ID NO:2 and have peritropin activity; and (b) a flea cDNA or a flea RNA comprising a nucleic acid sequence fully complementary to a nucleic acid molecule of (a).

2. The nucleic acid molecule of claim 1, wherein said nucleic acid molecule is selected from the group consisting of SEQ ID NO:1, SEQ ID NO:3, SEQ ID NO:4, and SEQ ID NO:5.

3. The nucleic acid molecule of claim 1, wherein said nucleic acid molecule encodes a protein having an amino acid sequence SEQ ID NO:2.

4. A recombinant molecule comprising a nucleic acid molecule as set forth in claim 1 operatively linked to a transcription control sequence.

5. A recombinant virus comprising a nucleic acid molecule as set forth in claim 1.

6. A recombinant cell comprising a nucleic acid molecule as set forth in claim 1.

7. A composition comprising an isolated nucleic acid molecule of claim 1 and a component selected from the group consisting of an excipient and a carrier.

8. A method to produce a protein encoded by an isolated nucleic acid molecule of claim 1, said method comprising culturing a cell transformed with a nucleic acid molecule encoding said protein.

9. The method of claim 8, wherein said protein has an amino acid sequence SEQ ID NO:2.

10. The method of claim 8, wherein said nucleic acid molecule comprises a nucleic acid sequence selected from the group consisting of: SEQ ID NO:1 and SEQ ID NO:4.

11. An isolated nucleic acid molecule having a nucleic acid sequence selected from the group consisting of: SEQ ID NO:1, SEQ ID NO:3, SEQ ID NO:4, and SEQ ID NO:5.

* * * * *